US011959069B2

(12) United States Patent
Engels et al.

(10) Patent No.: US 11,959,069 B2
(45) Date of Patent: Apr. 16, 2024

(54) SELF-IMMOLATIVE PLASMID BACKBONE

(71) Applicant: ProteoNic Biotechnology IP B.V., Leiden (NL)

(72) Inventors: Bart Marinus Engels, Woerden (NL); Raymond Michael Dimphena Verhaert, Breda (NL); Maurice Wilhelmus Van der Heijden, Waddinxveen (NL)

(73) Assignee: ProteoNic Biotechnology IP B.V., Leiden (NL)

( * ) Notice: Subject to any disclaimer, the term of this patent is extended or adjusted under 35 U.S.C. 154(b) by 178 days.

(21) Appl. No.: 17/433,609

(22) PCT Filed: Feb. 28, 2020

(86) PCT No.: PCT/EP2020/055249
§ 371 (c)(1),
(2) Date: Aug. 25, 2021

(87) PCT Pub. No.: WO2020/174079
PCT Pub. Date: Sep. 3, 2020

(65) Prior Publication Data

US 2022/0154166 A1 May 19, 2022

(30) Foreign Application Priority Data

Feb. 28, 2019 (EP) .................................... 19160099

(51) Int. Cl.
*C12N 15/10* (2006.01)

(52) U.S. Cl.
CPC .................................. *C12N 15/101* (2013.01)

(58) Field of Classification Search
CPC .................................................... C12N 15/101
USPC ......................................................... 536/25.4
See application file for complete search history.

(56) References Cited

U.S. PATENT DOCUMENTS

2008/0057575 A1* 3/2008 Fernandez-Salas .... C07K 14/33 435/254.2

OTHER PUBLICATIONS

RestrictionMapper version 3. https://restrictionmapper.org. (accessed on Jul. 29, 2023). (Year: 2023).*
QIAquick Gel Extraction Kit. https://www.qiagen.com/us/products/discovery-and-translational-research/dna-rna-purification/dna-purification/dna-clean-up/qiaquick-gel-extraction-kit (accessed on Jul. 29, 2023) (Year: 2023).*
Nucleotide and protein blast. NCBI (accessed on Jul. 27, 2023) (Year: 2023).*
Nurizzo et al. The Crystal Structure of Aminoglycoside-3'-Phosphotransferase-lla, an Enzyme Responsible for Antibiotic Resistance. J. Mol. Biol. (2003) 327, 491-506. (Year: 2003).*
NPS@: Network Protein Sequence Analysis TIBS Mar. 2000 vol. 25, No. 3 [291]: 147-150. (Year: 2000).*
Judith W.Zyskind, Sanford I.Bernstein: "Lab V. TN5 Mutagenesis of PBR329" In: J. W Zyskind and S. I Bernstein: "Recombinant DNA Laboratory Manual", Dec. 31, 1989 (Dec. 31, 1989), Academic press, XP002790549, ISBN: 0127844007, pp. 51-65, p. 57-p. 63.
Jiang et al: "Advanced Design of Minimalistic Dumbbell-shaped Gene Expression Vectors", Aug. 5, 2017 (Aug. 5, 2017), XP002790550, Retrieved from the Internet: URL:https://bio-protocol.org/e2425 [retrieved on Apr. 11, 2019] the whole document.
Database EMBL [Online]; Nov. 10, 2015 (Nov. 10, 2015), "JP 2015517301-A/39: Viral Vectors for the Treatment of Retinal Dystrophy.", XP002790551, retrieved from EBI accession No. EM_PAT:HZ179526 Database accession No. HZ179526.
Database Geneseq [Online]; Jan. 5, 2012 (Jan. 5, 2012), "*Escherichia coli* ApR-Ori DNA sequence, Seq ID 5.", XP002790552, retrieved from EBI accession No. GSN:AZP86474. Database accession No. AZP86474.

* cited by examiner

*Primary Examiner* — Yih-Horng Shiao
(74) *Attorney, Agent, or Firm* — N.V. Nederlandsch Octrooibureau

(57) ABSTRACT

The invention relates to a method for separating a polynucleotide insert from a polynucleotide vector backbone. The backbone has a plurality of cleavage sites distributed such that the backbone is converted into fragments when the sites are cleaved. This allows straightforward separation of the insert from the backbone. The invention also relates to backbones for use in such a method, and to plasmids and kits comprising such backbones.

19 Claims, 3 Drawing Sheets

Specification includes a Sequence Listing.

SEQUENCE LISTING

<160> NUMBER OF SEQ ID NOS: 118

<210> SEQ ID NO 1
<211> LENGTH: 1835
<212> TYPE: DNA
<213> ORGANISM: Artificial Sequence
<220> FEATURE:
<223> OTHER INFORMATION: Reference vector backbone

<400> SEQUENCE: 1
cacgcgtctt aagaccatgt gagcaaaagg ccagcaaaag gccaggaacc gtaaaaaggc 60
cgcgttgctg gcgtttttcc ataggctccg cccccctgac gagcatcaca aaaatcgacg 120
ctcaagtcag aggtggcgaa acccgacagg actataaaga taccaggcgt ttccccctgg 180
aagctccctc gtgcgctctc ctgttccgac cctgccgctt accggatacc tgtccgcctt 240
tctcccttcg ggaagcgtgg cgctttctca tagctcacgc tgtaggtatc tcagttcggt 300
gtaggtcgtt cgctccaagc tgggctgtgt gcacgaaccc cccgttcagc ccgaccgctg 360
cgccttatcc ggtaactatc gtcttgagtc caacccggta agacacgact tatcgccact 420
ggcagcagcc actggtaaca ggattagcag agcgaggtat gtaggcggtg ctacagagtt 480
cttgaagtgg tggcctaact acggctacac tagaagaaca gtatttggta tctgcgctct 540
gctgaagcca gttaccttcg gaaaaagagt tggtagctct tgatccggca aacaaaccac 600
cgctggtagc ggtggttttt ttgtttgcaa gcagcagatt acgcgcagaa aaaaaggatc 660
tcaagaagat cctttgatct tttctacggg gtctgacgct cagtggaacg aaaactcacg 720
ttaagggatt ttggtcatga gattatcaaa aaggatcttc acctagatcc ttttaaatta 780

```
aaaatgaagt tttaaatcaa tctaaagtat atatgagtaa acttggtctg acagttagaa    840
aaactcatcg agcatcaaat gaaactgcaa tttattcata tcaggattat caataccata    900
tttttgaaaa agccgtttct gtaatgaagg agaaaactca ccgaggcagt tccataggat    960
ggcaagatcc tggtatcggt ctgcgattcc gactcgtcca acatcaatac aacctattaa   1020
tttcccctcg tcaaaaataa ggttatcaag tgagaaatca ccatgagtga cgactgaatc   1080
cggtgagaat ggcaaaagtt tatgcatttc tttccagact tgttcaacag gccagccatt   1140
acgctcgtca tcaaaatcac tcgcatcaac caaaccgtta ttcattcgtg attgcgcctg   1200
agcgagacga aatacgcgat cgctgttaaa aggacaatta caaacaggaa tcgaatgcaa   1260
ccggcgcagg aacactgcca gcgcatcaac aatattttca cctgaatcag gatattcttc   1320
taatacctgg aatgctgttt tcccagggat cgcagtggtg agtaaccatg catcatcagg   1380
agtacggata aaatgcttga tggtcggaag aggcataaat tccgtcagcc agtttagtct   1440
gaccatctca tctgtaacat cattggcaac gctacctttg ccatgtttca gaaacaactc   1500
tggcgcatcg ggcttcccat acaatcgata gattgtcgca cctgattgcc cgacattatc   1560
gcgagcccat ttatacccat ataaatcagc atccatgttg gaatttaatc gcggcctaga   1620
gcaagacgtt tcccgttgaa tatggctcat actcttcctt tttcaatatt attgaagcat   1680
ttatcagggt tattgtctca tgagcggata catatttgaa tgtatttaga aaaataaaca   1740
aataggggtt ccgcgcacat ttccccgaaa agtgccacct gacgtctaag aaaccattat   1800
tatcatgaca ttaacctata aaaataggcg tatca                              1835
```

<210> SEQ ID NO 2
<211> LENGTH: 4470
<212> TYPE: DNA
<213> ORGANISM: Artificial Sequence
<220> FEATURE:
<223> OTHER INFORMATION: Vector backbone

<400> SEQUENCE: 2

```
ctttcctgcg ttatcccctg attctgtgga taaccgtatt accgctagcc aggaagagtt     60
tgtagaaacg caaaaaggcc atccgtcagg atggccttct gcttagtttg atgcctggca    120
gtttatggcg ggcgtcctgc ccgccaccct ccgggccgtt gcttcacaac gttcaaatcc    180
gctcccggcg gatttgtcct actcaggaga gcgttcaccg acaaacaaca gataaaacga    240
aaggcccagt cttccgactg agcctttcgt tttatttgat gcctggcagt tccctactct    300
cgcgttaacg ctagcatgga tctcgggccc caaataatga ttttattttg actgatagtg    360
acctgttcgt tgcaacaaat tgatgagcaa tgctttttta taatgccaag tttgtacaaa    420
aaagcagaac gagaaacgta aaatgatata aatatcaata tattaaatta gattttgcat    480
aaaaaacaga ctacataata ctgtaaaaca caacatatcc agtcactatg aatcaactac    540
ttagatggta ttagtgacct gtagtcgacc gacagccttc caaatgttct tcgggtgatg    600
ctgccaactt agtcgaccga cagccttcca aatgttcttc tcaaacggaa tcgtcgtatc    660
cagcctactc gctattgtcc tcaatgccgt attaaatcat aaaaagaaat aagaaaaaga    720
ggtgcgagcc tctttttgt gtgacaaaat aaaaacatct acctattcat atacgctagt    780
gtcatagtcc tgaaaatcat ctgcatcaag aacaatttca caactcttat acttttctct    840
tacaagtcgt tcggcttcat ctggattttc agcctctata cttactaaac gtgataaagt    900
ttctgtaatt tctactgtat cgacctgcag actggctgtg tataagggag cctgacattt    960
atattcccca gaacatcagg ttaatggcgt ttttgatgtc attttcgcgg tggctgagat   1020
```

```
cagccacttc ttccccgata acggagaccg gcacactggc catatcggtg gtcatcatgc   1080
gccagctttc atccccgata tgcaccaccg ggtaaagttc acgggagact ttatctgaca   1140
gcagacgtgc actggccagg gggatcacca tccgtcgccc gggcgtgtca ataatatcac   1200
tctgtacatc cacaaacaga cgataacggc tctctctttt ataggtgtaa accttaaact   1260
gcatttcacc agtccctgtt ctcgtcagca aaagagccgt tcatttcaat aaaccgggcg   1320
acctcagcca tcccttcctg attttccgct ttccagcgtt cggcacgcag acgacgggct   1380
tcattctgca tggttgtgct taccagaccg gagatattga catcatatat gccttgagca   1440
actgatagct gtcgctgtca actgtcactg taatacgctg cttcatagca cacctctttt   1500
tgacatactt cgggtataca tatcagtata tattcttata ccgcaaaaat cagcgcgcaa   1560
atacgcatac tgttatctgg cttttagtaa gccggatcca cgcgattacg ccccgccctg   1620
ccactcatcg cagtactgtt gtaattcatt aagcattctg ccgacatgga agccatcaca   1680
gacggcatga tgaacctgaa tcgccagcgg catcagcacc ttgtcgcctt gcgtataata   1740
tttgcccatg gtgaaaacgg gggcgaagaa gttgtccata ttggccacgt ttaaatcaaa   1800
actggtgaaa ctcacccagg gattggctga gacgaaaaac atattctcaa taaacccttt   1860
agggaaatag gccaggtttt caccgtaaca cgccacatct tgcgaatata tgtgtagaaa   1920
ctgccggaaa tcgtcgtggt attcactcca gagcgatgaa aacgtttcag tttgctcatg   1980
gaaaacggtg taacaagggt gaacactatc ccatatcacc agctcaccgt ctttcattgc   2040
catacggaat tccggatgag cattcatcag gcgggcaaga atgtgaataa aggccggata   2100
aaacttgtgc ttatttttct ttacggtctt taaaaaggcc gtaatatcca gctgaacggt   2160
ctggttatag gtacattgag caactgactg aaatgcctca aaatgttctt tacgatgcca   2220
ttgggatata tcaacggtgg tatatccagt gatttttttc tccattttag cttccttagc   2280
tcctgaaaat ctcgataact caaaaaatac gcccggtagt gatcttattt cattatggtg   2340
aaagttggaa cctcttacgt gccgatcaac gtctcatttt cgccaaaagt tggcccaggg   2400
cttcccggta tcaacaggga caccaggatt tatttattct gcgaagtgat cttccgtcac   2460
aggtatttat tcggcgcaaa gtgcgtcggg tgatgctgcc aacttagtcg actacaggtc   2520
actaatacca tctaagtagt tgattcatag tgactggata tgttgtgttt tacagtatta   2580
tgtagtctgt tttttatgca aaatctaatt taatatattg atatttatat cattttacgt   2640
ttctcgttca gctttcttgt acaaagtggg cattataaga aagcattgct tatcaatttg   2700
ttgcaacgaa caggtcacta tcagtcaaaa taaaatcatt atttgccatc cagctgcagc   2760
tctggcccgt gtctcaaaat ctctgatgtt acattgcaca agataaaaat atatcatcat   2820
gaacaataaa actgtctgct tacataaaca gtaatacaag gggtgttatg agccatattc   2880
aacgggaaac gtcgaggccg cgattaaatt ccaacatgga tgctgattta tatgggtata   2940
aatgggctcg cgataatgtc gggcaatcag gtgcgacaat ctatcgcttg tatgggaagc   3000
ccgatgcgcc agagttgttt ctgaaacatg gcaaaggtag cgttgccaat gatgttacag   3060
atgagatggt cagactaaac tggctgacgg aatttatgcc tcttccgacc atcaagcatt   3120
ttatccgtac tcctgatgat gcatggttac tcaccactgc gatccccgga aaaacagcat   3180
tccaggtatt agaagaatat cctgattcag gtgaaaatat tgttgatgcg ctggcagtgt   3240
tcctgcgccg gttgcattcg attcctgttt gtaattgtcc ttttaacagc gatcgcgtat   3300
ttcgtctcgc tcaggcgcaa tcacgaatga ataacggttt ggttgatgcg agtgattttg   3360
```

```
atgacgagcg taatggctgg cctgttgaac aagtctggaa agaaatgcat aaacttttgc   3420

cattctcacc ggattcagtc gtcactcatg gtgatttctc acttgataac cttatttttg   3480

acgaggggaa attaataggt tgtattgatg ttggacgagt cggaatcgca gaccgatacc   3540

aggatcttgc catcctatgg aactgcctcg gtgagttttc tccttcatta cagaaacggc   3600

tttttcaaaa atatggtatt gataatcctg atatgaataa attgcagttt catttgatgc   3660

tcgatgagtt tttctaatca gaattggtta attggttgta acactggcag agcattacgc   3720

tgacttgacg ggacggcgca agctcatgac caaaatccct taacgtgagt tttcgttcca   3780

ctgagcgtca gaccccgtag aaaagatcaa aggatcttct tgagatcctt tttttctgcg   3840

cgtaatctgc tgcttgcaaa caaaaaaacc accgctacca gcggtggttt gtttgccgga   3900

tcaagagcta ccaactcttt ttccgaaggt aactggcttc agcagagcgc agataccaaa   3960

tactgtcctt ctagtgtagc cgtagttagg ccaccacttc aagaactctg tagcaccgcc   4020

tacatacctc gctctgctaa tcctgttacc agtggctgct gccagtggcg ataagtcgtg   4080

tcttaccggg ttggactcaa gacgatagtt accggataag gcgcagcggt cgggctgaac   4140

ggggggttcg tgcacacagc ccagcttgga gcgaacgacc tacaccgaac tgagatacct   4200

acagcgtgag ctatgagaaa gcgccacgct tcccgaaggg agaaaggcgg acaggtatcc   4260

ggtaagcggc agggtcggaa caggagagcg cacgagggag cttccagggg gaaacgcctg   4320

gtatctttat agtcctgtcg ggtttcgcca cctctgactt gagcgtcgat ttttgtgatg   4380

ctcgtcaggg gggcggagcc tatggaaaaa cgccagcaac gcggcctttt tacggttcct   4440

ggccttttgc tggccttttg ctcacatgtt                                    4470
```

```
<210> SEQ ID NO 3
<211> LENGTH: 3000
<212> TYPE: DNA
<213> ORGANISM: Artificial Sequence
<220> FEATURE:
<223> OTHER INFORMATION: Vector backbone

<400> SEQUENCE: 3

gggcgaattg ggcccgacgt cgcatgctcc cggccgccat ggccgcggga tatcactagt     60

gcggccgcct gcaggtcgac catatgggag agctcccaac gcgttggatg catagcttga    120

gtattctata gtgtcaccta aatagcttgg cgtaatcatg gtcatagctg tttcctgtgt    180

gaaattgtta tccgctcaca attccacaca acatacgagc cggaagcata aagtgtaaag    240

cctggggtgc ctaatgagtg agctaactca cattaattgc gttgcgctca ctgcccgctt    300

tccagtcggg aaacctgtcg tgccagctgc attaatgaat cggccaacgc gcggggagag    360

gcggtttgcg tattgggcgc tcttccgctt cctcgctcac tgactcgctg cgctcggtcg    420

ttcggctgcg gcgagcggta tcagctcact caaaggcggt aatacggtta tccacagaat    480

caggggataa cgcaggaaag aacatgtgag caaaaggcca gcaaaaggcc aggaaccgta    540

aaaaggccgc gttgctggcg tttttccata ggctccgccc ccctgacgag catcacaaaa    600

atcgacgctc aagtcagagg tggcgaaacc cgacaggact ataaagatac caggcgtttc    660

cccctggaag ctccctcgtg cgctctcctg ttccgaccct gccgcttacc ggatacctgt    720

ccgcctttct cccttcggga agcgtggcgc tttctcatag ctcacgctgt aggtatctca    780

gttcggtgta ggtcgttcgc tccaagctgg gctgtgtgca cgaacccccc gttcagcccg    840

accgctgcgc cttatccggt aactatcgtc ttgagtccaa cccggtaaga cacgacttat    900

cgccactggc agcagccact ggtaacagga ttagcagagc gaggtatgta ggcggtgcta    960
```

```
cagagttctt gaagtggtgg cctaactacg gctacactag aagaacagta tttggtatct   1020

gcgctctgct gaagccagtt accttcggaa aaagagttgg tagctcttga tccggcaaac   1080

aaaccaccgc tggtagcggt ggtttttttg tttgcaagca gcagattacg cgcagaaaaa   1140

aaggatctca agaagatcct ttgatctttt ctacggggtc tgacgctcag tggaacgaaa   1200

actcacgtta agggattttg gtcatgagat tatcaaaaag gatcttcacc tagatccttt   1260

taaattaaaa atgaagtttt aaatcaatct aaagtatata tgagtaaact tggtctgaca   1320

gttaccaatg cttaatcagt gaggcaccta tctcagcgat ctgtctattt cgttcatcca   1380

tagttgcctg actccccgtc gtgtagataa ctacgatacg ggagggctta ccatctggcc   1440

ccagtgctgc aatgataccg cgagacccac gctcaccggc tccagattta tcagcaataa   1500

accagccagc cggaagggcc gagcgcagaa gtggtcctgc aactttatcc gcctccatcc   1560

agtctattaa ttgttgccgg gaagctagag taagtagttc gccagttaat agtttgcgca   1620

acgttgttgc cattgctaca ggcatcgtgg tgtcacgctc gtcgtttggt atggcttcat   1680

tcagctccgg ttcccaacga tcaaggcgag ttacatgatc ccccatgttg tgcaaaaaag   1740

cggttagctc cttcggtcct ccgatcgttg tcagaagtaa gttggccgca gtgttatcac   1800

tcatggttat ggcagcactg cataattctc ttactgtcat gccatccgta agatgctttt   1860

ctgtgactgg tgagtactca accaagtcat tctgagaata gtgtatgcgg cgaccgagtt   1920

gctcttgccc ggcgtcaata cgggataata ccgcgccaca tagcagaact ttaaaagtgc   1980

tcatcattgg aaaacgttct tcggggcgaa aactctcaag gatcttaccg ctgttgagat   2040

ccagttcgat gtaacccact cgtgcaccca actgatcttc agcatctttt actttcacca   2100

gcgtttctgg gtgagcaaaa acaggaaggc aaaatgccgc aaaaaaggga ataagggcga   2160

cacggaaatg ttgaatactc atactcttcc tttttcaata ttattgaagc atttatcagg   2220

gttattgtct catgagcgga tacatatttg aatgtattta gaaaaataaa caaatagggg   2280

ttccgcgcac atttccccga aaagtgccac ctgatgcggt gtgaaatacc gcacagatgc   2340

gtaaggagaa aataccgcat caggaaattg taagcgttaa tattttgtta aaattcgcgt   2400

taaatttttg ttaaatcagc tcatttttta accaataggc cgaaatcggc aaaatccctt   2460

ataaatcaaa agaatagacc gagatagggt tgagtgttgt tccagtttgg aacaagagtc   2520

cactattaaa gaacgtggac tccaacgtca aagggcgaaa aaccgtctat cagggcgatg   2580

gcccactacg tgaaccatca ccctaatcaa gtttttttggg gtcgaggtgc cgtaaagcac   2640

taaatcggaa ccctaaaggg agcccccgat ttagagcttg acggggaaag ccggcgaacg   2700

tggcgagaaa ggaagggaag aaagcgaaag gagcgggcgc tagggcgctg gcaagtgtag   2760

cggtcacgct gcgcgtaacc accacacccg ccgcgcttaa tgcgccgcta cagggcgcgt   2820

ccattcgcca ttcaggctgc gcaactgttg ggaagggcga tcggtgcggg cctcttcgct   2880

attacgccag ctggcgaaag ggggatgtgc tgcaaggcga ttaagttggg taacgccagg   2940

gttttcccag tcacgacgtt gtaaaacgac ggccagtgaa ttgtaatacg actcactata   3000
```

<210> SEQ ID NO 4
<211> LENGTH: 5428
<212> TYPE: DNA
<213> ORGANISM: Artificial Sequence
<220> FEATURE:
<223> OTHER INFORMATION: Vector backbone

<400> SEQUENCE: 4

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattctgc    960
agatatccag cacagtggcg gccgctcgag tctagagggc ccgtttaaac ccgctgatca   1020
gcctcgactg tgccttctag ttgccagcca tctgttgttt gcccctcccc cgtgccttcc   1080
ttgaccctgg aaggtgccac tcccactgtc ctttcctaat aaaatgagga aattgcatcg   1140
cattgtctga gtaggtgtca ttctattctg gggggtgggg tggggcagga cagcaagggg   1200
gaggattggg aagacaatag caggcatgct ggggatgcgg tgggctctat ggcttctgag   1260
gcggaaagaa ccagctgggg ctctaggggg tatccccacg cgccctgtag cggcgcatta   1320
agcgcggcgg gtgtggtggt tacgcgcagc gtgaccgcta cacttgccag cgccctagcg   1380
cccgctcctt tcgctttctt cccttccttt ctcgccacgt tcgccggctt tccccgtcaa   1440
gctctaaatc gggggctccc tttagggttc cgatttagtg ctttacggca cctcgacccc   1500
aaaaaacttg attagggtga tggttcacgt agtgggccat cgccctgata gacggttttt   1560
cgccctttga cgttggagtc cacgttcttt aatagtggac tcttgttcca aactggaaca   1620
acactcaacc ctatctcggt ctattctttt gatttataag ggattttgcc gatttcggcc   1680
tattggttaa aaaatgagct gatttaacaa aaatttaacg cgaattaatt ctgtggaatg   1740
tgtgtcagtt agggtgtgga aagtccccag gctccccagc aggcagaagt atgcaaagca   1800
tgcatctcaa ttagtcagca accaggtgtg gaaagtcccc aggctcccca gcaggcagaa   1860
gtatgcaaag catgcatctc aattagtcag caaccatagt cccgccccta actccgccca   1920
tcccgcccct aactccgccc agttccgccc attctccgcc ccatggctga ctaatttttt   1980
ttatttatgc agaggccgag gccgcctctg cctctgagct attccagaag tagtgaggag   2040
gcttttttgg aggcctaggc ttttgcaaaa agctcccggg agcttgtata tccattttcg   2100
gatctgatca agagacagga tgaggatcgt ttcgcatgat tgaacaagat ggattgcacg   2160
caggttctcc ggccgcttgg gtggagaggc tattcggcta tgactgggca caacagacaa   2220
tcggctgctc tgatgccgcc gtgttccggc tgtcagcgca ggggcgcccg gttctttttg   2280
tcaagaccga cctgtccggt gccctgaatg aactgcagga cgaggcagcg cggctatcgt   2340
ggctggccac gacgggcgtt ccttgcgcag ctgtgctcga cgttgtcact gaagcgggaa   2400
```

```
gggactggct gctattgggc gaagtgccgg ggcaggatct cctgtcatct caccttgctc   2460
ctgccgagaa agtatccatc atggctgatg caatgcggcg gctgcatacg cttgatccgg   2520
ctacctgccc attcgaccac caagcgaaac atcgcatcga gcgagcacgt actcggatgg   2580
aagccggtct tgtcgatcag gatgatctgg acgaagagca tcaggggctc gcgccagccg   2640
aactgttcgc caggctcaag gcgcgcatgc ccgacggcga ggatctcgtc gtgacccatg   2700
gcgatgcctg cttgccgaat atcatggtgg aaaatggccg cttttctgga ttcatcgact   2760
gtggccggct gggtgtggcg gaccgctatc aggacatagc gttggctacc cgtgatattg   2820
ctgaagagct tggcggcgaa tgggctgacc gcttcctcgt gctttacggt atcgccgctc   2880
ccgattcgca gcgcatcgcc ttctatcgcc ttcttgacga gttcttctga gcgggactct   2940
ggggttcgaa atgaccgacc aagcgacgcc caacctgcca tcacgagatt tcgattccac   3000
cgccgccttc tatgaaaggt tgggcttcgg aatcgttttc cgggacgccg gctggatgat   3060
cctccagcgc ggggatctca tgctggagtt cttcgcccac cccaacttgt ttattgcagc   3120
ttataatggt tacaaataaa gcaatagcat cacaaatttc acaaataaag catttttttc   3180
actgcattct agttgtggtt tgtccaaact catcaatgta tcttatcatg tctgtatacc   3240
gtcgacctct agctagagct tggcgtaatc atggtcatag ctgtttcctg tgtgaaattg   3300
ttatccgctc acaattccac acaacatacg agccggaagc ataaagtgta aagcctgggg   3360
tgcctaatga gtgagctaac tcacattaat tgcgttgcgc tcactgcccg ctttccagtc   3420
gggaaacctg tcgtgccagc tgcattaatg aatcggccaa cgcgcgggga gaggcggttt   3480
gcgtattggg cgctcttccg cttcctcgct cactgactcg ctgcgctcgg tcgttcggct   3540
gcggcgagcg gtatcagctc actcaaaggc ggtaatacgg ttatccacag aatcagggga   3600
taacgcagga aagaacatgt gagcaaaagg ccagcaaaag gccaggaacc gtaaaaaggc   3660
cgcgttgctg gcgtttttcc ataggctccg cccccctgac gagcatcaca aaaatcgacg   3720
ctcaagtcag aggtggcgaa acccgacagg actataaaga taccaggcgt ttccccctgg   3780
aagctccctc gtgcgctctc ctgttccgac cctgccgctt accggatacc tgtccgcctt   3840
tctcccttcg ggaagcgtgg cgctttctca tagctcacgc tgtaggtatc tcagttcggt   3900
gtaggtcgtt cgctccaagc tgggctgtgt gcacgaaccc cccgttcagc ccgaccgctg   3960
cgccttatcc ggtaactatc gtcttgagtc caacccggta agacacgact tatcgccact   4020
ggcagcagcc actggtaaca ggattagcag agcgaggtat gtaggcggtg ctacagagtt   4080
cttgaagtgg tggcctaact acggctacac tagaagaaca gtatttggta tctgcgctct   4140
gctgaagcca gttaccttcg gaaaaagagt tggtagctct tgatccggca aacaaaccac   4200
cgctggtagc ggtttttttg tttgcaagca gcagattacg cgcagaaaaa aaggatctca   4260
agaagatcct ttgatctttt ctacggggtc tgacgctcag tggaacgaaa actcacgtta   4320
agggattttg gtcatgagat tatcaaaaag gatcttcacc tagatccttt taaattaaaa   4380
atgaagtttt aaatcaatct aaagtatata tgagtaaact tggtctgaca gttaccaatg   4440
cttaatcagt gaggcaccta tctcagcgat ctgtctattt cgttcatcca tagttgcctg   4500
actccccgtc gtgtagataa ctacgatacg ggagggctta ccatctggcc ccagtgctgc   4560
aatgataccg cgagacccac gctcaccggc tccagattta tcagcaataa accagccagc   4620
cggaagggcc gagcgcagaa gtggtcctgc aactttatcc gcctccatcc agtctattaa   4680
ttgttgccgg gaagctagag taagtagttc gccagttaat agtttgcgca acgttgttgc   4740
```

```
cattgctaca ggcatcgtgg tgtcacgctc gtcgtttggt atggcttcat tcagctccgg   4800

ttcccaacga tcaaggcgag ttacatgatc ccccatgttg tgcaaaaaag cggttagctc   4860

cttcggtcct ccgatcgttg tcagaagtaa gttggccgca gtgttatcac tcatggttat   4920

ggcagcactg cataattctc ttactgtcat gccatccgta agatgctttt ctgtgactgg   4980

tgagtactca accaagtcat tctgagaata gtgtatgcgg cgaccgagtt gctcttgccc   5040

ggcgtcaata cgggataata ccgcgccaca tagcagaact ttaaaagtgc tcatcattgg   5100

aaaacgttct tcggggcgaa aactctcaag gatcttaccg ctgttgagat ccagttcgat   5160

gtaacccact cgtgcaccca actgatcttc agcatctttt actttcacca gcgtttctgg   5220

gtgagcaaaa acaggaaggc aaaatgccgc aaaaaaggga ataagggcga cacggaaatg   5280

ttgaatactc atactcttcc tttttcaata ttattgaagc atttatcagg gttattgtct   5340

catgagcgga tacatatttg aatgtattta gaaaaataaa caaatagggg ttccgcgcac   5400

atttccccga aaagtgccac ctgacgtc                                      5428
```

<210> SEQ ID NO 5
<211> LENGTH: 2710
<212> TYPE: DNA
<213> ORGANISM: Artificial Sequence
<220> FEATURE:
<223> OTHER INFORMATION: Vector backbone

<400> SEQUENCE: 5

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgagctcggt acctcgcgaa    420

tgcatctaga tatcggatcc cgggcccgtc gactgcagag gcctgcatgc aagcttggcg    480

taatcatggt catagctgtt tcctgtgtga aattgttatc cgctcacaat tccacacaac    540

atacgagccg gaagcataaa gtgtaaagcc tggggtgcct aatgagtgag ctaactcaca    600

ttaattgcgt tgcgctcact gcccgctttc cagtcgggaa acctgtcgtg ccagctgcat    660

taatgaatcg gccaacgcgc ggggagaggc ggtttgcgta ttgggcgctc ttccgcttcc    720

tcgctcactg actcgctgcg ctcggtcgtt cggctgcggc gagcggtatc agctcactca    780

aaggcggtaa tacggttatc cacagaatca ggggataacg caggaaagaa catgtgagca    840

aaaggccagc aaaaggccag gaaccgtaaa aaggccgcgt tgctggcgtt tttccatagg    900

ctccgccccc ctgacgagca tcacaaaaat cgacgctcaa gtcagaggtg gcgaaacccg    960

acaggactat aaagatacca ggcgtttccc cctggaagct ccctcgtgcg ctctcctgtt   1020

ccgaccctgc cgcttaccgg atacctgtcc gcctttctcc cttcgggaag cgtggcgctt   1080

tctcatagct cacgctgtag gtatctcagt tcggtgtagg tcgttcgctc caagctgggc   1140

tgtgtgcacg aaccccccgt tcagcccgac cgctgcgcct tatccggtaa ctatcgtctt   1200

gagtccaacc cggtaagaca cgacttatcg ccactggcag cagccactgg taacaggatt   1260

agcagagcga ggtatgtagg cggtgctaca gagttcttga agtggtggcc taactacggc   1320

tacactagaa gaacagtatt tggtatctgc gctctgctga agccagttac cttcggaaaa   1380
```

```
agagttggta gctcttgatc cggcaaacaa accaccgctg gtagcggtgg tttttttgtt   1440

tgcaagcagc agattacgcg cagaaaaaaa ggatctcaag aagatccttt gatcttttct   1500

acggggtctg acgctcagtg gaacgaaaac tcacgttaag ggattttggt catgagatta   1560

tcaaaaagga tcttcaccta gatcctttta aattaaaaat gaagttttaa atcaatctaa   1620

agtatatatg agtaaacttg gtctgacagt taccaatgct taatcagtga ggcacctatc   1680

tcagcgatct gtctatttcg ttcatccata gttgcctgac tccccgtcgt gtagataact   1740

acgatacggg agggcttacc atctggcccc agtgctgcaa tgataccgcg agacccacgc   1800

tcaccggctc cagatttatc agcaataaac cagccagccg gaagggccga gcgcagaagt   1860

ggtcctgcaa ctttatccgc ctccatccag tctattaatt gttgccggga agctagagta   1920

agtagttcgc cagttaatag tttgcgcaac gttgttgcca ttgctacagg catcgtggtg   1980

tcacgctcgt cgtttggtat ggcttcattc agctccggtt cccaacgatc aaggcgagtt   2040

acatgatccc ccatgttgtg caaaaaagcg gttagctcct tcggtcctcc gatcgttgtc   2100

agaagtaagt tggccgcagt gttatcactc atggttatgg cagcactgca taattctctt   2160

actgtcatgc catccgtaag atgcttttct gtgactggtg agtactcaac caagtcattc   2220

tgagaatagt gtatgcggcg accgagttgc tcttgcccgg cgtcaatacg ggataatacc   2280

gcgccacata gcagaacttt aaaagtgctc atcattggaa aacgttcttc ggggcgaaaa   2340

ctctcaagga tcttaccgct gttgagatcc agttcgatgt aacccactcg tgcacccaac   2400

tgatcttcag catcttttac tttcaccagc gtttctgggt gagcaaaaac aggaaggcaa   2460

aatgccgcaa aaaagggaat aagggcgaca cggaaatgtt gaatactcat actcttcctt   2520

tttcaatatt attgaagcat ttatcagggt tattgtctca tgagcggata catatttgaa   2580

tgtatttaga aaaataaaca aataggggtt ccgcgcacat ttccccgaaa agtgccacct   2640

gacgtctaag aaaccattat tatcatgaca ttaacctata aaaataggcg tatcacgagg   2700

ccctttcgtc                                                          2710
```

<210> SEQ ID NO 6
<211> LENGTH: 5900
<212> TYPE: DNA
<213> ORGANISM: Artificial Sequence
<220> FEATURE:
<223> OTHER INFORMATION: Vector backbone

<400> SEQUENCE: 6

```
atccggatat agttcctcct ttcagcaaaa aacccctcaa gacccgttta gaggccccaa     60

ggggttatgc tagttattgc tcagcggtgg cagcagccaa ctcagcttcc tttcgggctt    120

tgttagcagc cggatctcag tggtggtggt ggtggtgctc gagtgcggcc gcaagcttgt    180

cgacggagct cgaattcgga tccgatatca gccatggcct tgtcgtcgtc gtcggtaccc    240

agatctgggc tgtccatgtg ctggcgttcg aatttagcag cagcggtttc tttcatacca    300

gaaccgcgtg gcaccagacc agaagaatga tgatgatgat ggtgcatatg gccagaacca    360

gaaccggcca ggttagcgtc gaggaactct ttcaactgac ctttagacag tgcacccact    420

ttggttgccg ccacttcacc gtttttgaac agcagcagag tcgggatacc acggatgcca    480

tatttcggcg cagtgccagg gttttgatcg atgttcagtt ttgcaacggt cagtttgccc    540

tgatattcgt cagcgatttc atccagaatc ggggcgatca ttttgcacgg accgcaccac    600

tctgcccaga aatcgacgag gatcgccccg tccgctttga gtacatccgt gtcaaaactg    660
```

```
tcgtcagtca ggtgaataat tttatcgctc atatgtatat ctccttctta aagttaaaca    720
aaattatttc tagaggggaa ttgttatccg ctcacaattc ccctatagtg agtcgtatta    780
atttcgcggg atcgagatcg atctcgatcc tctacgccgg acgcatcgtg gccggcatca    840
ccggcgccac aggtgcggtt gctggcgcct atatcgccga catcaccgat ggggaagatc    900
gggctcgcca cttcgggctc atgagcgctt gtttcggcgt gggtatggtg gcaggccccg    960
tggccggggg actgttgggc gccatctcct tgcatgcacc attccttgcg gcggcggtgc   1020
tcaacggcct caacctacta ctgggctgct tcctaatgca ggagtcgcat aagggagagc   1080
gtcgagatcc cggacaccat cgaatggcgc aaaacctttc gcggtatggc atgatagcgc   1140
ccggaagaga gtcaattcag ggtggtgaat gtgaaaccag taacgttata cgatgtcgca   1200
gagtatgccg gtgtctctta tcagaccgtt tcccgcgtgg tgaaccaggc cagccacgtt   1260
tctgcgaaaa cgcgggaaaa agtggaagcg gcgatggcgg agctgaatta cattcccaac   1320
cgcgtggcac aacaactggc gggcaaacag tcgttgctga ttggcgttgc cacctccagt   1380
ctggccctgc acgcgccgtc gcaaattgtc gcggcgatta aatctcgcgc cgatcaactg   1440
ggtgccagcg tggtggtgtc gatggtagaa cgaagcggcg tcgaagcctg taaagcggcg   1500
gtgcacaatc ttctcgcgca acgcgtcagt gggctgatca ttaactatcc gctggatgac   1560
caggatgcca ttgctgtgga agctgcctgc actaatgttc cggcgttatt tcttgatgtc   1620
tctgaccaga cacccatcaa cagtattatt ttctcccatg aagacggtac gcgactgggc   1680
gtggagcatc tggtcgcatt gggtcaccag caaatcgcgc tgttagcggg cccattaagt   1740
tctgtctcgg cgcgtctgcg tctggctggc tggcataaat atctcactcg caatcaaatt   1800
cagccgatag cggaacggga aggcgactgg agtgccatgt ccggttttca acaaaccatg   1860
caaatgctga atgagggcat cgttcccact gcgatgctgg ttgccaacga tcagatggcg   1920
ctgggcgcaa tgcgcgccat taccgagtcc gggctgcgcg ttggtgcgga catctcggta   1980
gtgggatacg acgataccga agacagctca tgttatatcc cgccgttaac caccatcaaa   2040
caggattttc gcctgctggg gcaaaccagc gtggaccgct tgctgcaact ctctcagggc   2100
caggcggtga agggcaatca gctgttgccc gtctcactgg tgaaaagaaa aaccaccctg   2160
gcgcccaata cgcaaaccgc ctctccccgc gcgttggccg attcattaat gcagctggca   2220
cgacaggttt cccgactgga aagcgggcag tgagcgcaac gcaattaatg taagttagct   2280
cactcattag gcaccgggat ctcgaccgat gcccttgaga gccttcaacc cagtcagctc   2340
cttccggtgg gcgcggggca tgactatcgt cgccgcactt atgactgtct tctttatcat   2400
gcaactcgta ggacaggtgc cggcagcgct ctgggtcatt ttcggcgagg accgctttcg   2460
ctggagcgcg acgatgatcg gcctgtcgct tgcggtattc ggaatcttgc acgccctcgc   2520
tcaagccttc gtcactggtc ccgccaccaa acgtttcggc gagaagcagg ccattatcgc   2580
cggcatggcg gccccacggg tgcgcatgat cgtgctcctg tcgttgagga cccggctagg   2640
ctggcggggt tgccttactg gttagcagaa tgaatcaccg atacgcgagc gaacgtgaag   2700
cgactgctgc tgcaaaacgt ctgcgacctg agcaacaaca tgaatggtct tcggtttccg   2760
tgtttcgtaa agtctggaaa cgcggaagtc agcgccctgc accattatgt tccggatctg   2820
catcgcagga tgctgctggc taccctgtgg aacacctaca tctgtattaa cgaagcgctg   2880
gcattgaccc tgagtgattt ttctctggtc ccgccgcatc cataccgcca gttgtttacc   2940
ctcacaacgt tccagtaacc gggcatgttc atcatcagta acccgtatcg tgagcatcct   3000
ctctcgtttc atcggtatca ttacccccat gaacagaaat cccccttaca cggaggcatc   3060
```

```
agtgaccaaa caggaaaaaa ccgcccttaa catggcccgc tttatcagaa gccagacatt   3120
aacgcttctg gagaaactca acgagctgga cgcggatgaa caggcagaca tctgtgaatc   3180
gcttcacgac cacgctgatg agctttaccg cagctgcctc gcgcgtttcg gtgatgacgg   3240
tgaaaacctc tgacacatgc agctcccgga gacggtcaca gcttgtctgt aagcggatgc   3300
cgggagcaga caagcccgtc agggcgcgtc agcgggtgtt ggcgggtgtc ggggcgcagc   3360
catgacccag tcacgtagcg atagcggagt gtatactggc ttaactatgc ggcatcagag   3420
cagattgtac tgagagtgca ccatatatgc ggtgtgaaat accgcacaga tgcgtaagga   3480
gaaaataccg catcaggcgc tcttccgctt cctcgctcac tgactcgctg cgctcggtcg   3540
ttcggctgcg gcgagcggta tcagctcact caaaggcggt aatacggtta tccacagaat   3600
caggggataa cgcaggaaag aacatgtgag caaaaggcca gcaaaaggcc aggaaccgta   3660
aaaaggccgc gttgctggcg tttttccata ggctccgccc ccctgacgag catcacaaaa   3720
atcgacgctc aagtcagagg tggcgaaacc cgacaggact ataaagatac caggcgtttc   3780
cccctggaag ctccctcgtg cgctctcctg ttccgaccct gccgcttacc ggatacctgt   3840
ccgcctttct cccttcggga agcgtggcgc tttctcatag ctcacgctgt aggtatctca   3900
gttcggtgta ggtcgttcgc tccaagctgg gctgtgtgca cgaacccccc gttcagcccg   3960
accgctgcgc cttatccggt aactatcgtc ttgagtccaa cccggtaaga cacgacttat   4020
cgccactggc agcagccact ggtaacagga ttagcagagc gaggtatgta ggcggtgcta   4080
cagagttctt gaagtggtgg cctaactacg gctacactag aaggacagta tttggtatct   4140
gcgctctgct gaagccagtt accttcggaa aaagagttgg tagctcttga tccggcaaac   4200
aaaccaccgc tggtagcggt ggtttttttg tttgcaagca gcagattacg cgcagaaaaa   4260
aaggatctca agaagatcct ttgatctttt ctacggggtc tgacgctcag tggaacgaaa   4320
actcacgtta agggattttg gtcatgagat tatcaaaaag gatcttcacc tagatccttt   4380
taaattaaaa atgaagtttt aaatcaatct aaagtatata tgagtaaact tggtctgaca   4440
gttaccaatg cttaatcagt gaggcaccta tctcagcgat ctgtctattt cgttcatcca   4500
tagttgcctg actccccgtc gtgtagataa ctacgatacg ggagggctta ccatctggcc   4560
ccagtgctgc aatgataccg cgagacccac gctcaccggc tccagattta tcagcaataa   4620
accagccagc cggaagggcc gagcgcagaa gtggtcctgc aactttatcc gcctccatcc   4680
agtctattaa ttgttgccgg gaagctagag taagtagttc gccagttaat agtttgcgca   4740
acgttgttgc cattgctgca ggcatcgtgg tgtcacgctc gtcgtttggt atggcttcat   4800
tcagctccgg ttcccaacga tcaaggcgag ttacatgatc ccccatgttg tgcaaaaaag   4860
cggttagctc cttcggtcct ccgatcgttg tcagaagtaa gttggccgca gtgttatcac   4920
tcatggttat ggcagcactg cataattctc ttactgtcat gccatccgta agatgctttt   4980
ctgtgactgg tgagtactca accaagtcat tctgagaata gtgtatgcgg cgaccgagtt   5040
gctcttgccc ggcgtcaata cgggataata ccgcgccaca tagcagaact ttaaaagtgc   5100
tcatcattgg aaaacgttct tcggggcgaa aactctcaag gatcttaccg ctgttgagat   5160
ccagttcgat gtaacccact cgtgcaccca actgatcttc agcatctttt actttcacca   5220
gcgtttctgg gtgagcaaaa acaggaaggc aaaatgccgc aaaaaaggga ataagggcga   5280
cacggaaatg ttgaatactc atactcttcc tttttcaata ttattgaagc atttatcagg   5340
gttattgtct catgagcgga tacatatttg aatgtattta gaaaaataaa caaatagggg   5400
```

```
ttccgcgcac atttccccga aaagtgccac ctgaaattgt aaacgttaat attttgttaa   5460

aattcgcgtt aaatttttgt taaatcagct cattttttaa ccaataggcc gaaatcggca   5520

aaatccctta taaatcaaaa gaatagaccg agatagggtt gagtgttgtt ccagtttgga   5580

acaagagtcc actattaaag aacgtggact ccaacgtcaa agggcgaaaa accgtctatc   5640

agggcgatgg cccactacgt gaaccatcac cctaatcaag ttttttgggg tcgaggtgcc   5700

gtaaagcact aaatcggaac cctaaaggga gcccccgatt tagagcttga cggggaaagc   5760

cggcgaacgt ggcgagaaag gaagggaaga aagcgaaagg agcgggcgct agggcgctgg   5820

caagtgtagc ggtcacgctg cgcgtaacca ccacacccgc cgcgcttaat gcgccgctac   5880

agggcgcgtc ccattcgcca                                               5900
```

```
<210> SEQ ID NO 7
<211> LENGTH: 271
<212> TYPE: PRT
<213> ORGANISM: Artificial Sequence
<220> FEATURE:
<223> OTHER INFORMATION: Kanamycin resistance marker

<400> SEQUENCE: 7

Met Ser His Ile Gln Arg Glu Thr Ser Cys Ser Arg Pro Arg Leu Asn
1               5                   10                  15

Ser Asn Met Asp Ala Asp Leu Tyr Gly Tyr Lys Trp Ala Arg Asp Asn
            20                  25                  30

Val Gly Gln Ser Gly Ala Thr Ile Tyr Arg Leu Tyr Gly Lys Pro Asp
        35                  40                  45

Ala Pro Glu Leu Phe Leu Lys His Gly Lys Gly Ser Val Ala Asn Asp
    50                  55                  60

Val Thr Asp Glu Met Val Arg Leu Asn Trp Leu Thr Glu Phe Met Pro
65                  70                  75                  80

Leu Pro Thr Ile Lys His Phe Ile Arg Thr Pro Asp Asp Ala Trp Leu
                85                  90                  95

Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125

Arg Arg Leu His Ser Ile Pro Val Cys Asn Cys Pro Phe Asn Ser Asp
    130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175

Gln Val Trp Lys Glu Met His Lys Leu Leu Pro Phe Ser Pro Asp Ser
            180                 185                 190

Val Val Thr His Gly Asp Phe Ser Leu Asp Asn Leu Ile Phe Asp Glu
        195                 200                 205

Gly Lys Leu Ile Gly Cys Ile Asp Val Gly Arg Val Gly Ile Ala Asp
    210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
            260                 265                 270
```

<210> SEQ ID NO 8
<211> LENGTH: 286
<212> TYPE: PRT
<213> ORGANISM: Artificial Sequence
<220> FEATURE:
<223> OTHER INFORMATION: Ampicillin resistance marker

<400> SEQUENCE: 8

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```

<210> SEQ ID NO 9
<211> LENGTH: 123
<212> TYPE: PRT
<213> ORGANISM: Artificial Sequence
<220> FEATURE:
<223> OTHER INFORMATION: Zeocin resistance marker

<400> SEQUENCE: 9

```
Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30
```

```
Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln
        115                 120


<210> SEQ ID NO 10
<211> LENGTH: 219
<212> TYPE: PRT
<213> ORGANISM: Artificial Sequence
<220> FEATURE:
<223> OTHER INFORMATION: Chloramphenicol resistance marker

<400> SEQUENCE: 10

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215


<210> SEQ ID NO 11
<211> LENGTH: 396
<212> TYPE: PRT
<213> ORGANISM: Artificial Sequence
<220> FEATURE:
<223> OTHER INFORMATION: Tetracyclin resistance marker
```

<400> SEQUENCE: 11

```
Met Lys Ser Asn Asn Ala Leu Ile Val Ile Leu Gly Thr Val Thr Leu
1               5                   10                  15

Asp Ala Val Gly Ile Gly Leu Val Met Pro Val Leu Pro Gly Leu Leu
            20                  25                  30

Arg Asp Ile Val His Ser Asp Ser Ile Ala Ser His Tyr Gly Val Leu
        35                  40                  45

Leu Ala Leu Tyr Ala Leu Met Gln Phe Leu Cys Ala Pro Val Leu Gly
    50                  55                  60

Ala Leu Ser Asp Arg Phe Gly Arg Arg Pro Val Leu Leu Ala Ser Leu
65                  70                  75                  80

Leu Gly Ala Thr Ile Asp Tyr Ala Ile Met Ala Thr Thr Pro Val Leu
                85                  90                  95

Trp Ile Leu Tyr Ala Gly Arg Ile Val Ala Gly Ile Thr Gly Ala Thr
            100                 105                 110

Gly Ala Val Ala Gly Ala Tyr Ile Ala Asp Ile Thr Asp Gly Glu Asp
        115                 120                 125

Arg Ala Arg His Phe Gly Leu Met Ser Ala Cys Phe Gly Val Gly Met
    130                 135                 140

Val Ala Gly Pro Val Ala Gly Gly Leu Leu Gly Ala Ile Ser Leu His
145                 150                 155                 160

Ala Pro Phe Leu Ala Ala Ala Val Leu Asn Gly Leu Asn Leu Leu Leu
                165                 170                 175

Gly Cys Phe Leu Met Gln Glu Ser His Lys Gly Glu Arg Arg Pro Met
            180                 185                 190

Pro Leu Arg Ala Phe Asn Pro Val Ser Ser Phe Arg Trp Ala Arg Gly
        195                 200                 205

Met Thr Ile Val Ala Ala Leu Met Thr Val Phe Phe Ile Met Gln Leu
    210                 215                 220

Val Gly Gln Val Pro Ala Ala Leu Trp Val Ile Phe Gly Glu Asp Arg
225                 230                 235                 240

Phe Arg Trp Ser Ala Thr Met Ile Gly Leu Ser Leu Ala Val Phe Gly
                245                 250                 255

Ile Leu His Ala Leu Ala Gln Ala Phe Val Thr Gly Pro Ala Thr Lys
            260                 265                 270

Arg Phe Gly Glu Lys Gln Ala Ile Ile Ala Gly Met Ala Ala Asp Ala
        275                 280                 285

Leu Gly Tyr Val Leu Leu Ala Phe Ala Thr Arg Gly Trp Met Ala Phe
    290                 295                 300

Pro Ile Met Ile Leu Leu Ala Ser Gly Gly Ile Gly Met Pro Ala Leu
305                 310                 315                 320

Gln Ala Met Leu Ser Arg Gln Val Asp Asp Asp His Gln Gly Gln Leu
                325                 330                 335

Gln Gly Ser Leu Ala Ala Leu Thr Ser Leu Thr Ser Ile Thr Gly Pro
            340                 345                 350

Leu Ile Val Thr Ala Ile Tyr Ala Ala Ser Ala Ser Thr Trp Asn Gly
        355                 360                 365

Leu Ala Trp Ile Val Gly Ala Ala Leu Tyr Leu Val Cys Leu Pro Ala
    370                 375                 380

Leu Arg Arg Gly Ala Trp Ser Arg Ala Thr Ser Thr
385                 390                 395
```

<210> SEQ ID NO 12

```
<211> LENGTH: 263
<212> TYPE: PRT
<213> ORGANISM: Artificial Sequence
<220> FEATURE:
<223> OTHER INFORMATION: Streptomycin resistance marker

<400> SEQUENCE: 12

Met Arg Glu Ala Val Ile Ala Glu Val Ser Thr Gln Leu Ser Glu Val
1               5                   10                  15

Val Gly Val Ile Glu Arg His Leu Glu Pro Thr Leu Leu Ala Val His
            20                  25                  30

Leu Tyr Gly Ser Ala Val Asp Gly Gly Leu Lys Pro His Ser Asp Ile
        35                  40                  45

Asp Leu Leu Val Thr Val Thr Val Arg Leu Asp Glu Thr Thr Arg Arg
    50                  55                  60

Ala Leu Ile Asn Asp Leu Leu Glu Thr Ser Ala Ser Pro Gly Glu Ser
65                  70                  75                  80

Glu Ile Leu Arg Ala Val Glu Val Thr Ile Val Val His Asp Asp Ile
                85                  90                  95

Ile Pro Trp Arg Tyr Pro Ala Lys Arg Glu Leu Gln Phe Gly Glu Trp
            100                 105                 110

Gln Arg Asn Asp Ile Leu Ala Gly Ile Phe Glu Pro Ala Thr Ile Asp
        115                 120                 125

Ile Asp Leu Ala Ile Leu Leu Thr Lys Ala Arg Glu His Ser Val Ala
    130                 135                 140

Leu Val Gly Pro Ala Ala Glu Glu Leu Phe Asp Pro Val Pro Glu Gln
145                 150                 155                 160

Asp Leu Phe Glu Ala Leu Asn Glu Thr Leu Thr Leu Trp Asn Ser Pro
                165                 170                 175

Pro Asp Trp Ala Gly Asp Glu Arg Asn Val Val Leu Thr Leu Ser Arg
            180                 185                 190

Ile Trp Tyr Ser Ala Val Thr Gly Lys Ile Ala Pro Lys Asp Val Ala
        195                 200                 205

Ala Asp Trp Ala Met Glu Arg Leu Pro Ala Gln Tyr Gln Pro Val Ile
    210                 215                 220

Leu Glu Ala Arg Gln Ala Tyr Leu Gly Gln Glu Glu Asp Arg Leu Ala
225                 230                 235                 240

Ser Arg Ala Asp Gln Leu Glu Glu Phe Val His Tyr Val Lys Gly Glu
                245                 250                 255

Ile Thr Lys Val Val Gly Lys
            260


<210> SEQ ID NO 13
<211> LENGTH: 116
<212> TYPE: PRT
<213> ORGANISM: Artificial Sequence
<220> FEATURE:
<223> OTHER INFORMATION: LacZ alpha marker

<400> SEQUENCE: 13

Met Thr Met Ile Thr Pro Ser Leu His Ala Cys Arg Phe Lys Gln Ser
1               5                   10                  15

Thr Leu Asp Leu Ile Lys Asp Pro Ala Arg Pro Arg Val Pro Ser Ser
            20                  25                  30

Asn Ser Leu Ala Val Val Leu Gln Arg Arg Asp Trp Glu Asn Pro Gly
        35                  40                  45

Val Thr Gln Leu Asn Arg Leu Ala Ala His Pro Pro Phe Ala Ser Trp
```

```
    50                  55                  60

Arg Asn Ser Glu Glu Ala Arg Thr Asp Arg Pro Ser Gln Gln Leu Arg
65                  70                  75                  80

Ser Leu Asn Gly Glu Trp Arg Leu Met Arg Tyr Phe Leu Leu Thr His
                85                  90                  95

Leu Cys Gly Ile Ser His Arg Ile Trp Cys Thr Leu Ser Thr Ile Cys
            100                 105                 110

Ser Asp Ala Ala
        115


<210> SEQ ID NO 14
<211> LENGTH: 819
<212> TYPE: DNA
<213> ORGANISM: Artificial Sequence
<220> FEATURE:
<223> OTHER INFORMATION: Kanamycin resistance marker

<400> SEQUENCE: 14

atgagccata ttcaaacgcg tgaaacgtct tgctctaggc cgcgattaaa ttccaacatg     60

gatgctgatt tatatgggta taaatgggct cgcgataatg tcgggcaatc aggtgcgaca    120

atctatcgat tgtatgggaa gcccgatgcg ccagagttgt ttctgaaaca tggcaaaggt    180

agcgttgcca atgatgttac agatgagatg gtcagactaa actggctgac ggaatttatg    240

cctcttccga ccatcaagca ttttatccgt actcctgatg acgcgtggtt actcaccact    300

gcgatccctg ggaaaacagc attccaggta ttagaagaat atcctgattc aggtgaaaat    360

attgttgatg cgctggcagt gttcctgcgc cggttgcatt cgattcctgt ttgtaattgt    420

ccttttaaca gcgatcgcgt atttcgtctc gctcaggcgc aatcacgaat gaataacggt    480

ttggttgacg cgtcagattt tgatgacgag cgtaatggct ggcctgttga acaagtctgg    540

aaagaaatgc ataaactttt gccattctca ccggattcag tcgtcactca tggtgatttc    600

tcacttgata accttatttt tgacgagggg aaattaatag gttgtattga tgttggacgc    660

gtcggaatcg cagaccgata ccaggatctt gccatcctat ggaactgcct cggtgagttt    720

tctccttcat tacagaaacg gctttttcaa aaatatggta ttgataatcc tgatatgaat    780

aaattgcagt ttcatttgat gctcgatgag tttttctaa                           819


<210> SEQ ID NO 15
<211> LENGTH: 861
<212> TYPE: DNA
<213> ORGANISM: Artificial Sequence
<220> FEATURE:
<223> OTHER INFORMATION: Ampicillin resistance marker

<400> SEQUENCE: 15

atgagcatcc agcatttccg tgtcgccctt attccctttt ttgcggcatt ttgccttcct     60

gtttttgctc acccagaaac gctggtgaaa gtaaaagatg ctgaagatca gttgggagca    120

cgcgtgggtt acatcgaact ggatctcaac agcggtaaga tccttgagag ttttcgcccc    180

gaagaacgtt ttccaatgat gagcactttt aaagttctgc tatgtggcgc ggtattatcc    240

cgtattgacg ccgggcaaga gcaactcggt cgccgcatac actattctca gaatgacttg    300

gttgagtact caccagtcac agaaaagcat cttacggatg gcatgacagt aagagaatta    360

tgcagtgctg ccataaccat gagtgataac actgcggcca acttacttct gacaacgatc    420

ggaggaccga aggagctaac cgcttttttg cacaacatgg gggatcatgt aacgcgtctt    480

gatcgttggg aaccggagct gaatgaagcc ataccaaacg acgagcgtga caccacgatg    540
```

```
cctgtagcaa tggcaacaac gttgcgcaaa ctattaactg gcgaactact tactctagct    600

tcccggcaac aattaataga ctggatggag gcggataaag ttgcaggacc acgtatacgc    660

tcggcccttc cggctggctg gtttattgct gataaatctg gagccggtga gcgtgggtct    720

cgcggtatca ttgcagcact ggggccagat ggtaagccct cccgtatcgt agttatctac    780

acgacgggga gtcaggcaac tatggatgaa cgaaatagac agatcgctga gataggtgcc    840

tcactgatta agcattggta a                                             861
```

<210> SEQ ID NO 16
<211> LENGTH: 375
<212> TYPE: DNA
<213> ORGANISM: Artificial Sequence
<220> FEATURE:
<223> OTHER INFORMATION: Zeocin resistance marker

<400> SEQUENCE: 16

```
atggccaagt tgaccagtgc cgttccggtg ctcaccgcgc gcgacgtcgc cggagcggtc     60

gagttctgga ccgaccggct cgggttctcc cgggacttcg tggaggacga cttcgccggt    120

atacatcggg acgacgtgac cctgttcatc agcgcggtcc aggaccaggt ggtgccggac    180

aacaccctgg cctgggtgtg ggtgcgcggc ctggacgagc tgtacgccga gtggtcggag    240

gtcgtgtcca cgaacttccg ggacgcgtcc gggccggcca tgaccgagat cggcgagcag    300

ccgtgggggc gggagttcgc cctgcgcgac ccggccggca actgcgtgca cttcgtggcc    360

gaggagcagg actga                                                     375
```

<210> SEQ ID NO 17
<211> LENGTH: 660
<212> TYPE: DNA
<213> ORGANISM: Artificial Sequence
<220> FEATURE:
<223> OTHER INFORMATION: Chloramphenicol resistance marker

<400> SEQUENCE: 17

```
atggagaaaa aaatcactgg gtataccacc gttgatatat cccaatggca tcgtaaagaa     60

cattttgagg catttcagtc agttgctcaa tgtacctata accagaccgt tcagctggat    120

attacggcct ttttaaagac cgtaaagaaa aataagcaca agttttatcc ggcctttatt    180

cacattcttg cccgcctgat gaatgctcat ccggaatttc gtatggcaat gaaagacggt    240

gagctggtga tatgggatag tgttcaccct tgttataccg ttttccatga gcaaactgaa    300

acgttttcat cgctctggag tgaataccac gacgatttcc ggcagtttct acacatatat    360

tcgcaagatg tggcgtgtta cggtgaaaac ctggcctatt tccctaaagg gtttattgag    420

aatatgtttt tcgtctcagc caatccctgg gtgagtttca ccagttttga tttaaacgta    480

tacaatatgg acaacttctt cgcccccgtt ttcaccatgg gcaaatatta tacgcaaggc    540

gacaaggtgc tgatgccgct ggcgattcag gttcatcatg ccgtttgtga tggcttccat    600

gtcggcagaa tgcttaatga attacaacag tactgcgatg agtggcaggg cggggcgtaa    660
```

<210> SEQ ID NO 18
<211> LENGTH: 351
<212> TYPE: DNA
<213> ORGANISM: Artificial Sequence
<220> FEATURE:
<223> OTHER INFORMATION: LacZ alpha marker

<400> SEQUENCE: 18

```
atgaccatga ttacgccaag cttgcatgcc tgcaggttta aacagtcgac tctagactta      60

attaaggatc cggcgcgccc acgcgtaccg agctcgaatt cactggccgt cgttttacaa     120

cgtcgtgact gggaaaaccc tggcgttacc caacttaatc gccttgcagc acatccccct     180

ttcgccagct ggcgtaatag cgaagaggcc cgcaccgatc gcccttccca acagttgcgc     240

agcctgaatg gcgaatggcg cctgatgcgg tattttctcc ttacgcatct gtgcggtatt     300

tcacaccgca tatggtgcac tctcagtaca atctgctctg atgccgcata g              351
```

```
<210> SEQ ID NO 19
<211> LENGTH: 45
<212> TYPE: DNA
<213> ORGANISM: Artificial Sequence
<220> FEATURE:
<223> OTHER INFORMATION: MCS

<400> SEQUENCE: 19

acgcgtcctg cagggcggcc gcgtcgacgc gcgcacatgt gtata                      45
```

```
<210> SEQ ID NO 20
<211> LENGTH: 674
<212> TYPE: DNA
<213> ORGANISM: Artificial Sequence
<220> FEATURE:
<223> OTHER INFORMATION: Ori

<400> SEQUENCE: 20

atgtgagcaa aaggccagca aaaggccagg aaccgtaaaa aggccgcgtt gctggcgttt      60

ttccataggc tccgcccccc tgacgagcat cacaaaaatc gacgctcaag tcagaggtgg     120

cgaaacccga caggactata aagataccag gcgtttcccc ctggaagctc cctcgtgcgc     180

tctcctgttc cgaccctgcc gcttaccgga tacctgtccg cctttctccc ttcgggaagc     240

gtggcgcttt ctcatagctc acgctgtagg tatctcagtt cggtgtaggt cgttcgctcc     300

aagctgggct gtgtgcacga accccccgtt cagcccgacc gctgcgcctt atccggtaac     360

tatcgtcttg agtccaaccc ggtaagacac gacttatcgc cactggcagc agccactggt     420

aacaggatta gcagagcgag gtatgtaggc ggtgctacag agttcttgaa gtggtggcct     480

aactacggct acactagaag aacagtattt ggtatctgcg ctctgctgaa gccagttacc     540

ttcggaaaaa gagttggtag ctcttgatcc ggcaaacaaa ccaccgctgg tagcggtggt     600

tttttgttt gcaagcagca gattacgcgc agaaaaaaag gatctcaaga agatcctttg      660

atcttttcta cggg                                                       674
```

```
<210> SEQ ID NO 21
<211> LENGTH: 675
<212> TYPE: DNA
<213> ORGANISM: Artificial Sequence
<220> FEATURE:
<223> OTHER INFORMATION: Ori

<400> SEQUENCE: 21

cccgtagaaa agatcaaagg atcttcttga gatccttttt ttctgcgcgt aatctgctgc      60

ttgcaaacaa aaaaaccacc gctaccagcg gtggtttgtt tgccggatca agagctacca     120

actctttttc cgaaggtaac tggcttcagc agagcgcaga taccaaatac tgttcttcta     180

gtgtagccgt agttaggcca ccacttcaag aactctgtag caccgcctac atacctcgct     240

ctgctaatcc tgttaccagt ggctgctgcc agtggcgata agtcgtgtct taccgggttg     300

gactcaagac gatagttacc ggataaggcg cagcggtcgg gctgaacggg gggttcgtgc     360
```

```
acacagccca gcttggagcg aacgacctac accgaactga gatacctaca gcgtgagcta    420

tgagaaagcg ccacgcttcc cgaagggaga aaggcggaca ggtatccggt aagcggcagg    480

gtcggaacag gagagcgcac gagggagctt ccagggggaa acgcctggta tctttatagt    540

cctgtcgggt ttcgccacct ctgacttgag cgtcgatttt tgtgatgctc gtcagggggg    600

cggagcctat ggaaaaacgc cagcaacgcg gcctttttac ggttcctggc cttttgctgg    660

ccttttgctc acatg                                                      675
```

<210> SEQ ID NO 22
<211> LENGTH: 675
<212> TYPE: DNA
<213> ORGANISM: Artificial Sequence
<220> FEATURE:
<223> OTHER INFORMATION: Ori

<400> SEQUENCE: 22

```
cccgtagaaa agatcaaagg atcttcttga gatccttttt ttctgcgcgt aatctgctgc     60

ttgcaaacaa aaaaaccacc gctaccagcg gtggtttgtt tgccggatca agagctacca    120

actctttttc cgaaggtaac tggcttcagc agagcgcaga taccaaatac tgtccttcta    180

gtgtagccgt agttaggcca ccacttcaag aactctgtag caccgcctac atacctcgct    240

ctgctaatcc tgttaccagt ggctgctgcc agtggcgata agtcgtgtct taccgggttg    300

gactcaagac gatagttacc ggataaggcg cagcggtcgg gctgaacggg gggttcgtgc    360

acacagccca gcttggagcg aacgacctac accgaactga gatacctaca gcgtgagcta    420

tgagaaagcg ccacgcttcc cgaagggaga aaggcggaca ggtatccggt aagcggcagg    480

gtcggaacag gagagcgcac gagggagctt ccagggggaa acgcctggta tctttatagt    540

cctgtcgggt ttcgccacct ctgacttgag cgtcgatttt tgtgatgctc gtcagggggg    600

cggagcctat ggaaaaacgc cagcaacgcg gcctttttac ggttcctggc cttttgctgg    660

ccttttgctc acatg                                                      675
```

<210> SEQ ID NO 23
<211> LENGTH: 676
<212> TYPE: DNA
<213> ORGANISM: Artificial Sequence
<220> FEATURE:
<223> OTHER INFORMATION: Ori

<400> SEQUENCE: 23

```
tcagtagaaa agattaaagg atcttcttga gatccttttt ttctgcgcgt aatctgctgc     60

ttgcaaacaa aaaaaccacc gctaccaacg gtggtttgtt tgccggatca agagctacca    120

actctttttc cgaaggtaac tggcttcagc agagcgcaga taccaaatac tgtccttcta    180

gtgtagccgt agtcgggcca ctacttcaag aactctgtag caccgtttgt gccatcatcg    240

ctctgctaat ccggttacca gtggctgctg ccagtggcgt taaggcgtgc cttaccgggt    300

tggactcaag acgatagtta ccggataagg cgcagcggtc gggctgaacg gggggttcgt    360

gcacacagcc cagcttggag cgaacgacct acaccgaact gagataccaa cagcgtgagc    420

tatgagaaag cgccacgctt cccgaaggga gaaaggcgga caggtatccg gtaagcggca    480

gggtcggaac aggagagcgc acgagggagc ttccaggggg aaacgcctgg tagctttata    540

gtcctgtcgg gtttcgccac ctctgacttg agcgtctatt tttgtgatgc tcgtcagggg    600

ggcggagcct atggaaaaac gcctgctacg tggccttctt cctgttcctg gtcttttgct    660
```

cacatgttct ttccgg 676

<210> SEQ ID NO 24
<211> LENGTH: 282
<212> TYPE: DNA
<213> ORGANISM: Artificial Sequence
<220> FEATURE:
<223> OTHER INFORMATION: Ori

<400> SEQUENCE: 24
aagctttaaa agccttatat attctttttt ttcttataaa acttaaaacc ttagaggcta 60
tttaagttgc tgatttatat taattttatt gttcaaacat gagagcttag tacgtgaaac 120
atgagagctt agtacgttag ccatgagagc ttagtacgtt agccatgagg gtttagttcg 180
ttaaacatga gagcttagta cgttaaacat gagagcttag tacgtgaaac atgagagctt 240
agtacgtact atcaacaggt tgaactgctg atcttcagat ct 282

<210> SEQ ID NO 25
<211> LENGTH: 830
<212> TYPE: DNA
<213> ORGANISM: Artificial Sequence
<220> FEATURE:
<223> OTHER INFORMATION: Ori

<400> SEQUENCE: 25
ttaataagat gatcttcttg agatcgtttt ggtctgcgcg taatctcttg ctctgaaaac 60
gaaaaaaccg ccttgcaggg cggtttttcg aaggttctct gagctaccaa ctctttgaac 120
cgaggtaact ggcttggagg agcgcagtca ccaaaacttg tcctttcagt ttagccttaa 180
ccggcgcatg acttcaagac taactcctct aaatcaatta ccagtggctg ctgccagtgg 240
tgcttttgca tgtctttccg ggttggactc aagacgatag ttaccggata aggcgcagcg 300
gtcggactga acggggggtt cgtgcataca gtccagcttg gagcgaactg cctacccgga 360
actgagtgtc aggcgtggaa tgagacaaac gcggccataa cagcggaatg acaccggtaa 420
accgaaaggc aggaacagga gagcgcacga gggagccgcc agggggaaac gcctggtatc 480
tttatagtcc tgtcgggttt cgccaccact gatttgagcg tcagatttcg tgatgcttgt 540
caggggggcg gagcctatgg aaaaacggct ttgccgcggc cctctcactt ccctgttaag 600
tatcttcctg gcatcttcca ggaaatctcc gccccgttcg taagccattt ccgctcgccg 660
cagtcgaacg accgagcgta gcgagtcagt gagcgaggaa gcggaatata tcctgtatca 720
catattctgc tgacgcaccg gtgcagcctt ttttctcctg ccacatgaag cacttcactg 780
acaccctcat cagtgccaac atagtaagcc agtatacact ccgctagcgc 830

<210> SEQ ID NO 26
<211> LENGTH: 510
<212> TYPE: DNA
<213> ORGANISM: Artificial Sequence
<220> FEATURE:
<223> OTHER INFORMATION: Ori

<400> SEQUENCE: 26
ggcgcctgta gtgccattta cccccattca ctgccagagc cgtgagcgca gcgaactgaa 60
tgtcacgaaa aagacagcga ctcaggtgcc tgatggtcgg agacaaaagg aatattcagc 120
gatttgcccg agcttgcgag ggtgctactt aagcctttag ggttttaagg tctgttttgt 180
agaggagcaa acagcgtttg cgacatcctt ttgtaatact gcggaactga ctaaagtagt 240
gagttataca cagggctggg atctattctt tttatctttt tttattcttt ctttattcta 300

```
taaattataa ccacttgaat ataaacaaaa aaaacacaca aaggtctagc ggaatttaca    360

gagggtctag cagaatttac aagttttcca gcaaaggtct agcagaattt acagataccc    420

acaactcaaa ggaaaaggac tagtaattat cattgactag cccatctcaa ttggtatagt    480

gattaaaatc acctagacca attgagatgt                                     510
```

<210> SEQ ID NO 27
<211> LENGTH: 676
<212> TYPE: DNA
<213> ORGANISM: Artificial Sequence
<220> FEATURE:
<223> OTHER INFORMATION: Ori

<400> SEQUENCE: 27

```
atgtgagcaa aaggccagca aaaggccagg aaccgtaaaa aggccgcgtt gctggcgttt     60

ttccataggc tccgcccccc tgacgacgca tcacaaaaat cgacgcgtca agtcagaggt    120

ggcgaaaccc gacaggacta taaagatacc aggcgtttcc ccctggaagc tccctcgtgc    180

gctctcctgt tccgaccctg ccgcttaccg gatacctgtc cgcctttctc ccttcgggaa    240

gcgtggcgct ttctcatagc tcacgctgta ggtatctcag ttcggtgtag gtcgttcgct    300

ccaagctggg ctgtgtgcac gaaccccccg ttcagcccga ccgctgcgcc ttatccggta    360

actatcgtct tgagtccaac ccggtaagac acgacttatc gccactggca gcagccactg    420

gtaacaggat tagcagagcg aggtatacag gcggtgctac agagttcttg aagtggtggc    480

ctaactacgg ctacactaga agaacagtat ttggtatctg cgctctgctg aagccagtta    540

ccttcggaaa aagagttggt agctcttgat ccggcaaaca aaccaccgct ggtagcggtg    600

gtttttttgt ttgcaagcag cagattacgc gcagaaaaaa aggatctcaa gaagatcctt    660

tgatcttttc tacggg                                                    676
```

<210> SEQ ID NO 28
<211> LENGTH: 676
<212> TYPE: DNA
<213> ORGANISM: Artificial Sequence
<220> FEATURE:
<223> OTHER INFORMATION: Ori

<400> SEQUENCE: 28

```
atgtgagcaa aaggccagca aaaggccagg aaccgtaaaa aggccgcgtt gctggcgttt     60

ttccataggc tccgcccccc tgacgacgca tcacaaaaat cgacgcgtca agtcagaggt    120

ggcgaaaccc gacaggacta taaagatacc aggcgtttcc ccctggaagc tccctcgtgc    180

gctctcctgt tccgaccctg ccgcttaccg gatacctgtc cgcctttctc ccttcgggaa    240

gcgtggcgct ttctcatagc tcacgctgta ggtatctcag ttcggtgtag gtcgttcgct    300

ccaagctggg ctgtgtatac gaaccccccg ttcagcccga ccgctgcgcc ttatccggta    360

actatcgtct tgagtccaac ccggtaagac acgacttatc gccactggca gcagccactg    420

gtaacaggat tagcagagcg aggtatgtag gcggtgctac agagttcttg aagtggtggc    480

ctaactacgg ctacactaga agaacagtat ttggtatctg cgctctgctg aagccagtta    540

ccttcggaaa aagagttggt agctcttgat ccggcaaaca aaccaccgct ggtagcggtg    600

gtttttttgt ttgcaagcag cagattacgc gcagaaaaaa aggatctcaa gaagatcctt    660

tgatcttttc tacggg                                                    676
```

<210> SEQ ID NO 29

<211> LENGTH: 676
<212> TYPE: DNA
<213> ORGANISM: Artificial Sequence
<220> FEATURE:
<223> OTHER INFORMATION: Ori

<400> SEQUENCE: 29
atgtgagcaa aaggccagca aaaggccagg aaccgtaaaa aggccgcgtt gctggcgttt 60
ttccataggc tccgcccccc tgacgacgca tcacaaaaat cgacgcgtca agtcagaggt 120
ggcgaaaccc gacaggacta taaagatacc aggcgtttcc ccctggaagc tccctcgtgc 180
gctctcctgt tccgaccctg ccgcttaccg gatacctgtc cgcctttctc ccttcgggaa 240
gcgtggcgct ttctcatagc tcacgctgta ggtataccag ttcggtgtag gtcgttcgct 300
ccaagctggg ctgtgtgcac gaaccccccg ttcagcccga ccgctgcgcc ttatccggta 360
actatcgtct tgagtccaac ccggtaagac acgacttatc gccactggca gcagccactg 420
gtaacaggat tagcagagcg aggtatgtag gcggtgctac agagttcttg aagtggtggc 480
ctaactacgg ctacactaga agaacagtat ttggtatctg cgctctgctg aagccagtta 540
ccttcggaaa aagagttggt agctcttgat ccggcaaaca aaccaccgct ggtagcggtg 600
gtttttttgt ttgcaagcag cagattacgc gcagaaaaaa aggatctcaa gaagatcctt 660
tgatcttttc tacggg 676

<210> SEQ ID NO 30
<211> LENGTH: 173
<212> TYPE: DNA
<213> ORGANISM: Artificial Sequence
<220> FEATURE:
<223> OTHER INFORMATION: TEE

<400> SEQUENCE: 30
caagctctag caggaagaag aaataagaag aagaagaaga agaagaagaa gcgtctcctc 60
ttcttcttgt gagagcaaaa aataaaactc ccaaaaaaaa gaaaatcatc aaaaaaacaa 120
atttcaaaaa gagtttttgt gtttggggat taaagaataa aaaaaacaac gtc 173

<210> SEQ ID NO 31
<211> LENGTH: 173
<212> TYPE: DNA
<213> ORGANISM: Artificial Sequence
<220> FEATURE:
<223> OTHER INFORMATION: TEE

<400> SEQUENCE: 31
caagctctag cacgtctcct cttcttcttg tgagagtaaa aaakaaaact cccaaaaaaa 60
akaaaatcat caaaaaaaca aatttcaaaa agagtttttg tgtttgggga ttaaagaaka 120
aaaaaaacaa ggaagaagaa akaagaagaa gaagaagaag aagaagaagc ctc 173

<210> SEQ ID NO 32
<211> LENGTH: 274
<212> TYPE: DNA
<213> ORGANISM: Artificial Sequence
<220> FEATURE:
<223> OTHER INFORMATION: TEE

<400> SEQUENCE: 32
caagctctag caggaagaag aaakaagaag aagaagaaga agaagaagaa gcgtctcctc 60
ttcttcttgt gagagtaaaa aakaaaactc ccaaaaaaaa kaaaatcatc aaaaaaacaa 120
atttcaaaaa gagtttttgt gtttggggat taaagaakaa aaaaaacaac aggtgagtaa 180
gcgcagttgt cgtctcttgc ggtgccgttg ctggttctca cacctttttag gtctgttctc 240 gtcttccgtt ctgactctct ctttttcgtt gcag 274

<210> SEQ ID NO 33
<211> LENGTH: 277
<212> TYPE: DNA
<213> ORGANISM: Artificial Sequence
<220> FEATURE:
<223> OTHER INFORMATION: TEE

<400> SEQUENCE: 33
caagctctag caggaagaag aaakaagaag aagaagaaga agaagaagaa gcgtctcctc 60
ttcttcttgt gagagtaaaa aakaaaactc ccaaaaaaaa gaaaatcatc aaaaaaacaa 120
atttcaaaaa gagtttttgt gtttggggat taaagaagaa aaaaaacaac aggtgagtaa 180
gcgcagttgt cgtctcttgc ggtgccgttg ctggttctca cacctttttag gtctgttctc 240 gtcttccgtt ctgactctct ctttttcgtt gcaggcc 277

<210> SEQ ID NO 34
<211> LENGTH: 278
<212> TYPE: DNA
<213> ORGANISM: Artificial Sequence
<220> FEATURE:
<223> OTHER INFORMATION: TEE

<400> SEQUENCE: 34
caagctctag caggaagaag aaagaagaag aagaagaaga agaagaagaa gcgtctcctc 60
ttcttcttgt gagagtaaaa aagaaaactc ccaaaaaaaa gaaaatcatc aaaaaaacaa 120
atttcaaaaa gagtttttgt gtttggggat taaaggtgag taagcgcagt tgtcgtctct 180
tgcggtgccg ttgctggttc tcacaccttt taggtctgtt ctcgtcttcc gttctgactc 240
tctctttttc gttgcagaac tcctaaaaaa ccgccacc 278

<210> SEQ ID NO 35
<211> LENGTH: 266
<212> TYPE: DNA
<213> ORGANISM: Artificial Sequence
<220> FEATURE:
<223> OTHER INFORMATION: TEE

<400> SEQUENCE: 35
caagctctag caggaagaag aaakaagaag aagaagaaga agaagaagaa gcgtctcctc 60
ttcttcttgt gagagtaaaa aakaaaactc ccaaaaaaaa gaaaatcatc aaaaaaacaa 120
atttcaaaaa gagtgaggta agattatcga tatttaaatt atttatttct tcttttccat 180 tttttggct aacattttcc atggttttat gatatcatgc aggtacgttt tgtgtttggg 240
gattaaagaa taaaaaaaac aaaaca 266

<210> SEQ ID NO 36
<211> LENGTH: 178
<212> TYPE: DNA
<213> ORGANISM: Artificial Sequence
<220> FEATURE:
<223> OTHER INFORMATION: TEE

<400> SEQUENCE: 36
cgtctcctct tcttcttgtg agagtaaaaa akaaaactcc caaaaaaaag aaaatcatca 60
aaaaaacaaa tttcaaaaag agtttttgtg tttggggatt aaagaakaaa aaaaacaacc 120
tcgtgcgtgt tgccgattcg cgtacgaata cgccttgtgc tgacacttct gtagcacc 178

<210> SEQ ID NO 37
<211> LENGTH: 86
<212> TYPE: DNA
<213> ORGANISM: Artificial Sequence
<220> FEATURE:
<223> OTHER INFORMATION: TEE

<400> SEQUENCE: 37
ttcaaaaaga gtttttgtgt ttggggatta aagaataaaa aaaacaagga agaagaaaka 60
agaagaagaa gaagaagaag aagaag 86

<210> SEQ ID NO 38
<211> LENGTH: 277
<212> TYPE: DNA
<213> ORGANISM: Artificial Sequence
<220> FEATURE:
<223> OTHER INFORMATION: TEE

<400> SEQUENCE: 38
caagctctag cacgtctcct cttcttcttg tgagagtaaa aaakaaaact cccaaaaaaa 60
agaaaatcat caaaaaaaca aatttcaaaa agagtttttg tgtttgggga ttaaagaaga 120
aaaaaaacaa ggaagaagaa akaagaagaa gaagaagaag aagaagaagc aggtgagtaa 180
gcgcagttgt cgtctcttgc ggtgccgttg ctggttctca caccttttag gtctgttctc 240
gtcttccgtt ctgactctct ctttttcgtt gcaggcc 277

<210> SEQ ID NO 39
<211> LENGTH: 265
<212> TYPE: DNA
<213> ORGANISM: Artificial Sequence
<220> FEATURE:
<223> OTHER INFORMATION: TEE

<400> SEQUENCE: 39
caagctctag cacgtctcct cttcttcttg tgagagtaaa aaakaaaact cccaaaaaaa 60
agaaaatcat caaaaaaaca aatttcaaaa agagtgaggt aagattatcg atatttaaat 120
tatttatttc ttcttttcca ttttttggc taacattttc ctaggtttta ttatatctag 180
caggtacgtt ttgtgtttgg ggattaaaga agaaaaaaaa caaggaagaa gaaakaagaa 240
gaagaagaag aagaagaaga aaaca 265

<210> SEQ ID NO 40
<211> LENGTH: 188
<212> TYPE: DNA
<213> ORGANISM: Artificial Sequence
<220> FEATURE:
<223> OTHER INFORMATION: TEE

<400> SEQUENCE: 40
caasctctac caccaasaac aaacaacaac aacatataya aaacaacaac maccatctcc 60
tcttcttctt gtcaastmma aaaycaaact cccaaaaaaa agmaaatcat caaaammaca 120
aatttcaaam aacaacawya aacaacaaam aamattaaca tcatatcaag gcggccgccc 180
ccttcacc 188

<210> SEQ ID NO 41
<211> LENGTH: 173
<212> TYPE: DNA
<213> ORGANISM: Artificial Sequence

<220> FEATURE:
<223> OTHER INFORMATION: TEE

<400> SEQUENCE: 41
caagctctag caggaagaag aaataagaag aagaagaaga agaagaagaa gcgtctcctc 60
ttcttcttgt gagagtaaaa aataaaactc ccaaaaaaaa gaaaatcatc aaaaaaacaa 120
atttcaaaaa gagtttttgt gtttggggat taaagaataa aaaaaacaac gtc 173

<210> SEQ ID NO 42
<211> LENGTH: 175
<212> TYPE: DNA
<213> ORGANISM: Artificial Sequence
<220> FEATURE:
<223> OTHER INFORMATION: TEE

<400> SEQUENCE: 42
caagctctag caggaagaag aaataagaag aagaagaaga agaagaagaa gcgtctcctc 60
ttcttcttgt gagagtaaaa aataaaactc ccaaaaaaaa gaaaatcatc aaaaaaacaa 120
atttcaaaaa gagtttttgt gtttggggat taaagaataa aaaaaacaac gtccc 175

<210> SEQ ID NO 43
<211> LENGTH: 189
<212> TYPE: DNA
<213> ORGANISM: Artificial Sequence
<220> FEATURE:
<223> OTHER INFORMATION: TEE

<400> SEQUENCE: 43
agatcactag aagcttcaag ctctagcagg aagaagaaat aagaagaaga agaagaagaa 60
gaagaagcgt ctcctcttct tcttgtgaga gtaaaaaata aaactcccaa aaaaaagaaa 120
atcatcaaaa aaacaaattt caaaaagagt ttttgtgttt ggggattaaa gaataaaaaa 180
aacaacgcc 189

<210> SEQ ID NO 44
<211> LENGTH: 189
<212> TYPE: DNA
<213> ORGANISM: Artificial Sequence
<220> FEATURE:
<223> OTHER INFORMATION: TEE

<400> SEQUENCE: 44
agatcactag aagcttcaag ctctagcagg aagaagaaag aagaagaaga agaagaagaa 60
gaagaagcgt ctcctcttct tcttgtgaga gtaaaaaaga aaactcccaa aaaaaagaaa 120
atcatcaaaa aaacaaattt caaaaagagt ttttgtgttt ggggattaaa gaagaaaaaa 180
aacaacgcc 189

<210> SEQ ID NO 45
<211> LENGTH: 191
<212> TYPE: DNA
<213> ORGANISM: Artificial Sequence
<220> FEATURE:
<223> OTHER INFORMATION: TEE

<400> SEQUENCE: 45
agatcactag aagcttcaag ctctagcagg aagaagaaat aagaagaaga agaagaagaa 60
gaagaagcgt ctcctcttct tcttgtgaga gtaaaaaata aaactcccaa aaaaaagaaa 120
atcatcaaaa aaacaaattt caaaaagagt ttttgtgttt ggggattaaa gaataaaaaa 180
aacaacaggc c 191

<210> SEQ ID NO 46
<211> LENGTH: 284
<212> TYPE: DNA
<213> ORGANISM: Artificial Sequence
<220> FEATURE:
<223> OTHER INFORMATION: TEE

<400> SEQUENCE: 46 cttttcgca acgggtttgc cgccagaaca caggtgtcgt gaggaattag cttggtacta 60
atacgactca ctatagggag acccaagctg gctaggtaag cttggtaccc aagctctagc 120
aggaagaaga aataagaaga agaagaagaa gaagaagaag cgtctcctct tcttcttgtg 180
agagtaaaaa ataaaactcc caaaaaaaag aaaatcatca aaaaaacaaa tttcaaaaag 240
agtttttgtg tttggggatt aaagaataaa aaaaacaacg tccc 284

<210> SEQ ID NO 47
<211> LENGTH: 230
<212> TYPE: DNA
<213> ORGANISM: Artificial Sequence
<220> FEATURE:
<223> OTHER INFORMATION: TEE

<400> SEQUENCE: 47
aacccactgc ttactggctt atcgaaatta atacgactca ctatagggag acccaagctc 60
tagcaggaag aagaaataag aagaagaaga agaagaagaa gaagcgtctc ctcttcttct 120
tgtgagagta aaaaataaaa ctcccaaaaa aaagaaaatc atcaaaaaaa caaatttcaa 180
aaagagtttt tgtgtttggg gattaaagaa taaaaaaaac aacctccacc 230

<210> SEQ ID NO 48
<211> LENGTH: 177
<212> TYPE: DNA
<213> ORGANISM: Artificial Sequence
<220> FEATURE:
<223> OTHER INFORMATION: TEE

<400> SEQUENCE: 48
caagctctag cagcaacaac aaataacaac aacaacaaca acaacaacaa gcgtctcctc 60
ttcttcttgt gagagtaaaa aataaaactc ccaaaaaaaa gaaaatcatc aaaaaaacaa 120
atttcaaaaa gagtttttgt gtttggggat taaagaataa aaaaaacaac ctccacc 177

<210> SEQ ID NO 49
<211> LENGTH: 191
<212> TYPE: DNA
<213> ORGANISM: Artificial Sequence
<220> FEATURE:
<223> OTHER INFORMATION: TEE

<400> SEQUENCE: 49
agatcactag aagcttcaag ctctagcagg aagaagaaat aagaagaaga agaagaataa 60
gaagaagcgt ctcgtcttct tcttgtgaga gtaaaaaata aaactcccaa aaaaaataaa 120
atcatcaaaa aaagaaattt caaaaagagt ttttgtgttt ggggattaaa gaataaaaaa 180
aacaacaggc c 191

<210> SEQ ID NO 50
<211> LENGTH: 189
<212> TYPE: DNA
<213> ORGANISM: Artificial Sequence

<220> FEATURE:
<223> OTHER INFORMATION: TEE

<400> SEQUENCE: 50
agatcactag aagcttcaag ctctagcagg aagaagaaat aataagaaga agaagaataa 60
gaagaagcgt ctcctcttct tcttgtgaga gtaaaaaata aaactcccaa aaaaaataaa 120
atcatcaaaa aaataaattt caaaaagagt ttttgtgttt ggggattaaa gaataaaaaa 180
aacaacgcc 189

<210> SEQ ID NO 51
<211> LENGTH: 173
<212> TYPE: DNA
<213> ORGANISM: Artificial Sequence
<220> FEATURE:
<223> OTHER INFORMATION: TEE

<400> SEQUENCE: 51
caagctctag caggaagaag aaakaagaag aagaagaaga agaagaagaa gcgtctcctc 60
ttcttcttgt gagagtaaaa aakaaaactc ccaaaaaaaa kaaaatcatc aaaaaaacaa 120
atttcaaaaa gagtttttgt gtttggggat taaagaakaa aaaaaacaac gtc 173

<210> SEQ ID NO 52
<211> LENGTH: 274
<212> TYPE: DNA
<213> ORGANISM: Artificial Sequence
<220> FEATURE:
<223> OTHER INFORMATION: TEE

<400> SEQUENCE: 52
caagctctag caggaagaag aaakaagaag aagaagaaga agaagaagaa gcgtctcctc 60
ttcttcttgt gagagtaaaa aakaaaactc ccaaaaaaaa kaaaatcatc aaaaaaacaa 120
atttcaaaaa gagtttttgt gtttggggat taaagaakaa aaaaaacaac aggtgagtaa 180
gcgcagttgt cgtctcttgc ggtgccgttg ctggttctca caccttttag gtctgttctc 240
gtcttccgtt ctgactctct ctttttcgtt gcag 274

<210> SEQ ID NO 53
<211> LENGTH: 123
<212> TYPE: DNA
<213> ORGANISM: Artificial Sequence
<220> FEATURE:
<223> OTHER INFORMATION: TEE

<400> SEQUENCE: 53
ggcgtctcct cttcttcttg tgagagtaaa aaataaaact cccaaaaaaa akaaaatcat 60
caaaaaaaca aatttcaaaa agagtttttg tgtttgggga ttaaagaaka aaaaaacaac 120
gtc 123

<210> SEQ ID NO 54
<211> LENGTH: 384
<212> TYPE: DNA
<213> ORGANISM: Artificial Sequence
<220> FEATURE:
<223> OTHER INFORMATION: TEE

<400> SEQUENCE: 54
caagctctag caggaagaag aaataagaag aagaagaaga agaagaagaa gcgtctcctc 60
ttcttcttgt gagagtaaaa aataaaactc ccaaaaaaaa gaaaatcatc aaaaaaacaa 120

```
atttcaaaaa gagtttttgt gtttggggat taaagaataa aaaaaacaac gtctggacaa    180

accacaacta gaatgcagtg aaaaaaatgc tttatttgtg aaatttgtga tgctattgct    240

ttatttgtaa ccattataag ctgcaataaa caagttaaca acaacaattg cattcatttt    300

atgtttcagg ttcaggggga ggtgtgggag gtttttttaaa gcaagtaaaa cctctacaaa    360

tgtggtaaaa tcgataagga tccg                                            384
```

<210> SEQ ID NO 55
<211> LENGTH: 2522
<212> TYPE: DNA
<213> ORGANISM: Artificial Sequence
<220> FEATURE:
<223> OTHER INFORMATION: EEE1+CMV+TEE

<400> SEQUENCE: 55

```
tttcaggcaa ccagagctac atagtgagat cctgtctcaa caaaaataaa ataatctaag     60

gcttcaaagg gttcaatctc ttaggtagct aaatatgaac aaaatttggg aaatgtgacc    120

ttttccttag tgacagtcag atagaacctt ctcgagtgca aggacaccaa gtgcaaacag    180

gctcaagaac agcctggaaa ggtctagtgc tatggggctt caggtcgaat gccaactgtt    240

ttcaagaact gtgtggattt ttctgcctgt aacgaattca gattcatttt tcaaaactcg    300

gggagagttt tcccccttta taattttttt tttaaattta ttaaactttg tttcgttccc    360

cttgttttga gaattgcaga gtcatccacc ctgtcacagt gccagggagc tcagggatgg    420

gcccaggggc ctggcggggc tgaaggggct ggggaagcga gggctccaaa gggaccccag    480

tgtggcagga gccaaagccc taggtcccta gaacgcagag gccaccggga ccccccagac    540

ggggtaagcg ggtgggtgtc tggggcgcga agccgcactg cgcatgcgcc gaggtccgct    600

ccggccgcgc tgatccaagc cgggttctcg cgccgacctg gtcgtgattg acaagtcaca    660

cacgctgatc cctccgcggg gccgcacagg gtcacagcct ttcccctccc cacaaagccc    720

cctactctct gggcaccaca cacgaacatt ccttgagcgt gaccttgttg gctctagtca    780

ggcgcctccg gtgcagagac tggaacggcc ttgggaagta gtccctaacc gcatttccgc    840

ggagggatcg tcgggagggc gtggcttctg aggattatat aaggcgactc cgggcgggtc    900

ttagctagtt ccgtcggaga cccgagttca gtcgccgctt ctctgtgagg actgctgccg    960

ccgccgctgg tgaggagaag ccgccgcgct tggcgtagct gagagacggg gagggggcgc   1020

ggacacgagg ggcagcccgc ggcctggacg ttctgtttcc gtggcccgcg aggaaggcga   1080

ctgtcctgag gcggaggacc cagcggcaag atggcggcca agtggaagcc tgaggggata   1140

ggcgagcggc cctgaggcgc tcgacggggt tggggggggaa gcaggcccgc gaggcagctg   1200

cagccgggaa cgtgcggcca acccccttatt tttttgacg ggttgcgggc cgtaggtgcc   1260

tccgaagtga gagccgtggg cgtttgactg tcgggagagg tcggtcggat tttcatccgt   1320

tgctaaagac ggaagtgcga ctgagacggg aaggggggggg agtcggttgg tggcggttga   1380

acctggacta aggcgcacat gacgtcgcgg tttctatggg ctcataatgg gtggtgagga   1440

catttccctg tttaaactta aacaagtttg tacaaaaaag caggctagat cttcaatatt   1500

ggccattagc catattattc attggttata tagcataaat caatattggc tattggccat   1560

tgcatacgtt gtatctatat cataatatgt acatttatat tggctcatgt ccaatatgac   1620

cgccatgttg gcattgatta ttgactagtt attaatagta atcaattacg gggtcattag   1680

ttcatagccc atatatggag ttccgcgtta cataacttac ggtaaatggc ccgcctggct   1740

gaccgcccaa cgacccccgc ccattgacgt caataatgac gtatgttccc atagtaacgc   1800
```

caatagggac tttccattga cgtcaatggg tggagtattt acggtaaact gcccacttgg 1860
cagtacatca agtgtatcat atgccaagtc cgccccctat tgacgtcaat gacggtaaat 1920
ggcccgcctg gcattatgcc cagtacatga ccttacggga ctttcctact tggcagtaca 1980
tctacgtatt agtcatcgct attaccatag tgatgcggtt ttggcagtac accaatgggc 2040
gtggatagcg gtttgactca cggggatttc caagtctcca ccccattgac gtcaatggga 2100
gtttgttttg gcaccaaaat caacgggact ttccaaaatg tcgtaataac cccgccccgt 2160
tgacgcaaat gggcggtagg cgtgtacggt gggaggtcta tataagcaga gctcgtttag 2220
tgaaccgtca gatcactaga agcttcaagc tctagcagga agaagaaaga agaagaagaa 2280
gaagaagaag aagaagcgtc tcctcttctt cttgtgagag taaaaaagaa aactcccaaa 2340
aaaaagaaaa tcatcaaaaa aacaaatttc aaaaagagtt tttgtgtttg ggattaaag 2400 aagaaaaaaa acaacaggtg agtaagcgca gttgtcgtct cttgcggtgc cgttgctggt 2460
tctcacacct tttaggtctg ttctcgtctt ccgttctgac tctctctttt tcgttgcagg 2520
cc 2522

<210> SEQ ID NO 56
<211> LENGTH: 3321
<212> TYPE: DNA
<213> ORGANISM: Artificial Sequence
<220> FEATURE:
<223> OTHER INFORMATION: EEE1-Xt+CMV+TEE

<400> SEQUENCE: 56
tggtgaccct gtctcaaaaa accctcaaaa agtgttggga ttagtggcat gcaccaccat 60
tcccaccaaa ggtttatttt taataatatg tgtgtgagtg tgtatcacta tgagtatatg 120
tcaatatgtg tcaatgtccc cagggacatt taaagagccc ctgaagctgg agtcataggc 180
cattatgaac tgcctgacat ggctaatggg aattgaactc agattttctg gaagttatac 240
ctgctcttac tgctgagcca tgtctctgaa gaccccaggg attttttttt tttttgaga 300 caggtatttt ctgtatagcc ctggctgtcc tgaaagcact ctctatatgt agaccaggct 360
tgcctggagc ttggatatgc acctgcttct gcctcaggaa tggtgggatt gaaggtgtgc 420
accaccacat ccgctaacat gcacaattct taatgggttt atatcttatt taatgaatga 480
aaggtttggg ggatggatgt agcttaatgg aaaatgactg aagatttcaa ttaaaaatct 540
ggggcttagc tgcgcggtgg gtggtgcctg cctttagtcc cagtactggg gaggcagagg 600
aaggaggatc tctgtgagtt cgaggccagc tggtctataa cgtgagttcc aggacagcca 660
gagatacaca gacaaaccct gtctcaccaa aacaaaacaa caacaacaac aacaaatctg 720
ggacgtaggc ttggtgtggt ggcacacatt ttgattccag cacttggaag gaagaggcct 780
gcatggtcta catagcttgt ttcaggcaac cagagctaca tagtgagatc ctgtctcaac 840
aaaaataaaa taatctaagg cttcaaaggg ttcaatctct taggtagcta aatatgaaca 900
aaatttggga aatgtgacct ttttccttagt gacagtcaga tagaaccttc tcgagtgcaa 960
ggacaccaag tgcaaacagg ctcaagaaca gcctggaaag gtctagtgct atggggcttc 1020
aggtcgaatg ccaactgttt tcaagaactg tgtggatttt tctgcctgta acgaattcag 1080
attcattttt caaaactcgg ggagagtttt cccccttat aatttttttt ttaaatttat 1140
taaactttgt ttcgttcccc ttgttttgag aattgcagag tcatccaccc tgtcacagtg 1200
ccagggagct cagggatggg cccaggggcc tggcggggct gaaggggctg ggaagcgag 1260

```
ggctccaaag ggaccccagt gtggcaggag ccaaagccct aggtccctag aacgcagagg   1320
ccaccgggac cccccagacg gggtaagcgg gtgggtgtct ggggcgcgaa gccgcactgc   1380
gcatgcgccg aggtccgctc cggccgcgct gatccaagcc gggttctcgc gccgacctgg   1440
tcgtgattga caagtcacac acgctgatcc ctccgcgggg ccgcacaggg tcacagcctt   1500
tcccctcccc acaaagcccc ctactctctg ggcaccacac acgaacattc cttgagcgtg   1560
accttgttgg ctctagtcag gcgcctccgg tgcagagact ggaacggcct tgggaagtag   1620
tccctaaccg catttccgcg gagggatcgt cgggagggcg tggcttctga ggattatata   1680
aggcgactcc gggcgggtct tagctagttc cgtcggagac ccgagttcag tcgccgcttc   1740
tctgtgagga ctgctgccgc cgccgctggt gaggagaagc cgccgcgctt ggcgtagctg   1800
agagacgggg agggggcgcg gacacgaggg gcagcccgcg gcctggacgt tctgtttccg   1860
tggcccgcga ggaaggcgac tgtcctgagg cggaggaccc agcggcaaga tggcggccaa   1920
gtggaagcct gaggggatag gcgagcggcc ctgaggcgct cgacggggtt ggggggggaag   1980
caggcccgcg aggcagctgc agccgggaac gtgcggccaa ccccttattt tttttgacgg   2040
gttgcgggcc gtaggtgcct ccgaagtgag agccgtgggc gtttgactgt cgggagaggt   2100
cggtcggatt ttcatccgtt gctaaagacg gaagtgcgac tgagacggga aggggggga   2160
gtcggttggt ggcggttgaa cctggactaa ggcgcacatg acgtcgcggt ttctatgggc   2220
tcataatggg tggtgaggac atttccctgt ttaaacttaa acaagtttgt acaaaaaagc   2280
aggctagatc ttcaatattg gccattagcc atattattca ttggttatat agcataaatc   2340
aatattggct attggccatt gcatacgttg tatctatatc ataatatgta catttatatt   2400
ggctcatgtc caatatgacc gccatgttgg cattgattat tgactagtta ttaatagtaa   2460
tcaattacgg ggtcattagt tcatagccca tatatggagt tccgcgttac ataacttacg   2520
gtaaatggcc cgcctggctg accgcccaac gacccccgcc cattgacgtc aataatgacg   2580
tatgttccca tagtaacgcc aatagggact ttccattgac gtcaatgggt ggagtattta   2640
cggtaaactg cccacttggc agtacatcaa gtgtatcata tgccaagtcc gccccctatt   2700
gacgtcaatg acggtaaatg gcccgcctgg cattatgccc agtacatgac cttacgggac   2760
tttcctactt ggcagtacat ctacgtatta gtcatcgcta ttaccatagt gatgcggttt   2820
tggcagtaca ccaatgggcg tggatagcgg tttgactcac ggggatttcc aagtctccac   2880
cccattgacg tcaatgggag tttgttttgg caccaaaatc aacgggactt tccaaaatgt   2940
cgtaataacc ccgccccgtt gacgcaaatg ggcggtaggc gtgtacggtg ggaggtctat   3000
ataagcagag ctcgtttagt gaaccgtcag atcactagaa gcttcaagct ctagcaggaa   3060
gaagaaagaa gaagaagaag aagaagaaga agaagcgtct cctcttcttc ttgtgagagt   3120
aaaaaagaaa actcccaaaa aaaagaaaat catcaaaaaa acaaatttca aaaagagttt   3180
ttgtgtttgg ggattaaaga agaaaaaaaa caacaggtga gtaagcgcag ttgtcgtctc   3240
ttgcggtgcc gttgctggtt ctcacacctt ttaggtctgt tctcgtcttc cgttctgact   3300
ctctcttttt cgttgcaggc c                                             3321
```

<210> SEQ ID NO 57
<211> LENGTH: 2232
<212> TYPE: DNA
<213> ORGANISM: Artificial Sequence
<220> FEATURE:
<223> OTHER INFORMATION: EEE1-80+CMV+TEE

<400> SEQUENCE: 57

```
tcaaaactcg gggagagttt tccccccttta taattttttt tttaaattta ttaaactttg     60
tttcgttccc cttgttttga gaattgcaga gtcatccacc ctgtcacagt gccagggagc    120
tcagggatgg gcccaggggc ctggcggggc tgaaggggct ggggaagcga gggctccaaa    180
gggaccccag tgtggcagga gccaaagccc taggtcccta gaacgcagag gccaccggga    240
ccccccagac ggggtaagcg ggtgggtgtc tggggcgcga agccgcactg cgcatgcgcc    300
gaggtccgct ccggccgcgc tgatccaagc cgggttctcg cgccgacctg gtcgtgattg    360
acaagtcaca cacgctgatc cctccgcggg gccgcacagg gtcacagcct ttcccctccc    420
cacaaagccc cctactctct gggcaccaca cacgaacatt ccttgagcgt gaccttgttg    480
gctctagtca ggcgcctccg gtgcagagac tggaacggcc ttgggaagta gtccctaacc    540
gcatttccgc ggagggatcg tcgggagggc gtggcttctg aggattatat aaggcgactc    600
cgggcgggtc ttagctagtt ccgtcggaga cccgagttca gtcgccgctt ctctgtgagg    660
actgctgccg ccgccgctgg tgaggagaag ccgccgcgct tggcgtagct gagagacggg    720
gaggggggcgc ggacacgagg ggcagcccgc ggcctggacg ttctgtttcc gtggcccgcg    780
aggaaggcga ctgtcctgag gcggaggacc cagcggcaag atggcggcca agtggaagcc    840
tgaggggata ggcgagcggc cctgaggcgc tcgacggggt tggggggggaa gcaggcccgc    900
gaggcagctg cagccgggaa cgtgcggcca accccttatt ttttttgacg ggttgcgggc    960
cgtaggtgcc tccgaagtga gagccgtggg cgtttgactg tcgggagagg tcggtcggat   1020
tttcatccgt tgctaaagac ggaagtgcga ctgagacggg aagggggggg agtcggttgg   1080
tggcggttga acctggacta aggcgcacat gacgtcgcgg tttctatggg ctcataatgg   1140
gtggtgagga catttccctg tttaaactta aacaagtttg tacaaaaaag caggctagat   1200
cttcaatatt ggccattagc catattattc attggttata tagcataaat caatattggc   1260
tattggccat tgcatacgtt gtatctatat cataatatgt acatttatat tggctcatgt   1320
ccaatatgac cgccatgttg gcattgatta ttgactagtt attaatagta atcaattacg   1380
gggtcattag ttcatagccc atatatggag ttccgcgtta cataacttac ggtaaatggc   1440
ccgcctggct gaccgcccaa cgacccccgc ccattgacgt caataatgac gtatgttccc   1500
atagtaacgc caatagggac tttccattga cgtcaatggg tggagtattt acggtaaact   1560
gcccacttgg cagtacatca agtgtatcat atgccaagtc cgccccctat tgacgtcaat   1620
gacggtaaat ggcccgcctg gcattatgcc cagtacatga ccttacggga ctttcctact   1680
tggcagtaca tctacgtatt agtcatcgct attaccatag tgatgcggtt ttggcagtac   1740
accaatgggc gtggatagcg gtttgactca cggggatttc caagtctcca ccccattgac   1800
gtcaatggga gtttgttttg gcaccaaaat caacgggact ttccaaaatg tcgtaataac   1860
cccgccccgt tgacgcaaat gggcggtagg cgtgtacggt gggaggtcta tataagcaga   1920
gctcgtttag tgaaccgtca gatcactaga agcttcaagc tctagcagga agaagaaaga   1980
agaagaagaa gaagaagaag aagaagcgtc tcctcttctt cttgtgagag taaaaaagaa   2040
aactcccaaa aaaaagaaaa tcatcaaaaa aacaaatttc aaaaagagtt tttgtgtttg   2100
gggattaaag aagaaaaaaa acaacaggtg agtaagcgca gttgtcgtct cttgcggtgc   2160
cgttgctggt tctcacacct tttaggtctg ttctcgtctt ccgttctgac tctctctttt   2220
tcgttgcagg cc                                                       2232
```

<210> SEQ ID NO 58

<211> LENGTH: 1942
<212> TYPE: DNA
<213> ORGANISM: Artificial Sequence
<220> FEATURE:
<223> OTHER INFORMATION: EEE1-60+CMV+TEE

<400> SEQUENCE: 58

```
cgcatgcgcc gaggtccgct ccggccgcgc tgatccaagc cgggttctcg cgccgacctg      60
gtcgtgattg acaagtcaca cacgctgatc cctccgcggg gccgcacagg gtcacagcct     120
ttcccctccc cacaaagccc cctactctct gggcaccaca cacgaacatt ccttgagcgt     180
gaccttgttg gctctagtca ggcgcctccg gtgcagagac tggaacggcc ttgggaagta     240
gtccctaacc gcatttccgc ggagggatcg tcgggagggc gtggcttctg aggattatat     300
aaggcgactc cgggcgggtc ttagctagtt ccgtcggaga cccgagttca gtcgccgctt     360
ctctgtgagg actgctgccg ccgccgctgg tgaggagaag ccgccgcgct tggcgtagct     420
gagagacggg gaggggggcgc ggacacgagg ggcagcccgc ggcctggacg ttctgtttcc     480
gtggcccgcg aggaaggcga ctgtcctgag gcggaggacc cagcggcaag atggcggcca     540
agtggaagcc tgaggggata ggcgagcggc cctgaggcgc tcgacggggt tggggggaa      600
gcaggcccgc gaggcagctg cagccgggaa cgtgcggcca accccttatt ttttttgacg     660
ggttgcgggc cgtaggtgcc tccgaagtga gagccgtggg cgtttgactg tcgggagagg     720
tcggtcggat tttcatccgt tgctaaagac ggaagtgcga ctgagacggg aagggggggg     780
agtcggttgg tggcggttga acctggacta aggcgcacat gacgtcgcgg tttctatggg     840
ctcataatgg gtggtgagga catttccctg tttaaactta aacaagtttg tacaaaaaag     900
caggctagat cttcaatatt ggccattagc catattattc attggttata tagcataaat     960
caatattggc tattggccat tgcatacgtt gtatctatat cataatatgt acatttatat    1020
tggctcatgt ccaatatgac cgccatgttg gcattgatta ttgactagtt attaatagta    1080
atcaattacg gggtcattag ttcatagccc atatatggag ttccgcgtta cataacttac    1140
ggtaaatggc ccgcctggct gaccgcccaa cgacccccgc ccattgacgt caataatgac    1200
gtatgttccc atagtaacgc caatagggac tttccattga cgtcaatggg tggagtattt    1260
acggtaaact gcccacttgg cagtacatca agtgtatcat atgccaagtc cgcccccctat    1320
tgacgtcaat gacggtaaat ggcccgcctg gcattatgcc cagtacatga ccttacggga    1380
ctttcctact tggcagtaca tctacgtatt agtcatcgct attaccatag tgatgcggtt    1440
ttggcagtac accaatgggc gtggatagcg gtttgactca cggggatttc caagtctcca    1500
ccccattgac gtcaatggga gtttgttttg gcaccaaaat caacgggact ttccaaaatg    1560
tcgtaataac cccgccccgt tgacgcaaat gggcggtagg cgtgtacggt gggaggtcta    1620
tataagcaga gctcgtttag tgaaccgtca gatcactaga agcttcaagc tctagcagga    1680
agaagaaaga agaagaagaa gaagaagaag aagaagcgtc tcctcttctt cttgtgagag    1740
taaaaaagaa aactcccaaa aaaaagaaaa tcatcaaaaa aacaaatttc aaaaagagtt    1800
tttgtgtttg gggattaaag aagaaaaaaa acaacaggtg agtaagcgca gttgtcgtct    1860
cttgcggtgc cgttgctggt tctcacacct tttaggtctg ttctcgtctt ccgttctgac    1920
tctctctttt tcgttgcagg cc                                             1942
```

<210> SEQ ID NO 59
<211> LENGTH: 1449
<212> TYPE: DNA
<213> ORGANISM: Artificial Sequence

```
<220> FEATURE:
<223> OTHER INFORMATION: EEE1

<400> SEQUENCE: 59

tttcaggcaa ccagagctac atagtgagat cctgtctcaa caaaaataaa ataatctaag      60

gcttcaaagg gttcaatctc ttaggtagct aaatatgaac aaaatttggg aaatgtgacc     120

ttttccttag tgacagtcag atagaacctt ctcgagtgca aggacaccaa gtgcaaacag     180

gctcaagaac agcctggaaa ggtctagtgc tatggggctt caggtcgaat gccaactgtt     240

ttcaagaact gtgtggattt ttctgcctgt aacgaattca gattcatttt tcaaaactcg     300

gggagagttt tccccccttta taattttttt tttaaattta ttaaactttg tttcgttccc     360

cttgttttga gaattgcaga gtcatccacc ctgtcacagt gccagggagc tcagggatgg     420

gcccaggggc ctggcggggc tgaaggggct ggggaagcga gggctccaaa gggaccccag     480

tgtggcagga gccaaagccc taggtcccta gaacgcagag gccaccggga ccccccagac     540

ggggtaagcg ggtgggtgtc tggggcgcga agccgcactg cgcatgcgcc gaggtccgct     600

ccggccgcgc tgatccaagc cgggttctcg cgccgacctg gtcgtgattg acaagtcaca     660

cacgctgatc cctccgcggg gccgcacagg gtcacagcct ttcccctccc cacaaagccc     720

cctactctct gggcaccaca cacgaacatt ccttgagcgt gaccttgttg gctctagtca     780

ggcgcctccg gtgcagagac tggaacggcc ttgggaagta gtccctaacc gcatttccgc     840

ggagggatcg tcgggagggc gtggcttctg aggattatat aaggcgactc cgggcgggtc     900

ttagctagtt ccgtcggaga cccgagttca gtcgccgctt ctctgtgagg actgctgccg     960

ccgccgctgg tgaggagaag ccgccgcgct tggcgtagct gagagacggg gagggggcgc    1020

ggacacgagg ggcagcccgc ggcctggacg ttctgtttcc gtggcccgcg aggaaggcga    1080

ctgtcctgag gcggaggacc cagcggcaag atggcggcca agtggaagcc tgaggggata    1140

ggcgagcggc cctgaggcgc tcgacggggt tgggggggaa gcaggcccgc gaggcagctg    1200

cagccgggaa cgtgcggcca acccccttatt tttttgacg ggttgcgggc cgtaggtgcc    1260

tccgaagtga gagccgtggg cgtttgactg tcgggagagg tcggtcggat tttcatccgt    1320

tgctaaagac ggaagtgcga ctgagacggg aagggggggg agtcggttgg tggcggttga    1380

acctggacta aggcgcacat gacgtcgcgg tttctatggg ctcataatgg gtggtgagga    1440

catttccct                                                            1449


<210> SEQ ID NO 60
<211> LENGTH: 1228
<212> TYPE: DNA
<213> ORGANISM: Artificial Sequence
<220> FEATURE:
<223> OTHER INFORMATION: EEE2

<400> SEQUENCE: 60

gtaaagcaga tcacacagaa tatggcacac ttgagcactt gatgtgtact acattactct      60

tagtgacgac tttaattatc gtgcgcattc ccagcgcttc ctatggtgcc caacacagag     120

cggacgccta gagacaattt tgggggatgg ggcagatgct ctgcctcggg aaaaaaaaag     180

cacacctgcc ctgacgttgg tggctgggtc tggaagatac gtggaaatta agctaaggat     240

gtgtggcttc cagatcaaaa accgcaaaaa tctaacgccg tgactactga ctacggtcag     300

agagcacaga ctggagcaac ctctcacggc ctgggctgtc tgcgcgtgcg tgagccagaa     360

acccgagggg ctccctgggc ccgccctatc gatcgacccg atcggggatc gtcagcttgg     420
```

ttctggccac agaggttgct cttctcgcga tgcttcagac ctggcggcag ggaaagggtg 480
ggctaattgg agagccagga agagcgtgag gcggccccac gctgctttcc cagaaggctg 540
tgcgtgctcc tcgcttcctc cgcggtcttc cgagcggtcg cgtgaactgc ttccagcagg 600
ctggccatgg cgcttcacgt tcccaaggct ccgggctttg cccagatgct caaggaggga 660
gcgaaagtaa gggctgaagg aaaggaatga ggtgggagcg tcagcatagg gctgcggcgg 720
cggcggcgaa gtaggagggc ctactaacgg gctgagcgtg ctgccctggc tcagcggccg 780
ggggaagaga agattccaga aagggaggtg attttggaag ggctcggcca ccggagcctg 840
cgggcacttc tcttcttccg cgaccgggag aaggccgagg gatcggcggc acgatcgaca 900
ttgtacacct tgaaggtgga cggatgtgaa gccgcgcgtg cgttttgcct ccatccgtaa 960
atggggctaa ggcccgtcac ccttaaagga ggttgtgagg gtgaaattga ataacgtaga 1020
tgaaattgtc ttgagaactg cgacgtcgat tatcacatag ctcgcgagtt gtaggatggg 1080
gaagaacgag aactagccga tccagagaag agagtgggaa aaagggccgg gtcttggttg 1140
cttgcttccc agtgagaaac atacggcttt cagcttagtt gacagaagcc atgcgttgta 1200
gccaaatgag ttccggtccc aacttatg 1228

<210> SEQ ID NO 61
<211> LENGTH: 753
<212> TYPE: DNA
<213> ORGANISM: Artificial Sequence
<220> FEATURE:
<223> OTHER INFORMATION: CMV promoter

<400> SEQUENCE: 61
tcaatattgg ccattagcca tattattcat tggttatata gcataaatca atattggcta 60
ttggccattg catacgttgt atctatatca taatatgtac atttatattg gctcatgtcc 120
aatatgaccg ccatgttggc attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300
agtaacgcca atagggactt tccattgacg tcaatgggtg gagtatttac ggtaaactgc 360
ccacttggca gtacatcaag tgtatcatat gccaagtccg ccccctattg acgtcaatga 420
cggtaaatgg cccgcctggc attatgccca gtacatgacc ttacgggact ttcctacttg 480
gcagtacatc tacgtattag tcatcgctat taccatagtg atgcggtttt ggcagtacac 540
caatgggcgt ggatagcggt ttgactcacg gggatttcca agtctccacc ccattgacgt 600
caatgggagt ttgttttggc accaaaatca acgggacttt ccaaaatgtc gtaataaccc 660
cgccccgttg acgcaaatgg gcggtaggcg tgtacggtgg gaggtctata taagcagagc 720
tcgtttagtg aaccgtcaga tcactagaag ctt 753

<210> SEQ ID NO 62
<211> LENGTH: 69
<212> TYPE: DNA
<213> ORGANISM: Artificial Sequence
<220> FEATURE:
<223> OTHER INFORMATION: minimal CMV promoter

<400> SEQUENCE: 62
taggcgtgta cggtgggagg tctatataag cagagctcgt ttagtgaacc gtcagatcac 60
tagaagctt 69

<210> SEQ ID NO 63
<211> LENGTH: 2248
<212> TYPE: DNA
<213> ORGANISM: Artificial Sequence
<220> FEATURE:
<223> OTHER INFORMATION: EEE1-XT

<400> SEQUENCE: 63

```
tggtgaccct gtctcaaaaa accctcaaaa agtgttggga ttagtggcat gcaccaccat     60
tcccaccaaa ggtttatttt taataatatg tgtgtgagtg tgtatcacta tgagtatatg    120
tcaatatgtg tcaatgtccc cagggacatt taaagagccc ctgaagctgg agtcataggc    180
cattatgaac tgcctgacat ggctaatggg aattgaactc agattttctg gaagttatac    240
ctgctcttac tgctgagcca tgtctctgaa gaccccaggg attttttttt tttttgaga    300
caggtatttt ctgtatagcc ctggctgtcc tgaaagcact ctctatatgt agaccaggct    360
tgcctggagc ttggatatgc acctgcttct gcctcaggaa tggtgggatt gaaggtgtgc    420
accaccacat ccgctaacat gcacaattct taatgggttt atatcttatt taatgaatga    480
aaggtttggg ggatggatgt agcttaatgg aaaatgactg aagatttcaa ttaaaaatct    540
ggggcttagc tgcgcggtgg gtggtgcctg cctttagtcc cagtactggg gaggcagagg    600
aaggaggatc tctgtgagtt cgaggccagc tggtctataa cgtgagttcc aggacagcca    660
gagatacaca gacaaaccct gtctcaccaa aacaaaacaa caacaacaac aacaaatctg    720
ggacgtaggc ttggtgtggt ggcacacatt ttgattccag cacttggaag gaagaggcct    780
gcatggtcta catagcttgt ttcaggcaac cagagctaca tagtgagatc ctgtctcaac    840
aaaaataaaa taatctaagg cttcaaaggg ttcaatctct taggtagcta aatatgaaca    900
aaatttggga aatgtgacct tttccttagt gacagtcaga tagaaccttc tcgagtgcaa    960
ggacaccaag tgcaaacagg ctcaagaaca gcctggaaag gtctagtgct atggggcttc   1020
aggtcgaatg ccaactgttt tcaagaactg tgtggatttt tctgcctgta acgaattcag   1080
attcattttt caaaactcgg ggagagtttt ccccctttat aatttttttt ttaaatttat   1140
taaactttgt ttcgttcccc ttgttttgag aattgcagag tcatccaccc tgtcacagtg   1200
ccagggagct cagggatggg cccaggggcc tggcggggct gaaggggctg gggaagcgag   1260
ggctccaaag ggaccccagt gtggcaggag ccaaagccct aggtccctag aacgcagagg   1320
ccaccgggac cccccagacg ggtaagcggg gtgggtgtct ggggcgcgaa gccgcactgc   1380
gcatgcgccg aggtccgctc cggccgcgct gatccaagcc gggttctcgc gccgacctgg   1440
tcgtgattga caagtcacac acgctgatcc ctccgcgggg ccgcacaggg tcacagcctt   1500
tcccctcccc acaaagcccc ctactctctg ggcaccacac acgaacattc cttgagcgtg   1560
accttgttgg ctctagtcag gcgcctccgg tgcagagact ggaacggcct tgggaagtag   1620
tccctaaccg catttccgcg gagggatcgt cgggagggcg tggcttctga ggattatata   1680
aggcgactcc gggcgggtct tagctagttc cgtcggagac ccgagttcag tcgccgcttc   1740
tctgtgagga ctgctgccgc cgccgctggt gaggagaagc cgccgcgctt ggcgtagctg   1800
agagacgggg agggggcgcg gacacgaggg gcagcccgcg gcctggacgt tctgtttccg   1860
tggcccgcga ggaaggcgac tgtcctgagg cggaggaccc agcggcaaga tggcggccaa   1920
gtggaagcct gaggggatag gcgagcggcc ctgaggcgct cgacggggtt gggggggaag   1980
caggcccgcg aggcagctgc agccgggaac gtgcggccaa cccettattt tttttgacgg   2040
gttgcgggcc gtaggtgcct ccgaagtgag agccgtgggc gtttgactgt cgggagaggt   2100
```

```
cggtcggatt ttcatccgtt gctaaagacg gaagtgcgac tgagacggga aggggggga   2160

gtcggttggt ggcggttgaa cctggactaa ggcgcacatg acgtcgcggt ttctatgggc   2220

tcataatggg tggtgaggac atttccct                                       2248
```

<210> SEQ ID NO 64
<211> LENGTH: 724
<212> TYPE: DNA
<213> ORGANISM: Artificial Sequence
<220> FEATURE:
<223> OTHER INFORMATION: EEE1-50

<400> SEQUENCE: 64

```
tctctgggca ccacacacga acattccttg agcgtgacct tgttggctct agtcaggcgc     60

ctccggtgca gagactggaa cggccttggg aagtagtccc taaccgcatt tccgcggagg    120

gatcgtcggg agggcgtggc ttctgaggat tatataaggc gactccgggc gggtcttagc    180

tagttccgtc ggagacccga gttcagtcgc cgcttctctg tgaggactgc tgccgccgcc    240

gctggtgagg agaagccgcc gcgcttggcg tagctgagag acggggaggg ggcgcggaca    300

cgaggggcag cccgcggcct ggacgttctg tttccgtggc ccgcgaggaa ggcgactgtc    360

ctgaggcgga ggacccagcg gcaagatggc ggccaagtgg aagcctgagg ggataggcga    420

gcggccctga ggcgctcgac ggggttgggg gggaagcagg cccgcgaggc agctgcagcc    480

gggaacgtgc ggccaacccc ttattttttt tgacgggttg cgggccgtag gtgcctccga    540

agtgagagcc gtgggcgttt gactgtcggg agaggtcggt cggattttca tccgttgcta    600

aagacggaag tgcgactgag acgggaaggg gggggagtcg gttggtggcg gttgaacctg    660

gactaaggcg cacatgacgt cgcggtttct atgggctcat aatgggtggt gaggacattt    720

ccct                                                                  724
```

<210> SEQ ID NO 65
<211> LENGTH: 1449
<212> TYPE: DNA
<213> ORGANISM: Artificial Sequence
<220> FEATURE:
<223> OTHER INFORMATION: EEE1-SL

<400> SEQUENCE: 65

```
tttcaggcaa ccagagctac atagtgagat cctgtctcaa caaaaataaa ataatctaag     60

gcttcaaagg gttcaatctc ttaggtagct aaatatgaac aaaatttggg aaatgtgacc    120

ttttccttag tgacagtcag atagaacctt ctcgagtgca aggacaccaa gtgcaaacag    180

gctcaagaac agcctggaaa ggtctagtgc tatggggctt caggtcgaat gccaactgtt    240

ttcaagaact gtgtggattt ttctgcctgt aacgaattca gattcatttt tcaaaactcg    300

gggagagttt tcccccttta taattttttt tttaaattta ttaaactttg tttcgttccc    360

cttgttttga gaattgcaga gtcatccacc ctgtcacagt gccagggagc tcagggatgg    420

gcccaggggc ctggcggggc tgaaggggct ggggaagcga gggctccaaa gggaccccag    480

tgtggcagga gccaaagccc taggtcccta gaacgcagag gccaccggga ccccccagac    540

ggggaaagcg gttgggtgtc tggggcgcga agccgcactg cgcatgcgcc gaggtccgct    600

ccggccgcgc tgatccaagc cgggttctcg cgccgacctg gtcgtgattg acaagtcaca    660

cacgctgatc cctccgcggg gccgcacagg gtcacagcct ttcccctccc cacaaagccc    720

cctactctct gggcaccaca cacgaacatt ccttgagcgt gaccttgttg gctctagtca    780

ggcgcctccg gtgcagagac tggaacggcc ttgggaagta gtccctaacc gcatttccgc    840
```

```
ggagggatcg tcgggagggc gtggcttctg aggattatat aaggcgactc cgggcgggtc    900
ttagctagtt ccgtcggaga cccgagttca gtcgccgctt ctctgtgagg actgctgccg    960
ccgccgctgc tgaggagaag ccgccgcgct tggcgtagct gagagacggg gagggggcgc   1020
ggacacgagg ggcagcccgc ggcctggacg ttctgtttcc gtggcccgcg aggaaggcga   1080
ctgtcctgag gcggaggacc cagcggcaag atggcggcca agtggaagcc tgaggggata   1140
ggcgagcggc cctgaggcgc tcgacggggt tggggggga gcaggcccgc gaggcagctg   1200
cagccgggaa cgtgcggcca acccccttatt ttttttgacg ggttgcgggc cgtaggtgcc   1260
tccgaattga gagccgtggg cgtttgactg tcgggagagg tcggtcggat tttcatccgt   1320
tgctaaagac ggaagtgcga ctgagacggg aagggggggg agtcggttgg tggcggttga   1380
acctggacta aggcgcacat gacgtcgcgg tttctatggg ctcataatgg gtggtgagga   1440
catttccct                                                           1449
```

<210> SEQ ID NO 66
<211> LENGTH: 455
<212> TYPE: DNA
<213> ORGANISM: Artificial Sequence
<220> FEATURE:
<223> OTHER INFORMATION: EF1a promoter

<400> SEQUENCE: 66

```
ggatccttgg agctaagcca gcaatggtag agggaagatt ctgcacgtcc cttccaggcg     60
gcctccccgt caccaccccc cccaacccgc cccgaccgga gctgagagta attcatacaa    120
aaggactcgc ccctgccttg gggaatccca gggaccgtcg ttaaactccc actaacgtag    180
aacccagaga tcgctgcgtt cccgcccccct cacccgcccg ctctcgtcat cactgaggtg    240
gagaagagca tgcgtgaggc tccggtgccc gtcagtgggc agagcgcaca tcgcccacag    300
tccccgagaa gttgggggga ggggtcggca attgaaccgg tgcctagaga aggtggcgcg    360
gggtaaactg ggaaagtgat gtcgtgtact ggctccgcct ttttcccgag ggtgggggag    420
aaccgtatat aagtgcagta gtcgccgtga acgtt                               455
```

<210> SEQ ID NO 67
<211> LENGTH: 2617
<212> TYPE: DNA
<213> ORGANISM: Artificial Sequence
<220> FEATURE:
<223> OTHER INFORMATION: Transcription regulating sequence

<400> SEQUENCE: 67

```
tttcaggcaa ccagagctac atagtgagat cctgtctcaa caaaaataaa ataatctaag     60
gcttcaaagg gttcaatctc ttaggtagct aaatatgaac aaaatttggg aaatgtgacc    120
ttttccttag tgacagtcag atagaacctt ctcgagtgca aggacaccaa gtgcaaacag    180
gctcaagaac agcctggaaa ggtctagtgc tatggggctt caggtcgaat gccaactgtt    240
ttcaagaact gtgtggattt ttctgcctgt aacgaattca gattcatttt tcaaaactcg    300
gggagagttt tccccccttta taattttttt tttaaattta ttaaactttg tttcgttccc    360
cttgttttga gaattgcaga gtcatccacc ctgtcacagt gccagggagc tcagggatgg    420
gcccaggggc ctggcggggc tgaaggggct ggggaagcga gggctccaaa gggaccccag    480
tgtggcagga gccaaagccc taggtcccta gaacgcagag gccaccggga ccccccagac    540
ggggtaagcg ggtgggtgtc tggggcgcga agccgcactg cgcatgcgcc gaggtccgct    600
```

```
ccggccgcgc tgatccaagc cgggttctcg cgccgacctg gtcgtgattg acaagtcaca    660
cacgctgatc cctccgcggg gccgcacagg gtcacagcct ttcccctccc cacaaagccc    720
cctactctct gggcaccaca cacgaacatt ccttgagcgt gaccttgttg gctctagtca    780
ggcgcctccg gtgcagagac tggaacggcc ttgggaagta gtccctaacc gcatttccgc    840
ggagggatcg tcgggagggc gtggcttctg aggattatat aaggcgactc cgggcgggtc    900
ttagctagtt ccgtcggaga cccgagttca gtcgccgctt ctctgtgagg actgctgccg    960
ccgccgctgg tgaggagaag ccgccgcgct tggcgtagct gagagacggg gagggggcgc   1020
ggacacgagg ggcagcccgc ggcctggacg ttctgtttcc gtggcccgcg aggaaggcga   1080
ctgtcctgag gcggaggacc cagcggcaag atggcggcca agtggaagcc tgaggggata   1140
ggcgagcggc cctgaggcgc tcgacggggt tggggggggaa gcaggcccgc gaggcagctg   1200
cagccgggaa cgtgcggcca acccccttatt tttttgacg ggttgcgggc cgtaggtgcc   1260
tccgaagtga gagccgtggg cgtttgactg tcgggagagg tcggtcggat tttcatccgt   1320
tgctaaagac ggaagtgcga ctgagacggg aagggggggg agtcggttgg tggcggttga   1380
acctggacta aggcgcacat gacgtcgcgg tttctatggg ctcataatgg gtggtgagga   1440
catttccctg actatagctt tccctcagtt gtaggacagg gtttgggcct cggcctcggg   1500
ttaggctctc cagagtgggc aggaaccgga aatccagagg ggggaaaagt gagcctaaat   1560
tgagttttgt ttcttgtcct atatggttta gagagagact cgctgcaaaa ccgtggctgg   1620
cctggaactc tagaccagaa ccctggcctt tgccgaccca catgattaga ttcaaggcct   1680
gtgccaccag cccaggcttt attattatgg tctgggattt ctgcgatttc atccctggtg   1740
ttttgggatg atgacttgtg ggtcttccct cctcccccctt actgtttctg tccatggcgt   1800
gtgttctaac ccaagtttgt tcttttgggg gggtgggagg gttgcgataa aatgggatct   1860
atctctgccc tcccaacttg agatctgcct gtcagaagtc tcagtgctga gaataaaggt   1920
gtgcattggc tcagacctcg attttttttt tttttattat tttgtaggaa gtctgtagtc   1980
cttacttgat acataagacc agacaggatc tgatttcctg cctatgaatg gtagatcctc   2040
tcagtgactg cagtgtgaat ggggaccacg cttttctcca aactatgcag atagccatga   2100
aagccatgaa atgactttca gccactggta ctgcaatatc cactcaccat ttattatatg   2160
gaccaggttc accatgccta ggtggctttg cttttgagac acggtttctc tgtgtagcct   2220
tggttatgtt tttttgtttg ttttttttaat tatttttggt ttttcgagac agggtttctc   2280
tgtgtagctt tggagcctat cctggcactt gctccggaga ccaggctggc ctccaactca   2340
gatctgcctg cctctgcctc ccgactgctg ggattaaagt aaagccattc tgcaaccctg   2400
aataccactc aataggtttc ttatttgaaa tgtggtttta tgatttttat ttctggattt   2460
agaaaagaaa tcttcagaca gaagtcttca gacagaaact agctgtagtt tggctgtgtg   2520
aactaaattg gcatccattt cacagcaatc caactgttag taccatacca cgaatatttg   2580
tcattcctga cctgtttttt gtttgtgtgt gtgacag                            2617
```

<210> SEQ ID NO 68
<211> LENGTH: 1886
<212> TYPE: DNA
<213> ORGANISM: Artificial Sequence
<220> FEATURE:
<223> OTHER INFORMATION: Backbone vector

<400> SEQUENCE: 68

```
cacgcgtctt aagaccatgt gagcaaaagg ccagcaaaag gccaggaacc gtaaaaaggc     60
```

```
cgcgttgctg gcgtttttcc ataggctccg ccccctgac gacgcatcac aaaaatcgac    120
gcgtcaagtc agaggtggcg aaacccgaca ggactataaa gataccaggc gtttccccct   180
ggaagctccc tcgtgcgctc tcctgttccg accctgccgc ttaccggata cctgtccgcc   240
tttctccctt cgggaagcgt ggcgctttct catagctcac gctgtaggta tctcagttcg   300
gtgtaggtcg ttcgctccaa gctgggctgt gtgcacgaac cccccgttca gcccgaccgc   360
tgcgccttat ccggtaacta tcgtcttgag tccaacccgg taagacacga cttatcgcca   420
ctggcagcag ccactggtaa caggattagc agagcgaggt atacaggcgg tgctacagag   480
ttcttgaagt ggtggcctaa ctacggctac actagaagaa cagtatttgg tatctgcgct   540
ctgctgaagc cagttacctt cggaaaaaga gttggtagct cttgatccgg caaacaaacc   600
accgctggta gcggtggttt ttttgtttgc aagcagcaga ttacgcgcag aaaaaaagga   660
tctcaagaag atcctttgat cttttctacg gggtctgacg cgtcagtgga acgaaaactc   720
acgttaaggg attttggtca tgagattatc aaaaaggatc ttcacctaga tccttttaaa   780
ttaaaaatga agttttaaat caatctaaag tatatatgag taaacttggt ctgacagtta   840
gaaaaactca tcgagcatca aatgaaactg caatttattc atatcaggat tatcaatacc   900
atatttttga aaaagccgtt tctgtaatga aggagaaaac tcaccgaggc agttccatag   960
gatggcaaga tcctggtatc ggtctgcgat tccgacgcgt ccaacatcaa tacaacctat  1020
taatttcccc tcgtcaaaaa taaggttatc aagtgagaaa tcaccatgag tgacgactga  1080
atccggtgag aatggcaaaa gtttatgcat ttctttccag acttgttcaa caggccagcc  1140
attacgctcg tcatcaaaat ctgacgcgtc aaccaaaccg ttattcattc gtgattgcgc  1200
ctgagcgaga cgaaatacgc gatcgctgtt aaaaggacaa ttacaaacag gaatcgaatg  1260
caaccggcgc aggaacactg ccagcgcatc aacaatattt tcacctgaat caggatattc  1320
ttctaatacc tggaatgctg ttttcccagg gatcgcagtg gtgagtaacc acgcgtcatc  1380
aggagtacgg ataaaatgct tgatggtcgg aagaggcata aattccgtca gccagtttag  1440
tctgaccatc tcatctgtaa catcattggc aacgctacct ttgccatgtt tcagaaacaa  1500
ctctggcgca tcgggcttcc catacaatcg atagattgtc gcacctgatt gcccgacatt  1560
atcgcgagcc catttatacc catataaatc agcatccatg ttggaattta atcgcggcct  1620
agagcaagac gtttcacgcg tttgaatatg gctcatactc ttcctttttc aatattattg  1680
aagcatttat cagggttatt gtctcatgag cggatacata tttgaatgta tttagaaaaa  1740
taaacaaata ggggttccgc gcacatttcc ccgaaaagtg ccacctgacg tctaagaaac  1800
cattattatc atgacattaa cctataaaaa taggcgtatc aacgcgtcct gcagggcggc  1860
cgcgtcgacg cgcgcacatg tgtata                                       1886
```

<210> SEQ ID NO 69
<211> LENGTH: 272
<212> TYPE: PRT
<213> ORGANISM: Artificial Sequence
<220> FEATURE:
<223> OTHER INFORMATION: Kanamycin resistance marker

<400> SEQUENCE: 69

```
Met Ser His Ile Gln Thr Arg Glu Thr Ser Cys Ser Arg Pro Arg Leu
1               5                   10                  15

Asn Ser Asn Met Asp Ala Asp Leu Tyr Gly Tyr Lys Trp Ala Arg Asp
            20                  25                  30
```

```
Asn Val Gly Gln Ser Gly Ala Thr Ile Tyr Arg Leu Tyr Gly Lys Pro
        35                  40                  45

Asp Ala Pro Glu Leu Phe Leu Lys His Gly Lys Gly Ser Val Ala Asn
    50                  55                  60

Asp Val Thr Asp Glu Met Val Arg Leu Asn Trp Leu Thr Glu Phe Met
65                  70                  75                  80

Pro Leu Pro Thr Ile Lys His Phe Ile Arg Thr Pro Asp Asp Ala Trp
                85                  90                  95

Leu Leu Thr Thr Ala Ile Pro Gly Lys Thr Ala Phe Gln Val Leu Glu
            100                 105                 110

Glu Tyr Pro Asp Ser Gly Glu Asn Ile Val Asp Ala Leu Ala Val Phe
        115                 120                 125

Leu Arg Arg Leu His Ser Ile Pro Val Cys Asn Cys Pro Phe Asn Ser
    130                 135                 140

Asp Arg Val Phe Arg Leu Ala Gln Ala Gln Ser Arg Met Asn Asn Gly
145                 150                 155                 160

Leu Val Asp Ala Ser Asp Phe Asp Asp Glu Arg Asn Gly Trp Pro Val
                165                 170                 175

Glu Gln Val Trp Lys Glu Met His Lys Leu Leu Pro Phe Ser Pro Asp
            180                 185                 190

Ser Val Val Thr His Gly Asp Phe Ser Leu Asp Asn Leu Ile Phe Asp
        195                 200                 205

Glu Gly Lys Leu Ile Gly Cys Ile Asp Val Gly Arg Val Gly Ile Ala
    210                 215                 220

Asp Arg Tyr Gln Asp Leu Ala Ile Leu Trp Asn Cys Leu Gly Glu Phe
225                 230                 235                 240

Ser Pro Ser Leu Gln Lys Arg Leu Phe Gln Lys Tyr Gly Ile Asp Asn
                245                 250                 255

Pro Asp Met Asn Lys Leu Gln Phe His Leu Met Leu Asp Glu Phe Phe
            260                 265                 270


<210> SEQ ID NO 70
<211> LENGTH: 272
<212> TYPE: PRT
<213> ORGANISM: Artificial Sequence
<220> FEATURE:
<223> OTHER INFORMATION: Kanamycin resistance marker

<400> SEQUENCE: 70

Met Ser His Ile Gln Arg Glu Thr Arg Ser Cys Ser Arg Pro Arg Leu
1               5                   10                  15

Asn Ser Asn Met Asp Ala Asp Leu Tyr Gly Tyr Lys Trp Ala Arg Asp
            20                  25                  30

Asn Val Gly Gln Ser Gly Ala Thr Ile Tyr Arg Leu Tyr Gly Lys Pro
        35                  40                  45

Asp Ala Pro Glu Leu Phe Leu Lys His Gly Lys Gly Ser Val Ala Asn
    50                  55                  60

Asp Val Thr Asp Glu Met Val Arg Leu Asn Trp Leu Thr Glu Phe Met
65                  70                  75                  80

Pro Leu Pro Thr Ile Lys His Phe Ile Arg Thr Pro Asp Asp Ala Trp
                85                  90                  95

Leu Leu Thr Thr Ala Ile Pro Gly Lys Thr Ala Phe Gln Val Leu Glu
            100                 105                 110

Glu Tyr Pro Asp Ser Gly Glu Asn Ile Val Asp Ala Leu Ala Val Phe
        115                 120                 125
```

```
Leu Arg Arg Leu His Ser Ile Pro Val Cys Asn Cys Pro Phe Asn Ser
    130                 135                 140

Asp Arg Val Phe Arg Leu Ala Gln Ala Gln Ser Arg Met Asn Asn Gly
145                 150                 155                 160

Leu Val Asp Ala Ser Asp Phe Asp Asp Glu Arg Asn Gly Trp Pro Val
                165                 170                 175

Glu Gln Val Trp Lys Glu Met His Lys Leu Leu Pro Phe Ser Pro Asp
            180                 185                 190

Ser Val Val Thr His Gly Asp Phe Ser Leu Asp Asn Leu Ile Phe Asp
        195                 200                 205

Glu Gly Lys Leu Ile Gly Cys Ile Asp Val Gly Arg Val Gly Ile Ala
    210                 215                 220

Asp Arg Tyr Gln Asp Leu Ala Ile Leu Trp Asn Cys Leu Gly Glu Phe
225                 230                 235                 240

Ser Pro Ser Leu Gln Lys Arg Leu Phe Gln Lys Tyr Gly Ile Asp Asn
                245                 250                 255

Pro Asp Met Asn Lys Leu Gln Phe His Leu Met Leu Asp Glu Phe Phe
            260                 265                 270


<210> SEQ ID NO 71
<211> LENGTH: 441
<212> TYPE: DNA
<213> ORGANISM: Artificial Sequence
<220> FEATURE:
<223> OTHER INFORMATION: Gene block 1a

<400> SEQUENCE: 71

gcgttgctgg cgtttttcca taggctccgc ccccctgacg agcatcacaa aaatcgacgc     60

tcaagtcaga ggtggcgaaa cccgacagga ctataaagat accaggcgtt tccccctgga    120

agctccctcg tgcgctctcc tgttccgacc ctgccgctta ccggatacct gtccgccttt    180

ctcccttcgg gaagcgtggc gctttctcat agctcacgct gtaggtatct cagttcggtg    240

taggtcgttc gctccaagct gggctgtgtg cacgaacccc ccgttcagcc cgaccgctgc    300

gccttatccg gtaactatcg tcttgagtcc aacccggtaa gacacgactt atcgccactg    360

gcagcagcca ctggtaacag gattagcaga gcgaggtatg taggcggtgc tacagagttc    420

ttgaagtggt ggcctaacta c                                              441


<210> SEQ ID NO 72
<211> LENGTH: 466
<212> TYPE: DNA
<213> ORGANISM: Artificial Sequence
<220> FEATURE:
<223> OTHER INFORMATION: Gene block 2a

<400> SEQUENCE: 72

agttcttgaa gtggtggcct aactacggct acactagaag aacagtattt ggtatctgcg     60

ctctgctgaa gccagttacc ttcggaaaaa gagttggtag ctcttgatcc ggcaaacaaa    120

ccaccgctgg tagcggtggt ttttttgttt gcaagcagca gattacgcgc agaaaaaaag    180

gatctcaaga agatcctttg atcttttcta cggggtctga cgctcagtgg aacgaaaact    240

cacgttaagg gattttggtc atgagattat caaaaaggat cttcacctag atccttttaa    300

attaaaaatg aagttttaaa tcaatctaaa gtatatatga gtaaacttgg tctgacagtt    360

agaaaaactc atcgagcatc aaatgaaact gcaatttatt catatcagga ttatcaatac    420

catatttttg aaaaagccgt ttctgtaatg aaggagaaaa ctcacc                   466
```

<210> SEQ ID NO 73
<211> LENGTH: 488
<212> TYPE: DNA
<213> ORGANISM: Artificial Sequence
<220> FEATURE:
<223> OTHER INFORMATION: Gene block 3a

<400> SEQUENCE: 73
ttctgtaatg aaggagaaaa ctcaccgagg cagttccata ggatggcaag atcctggtat 60
cggtctgcga ttccgactcg tccaacatca atacaaccta ttaatttccc ctcgtcaaaa 120
ataaggttat caagtgagaa atcaccatga gtgacgactg aatccggtga gaatggcaaa 180
agtttatgca tttctttcca gacttgttca acaggccagc cattacgctc gtcatcaaaa 240
tcactcgcat caaccaaacc gttattcatt cgtgattgcg cctgagcgag acgaaatacg 300
cgatcgctgt taaaaggaca attacaaaca ggaatcgaat gcaaccggcg caggaacact 360
gccagcgcat caacaatatt ttcacctgaa tcaggatatt cttctaatac ctggaatgct 420
gttttcccag ggatcgcagt ggtgagtaac catgcatcat caggagtacg gataaaatgc 480
ttgatggt 488

<210> SEQ ID NO 74
<211> LENGTH: 451
<212> TYPE: DNA
<213> ORGANISM: Artificial Sequence
<220> FEATURE:
<223> OTHER INFORMATION: Gene block 4a

<400> SEQUENCE: 74
ggagtacgga taaaatgctt gatggtcgga agaggcataa attccgtcag ccagtttagt 60
ctgaccatct catctgtaac atcattggca acgctacctt tgccatgttt cagaaacaac 120
tctggcgcat cgggcttccc atacaatcga tagattgtcg cacctgattg cccgacatta 180
tcgcgagccc atttataccc atataaatca gcatccatgt tggaatttaa tcgcggccta 240
gagcaagacg tttcccgttg aatatggctc atactcttcc tttttcaata ttattgaagc 300
atttatcagg gttattgtct catgagcgga tacatatttg aatgtattta gaaaaataaa 360
caaatagggg ttccgcgcac atttccccga aaagtgccac ctgacgtcta agaaaccatt 420
attatcatga cattaaccta taaaaatagg c 451

<210> SEQ ID NO 75
<211> LENGTH: 164
<212> TYPE: DNA
<213> ORGANISM: Artificial Sequence
<220> FEATURE:
<223> OTHER INFORMATION: Gene block 5a

<400> SEQUENCE: 75
catgacatta acctataaaa ataggcgtat caacgcgtcc tgcagggcgg ccgcgtcgac 60
gcgcgcacat gtgtatacac gcgtcttaag accatgtgag caaaaggcca gcaaaaggcc 120
aggaaccgta aaaaggccgc gttgctggcg tttttccata ggct 164

<210> SEQ ID NO 76
<211> LENGTH: 488
<212> TYPE: DNA
<213> ORGANISM: Artificial Sequence
<220> FEATURE:
<223> OTHER INFORMATION: Gene block 3b

<400> SEQUENCE: 76

```
ttctgtaatg aaggagaaaa ctcaccgagg cagttccata ggatggcaag atcctggtat     60

cggtctgcga ttccgacgcg tccaacatca atacaaccta ttaatttccc ctcgtcaaaa    120

ataaggttat caagtgagaa atcaccatga gtgacgactg aatccggtga gaatggcaaa    180

agtttatgca tttctttcca gacttgttca acaggccagc cattacgctc gtcatcaaaa    240

tctgacgcgt caaccaaacc gttattcatt cgtgattgcg cctgagcgag acgaaatacg    300

cgatcgctgt taaaaggaca attacaaaca ggaatcgaat gcaaccggcg caggaacact    360

gccagcgcat caacaatatt ttcacctgaa tcaggatatt cttctaatac ctggaatgct    420

gttttcccag ggatcgcagt ggtgagtaac cacgcgtcat caggagtacg gataaaatgc    480

ttgatggt                                                             488
```

```
<210> SEQ ID NO 77
<211> LENGTH: 454
<212> TYPE: DNA
<213> ORGANISM: Artificial Sequence
<220> FEATURE:
<223> OTHER INFORMATION: Gene block 4b

<400> SEQUENCE: 77

ggagtacgga taaaatgctt gatggtcgga agaggcataa attccgtcag ccagtttagt     60

ctgaccatct catctgtaac atcattggca acgctacctt tgccatgttt cagaaacaac    120

tctggcgcat cgggcttccc atacaatcga tagattgtcg cacctgattg cccgacatta    180

tcgcgagccc atttataccc atataaatca gcatccatgt tggaatttaa tcgcggccta    240

gagcaagacg tttcacgcgt ttgaatatgg ctcatactct tcctttttca atattattga    300

agcatttatc agggttattg tctcatgagc ggatacatat ttgaatgtat ttagaaaaat    360

aaacaaatag gggttccgcg cacatttccc cgaaaagtgc cacctgacgt ctaagaaacc    420

attattatca tgacattaac ctataaaaat aggc                                454
```

```
<210> SEQ ID NO 78
<211> LENGTH: 454
<212> TYPE: DNA
<213> ORGANISM: Artificial Sequence
<220> FEATURE:
<223> OTHER INFORMATION: Gene block 4c

<400> SEQUENCE: 78

ggagtacgga taaaatgctt gatggtcgga agaggcataa attccgtcag ccagtttagt     60

ctgaccatct catctgtaac atcattggca acgctacctt tgccatgttt cagaaacaac    120

tctggcgcat cgggcttccc atacaatcga tagattgtcg cacctgattg cccgacatta    180

tcgcgagccc atttataccc atataaatca gcatccatgt tggaatttaa tcgcggccta    240

gagcaagaac gcgtttcccg ttgaatatgg ctcatactct tcctttttca atattattga    300

agcatttatc agggttattg tctcatgagc ggatacatat ttgaatgtat ttagaaaaat    360

aaacaaatag gggttccgcg cacatttccc cgaaaagtgc cacctgacgt ctaagaaacc    420

attattatca tgacattaac ctataaaaat aggc                                454
```

```
<210> SEQ ID NO 79
<211> LENGTH: 861
<212> TYPE: DNA
<213> ORGANISM: Artificial Sequence
<220> FEATURE:
<223> OTHER INFORMATION: Ampicillin resistance marker
```

<400> SEQUENCE: 79

```
atgagcatcc agcatttccg tgtcgccctt attccctttt ttgcggcatt ttgccttcct     60
gtttttgctc acccagaaac gctggtgaaa gtaaaagatg ctgaagatca gttgggagca    120
cgcgtgggtt acatcgaact ggatctcaac agcggtaaga tccttgagag ttttcgcccc    180
gaagaacgtt ttccaatgat gagcactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg gggatcatgt aacgcgtctt    480
gatcgttggg aaccggagct gaatgaagcc ataccaaacg acgagcgtga caccacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatggatgaa cgaaatagac agatcgctga gataggtgcc    840
tcactgatta agcattggta a                                              861
```

<210> SEQ ID NO 80
<211> LENGTH: 1895
<212> TYPE: DNA
<213> ORGANISM: Artificial Sequence
<220> FEATURE:
<223> OTHER INFORMATION: Backbone vector

<400> SEQUENCE: 80

```
gacgcgtctt aagaccatgt gagcaaaagg ccagcaaaag gccaggaacc gtaaaaaggc     60
cgcgttgctg gcgtttttcc ataggctccg cccccctgac gacgcatcac aaaaatcgac    120
gcgtcaagtc agaggtggcg aaacccgaca ggactataaa gataccaggc gtttccccct    180
ggaagctccc tcgtgcgctc tcctgttccg accctgccgc ttaccggata cctgtccgcc    240
tttctccctt cgggaagcgt ggcgctttct catagctcac gctgtaggta tctcagttcg    300
gtgtaggtcg ttcgctccaa gctgggctgt gtgcacgaac cccccgttca gcccgaccgc    360
tgcgccttat ccggtaacta tcgtcttgag tccaacccgg taagacacga cttatcgcca    420
ctggcagcag ccactggtaa caggattagc agagcgaggt atacaggcgg tgctacagag    480
ttcttgaagt ggtggcctaa ctacggctac actagaagaa cagtatttgg tatctgcgct    540
ctgctgaagc cagttacctt cggaaaaaga gttggtagct cttgatccgg caaacaaacc    600
accgctggta gcggtggttt ttttgtttgc aagcagcaga ttacgcgcag aaaaaaagga    660
tctcaagaag atcctttgat cttttctacg gggtctgacg cgtcagtgga acgaaaactc    720
acgttaaggg attttggtca tgagattatc aaaaaggatc ttcacctaga tccttttaaa    780
ttaaaaatga agttttaaat caatctaaag tatatatgag taaacttggt ctgacagtta    840
ccaatgctta atcagtgagg cacctatctc agcgatctgt ctatttcgtt catccatagt    900
tgcctgactc cccgtcgtgt agataactac gatacgggag ggcttaccat ctggccccag    960
tgctgcaatg ataccgcgag acccacgctc accggctcca gatttatcag caataaacca   1020
gccagccgga agggccgagc gtatacgtgg tcctgcaact ttatccgcct ccatccagtc   1080
tattaattgt tgccgggaag ctagagtaag tagttcgcca gttaatagtt tgcgcaacgt   1140
```

```
tgttgccatt gctacaggca tcgtggtgtc acgctcgtcg tttggtatgg cttcattcag   1200

ctccggttcc caacgatcaa gacgcgttac atgatccccc atgttgtgca aaaaagcggt   1260

tagctccttc ggtcctccga tcgttgtcag aagtaagttg gccgcagtgt tatcactcat   1320

ggttatggca gcactgcata attctcttac tgtcatgcca tccgtaagat gcttttctgt   1380

gactggtgag tactcaacca agtcattctg agaatagtgt atgcggcgac cgagttgctc   1440

ttgcccggcg tcaatacggg ataataccgc gccacatagc agaactttaa aagtgctcat   1500

cattggaaaa cgttcttcgg ggcgaaaact ctcaaggatc ttaccgctgt tgagatccag   1560

ttcgatgtaa cccacgcgtg ctcccaactg atcttcagca tcttttactt tcaccagcgt   1620

ttctgggtga gcaaaaacag gaaggcaaaa tgccgcaaaa aagggaataa gggcgacacg   1680

gaaatgctgg atgctcatac tcttcctttt tcaatattat tgaagcattt atcagggtta   1740

ttgtctcatg agcggataca tatttgaatg tatttagaaa aataaacaaa taggggttcc   1800

gcgcacattt ccccgaaaag tgccacctga cgtctaagaa accattatta tcatgacatt   1860

aacctataaa aataggcgta tcaacgcgtc ctgca                              1895
```

```
<210> SEQ ID NO 81
<211> LENGTH: 286
<212> TYPE: PRT
<213> ORGANISM: Artificial Sequence
<220> FEATURE:
<223> OTHER INFORMATION: Ampicillin resistance marker

<400> SEQUENCE: 81

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220
```

```
Ala Gly Trp Phe Ile Ala Asp Lys Ser Gly Ala Gly Thr Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285


<210> SEQ ID NO 82
<211> LENGTH: 286
<212> TYPE: PRT
<213> ORGANISM: Artificial Sequence
<220> FEATURE:
<223> OTHER INFORMATION: Ampicillin resistance marker

<400> SEQUENCE: 82

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Thr
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285


<210> SEQ ID NO 83
<211> LENGTH: 286
```

<212> TYPE: PRT
<213> ORGANISM: Artificial Sequence
<220> FEATURE:
<223> OTHER INFORMATION: Ampicillin resistance marker

<400> SEQUENCE: 83

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Thr Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```

<210> SEQ ID NO 84
<211> LENGTH: 286
<212> TYPE: PRT
<213> ORGANISM: Artificial Sequence
<220> FEATURE:
<223> OTHER INFORMATION: Ampicillin resistance marker

<400> SEQUENCE: 84

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45
```

```
Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Arg Ser Gln Ala Thr Met Asp Glu Arg Asn
            260                 265                 270

Arg Gln Ile Ala Glu Ile Gly Ala Ser Leu Ile Lys His Trp
        275                 280                 285
```

<210> SEQ ID NO 85
<211> LENGTH: 286
<212> TYPE: PRT
<213> ORGANISM: Artificial Sequence
<220> FEATURE:
<223> OTHER INFORMATION: Ampicillin resistance marker

<400> SEQUENCE: 85

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125
```

```
Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Thr Arg Asn
            260                 265                 270

Arg Gln Ile Ala Glu Ile Gly Ala Ser Leu Ile Lys His Trp
        275                 280                 285


<210> SEQ ID NO 86
<211> LENGTH: 286
<212> TYPE: PRT
<213> ORGANISM: Artificial Sequence
<220> FEATURE:
<223> OTHER INFORMATION: Ampicillin resistance marker

<400> SEQUENCE: 86

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205
```

```
Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Thr
            260                 265                 270

Arg Gln Ile Ala Glu Ile Gly Ala Ser Leu Ile Lys His Trp
        275                 280                 285


<210> SEQ ID NO 87
<211> LENGTH: 286
<212> TYPE: PRT
<213> ORGANISM: Artificial Sequence
<220> FEATURE:
<223> OTHER INFORMATION: Ampicillin resistance marker

<400> SEQUENCE: 87

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Arg Ile Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```

<210> SEQ ID NO 88
<211> LENGTH: 286
<212> TYPE: PRT
<213> ORGANISM: Artificial Sequence
<220> FEATURE:
<223> OTHER INFORMATION: Ampicillin resistance marker

<400> SEQUENCE: 88

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Glu
            260                 265                 270

Arg Val Ile Ala Glu Ile Gly Ala Ser Leu Ile Lys His Trp
        275                 280                 285
```

<210> SEQ ID NO 89
<211> LENGTH: 286
<212> TYPE: PRT
<213> ORGANISM: Artificial Sequence
<220> FEATURE:
<223> OTHER INFORMATION: Ampicillin resistance marker

<400> SEQUENCE: 89

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
```

```
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Asp Ala Ser Met Asp Glu Arg Asn
            260                 265                 270

Arg Gln Ile Ala Glu Ile Gly Ala Ser Leu Ile Lys His Trp
        275                 280                 285
```

<210> SEQ ID NO 90
<211> LENGTH: 441
<212> TYPE: DNA
<213> ORGANISM: Artificial Sequence
<220> FEATURE:
<223> OTHER INFORMATION: Gene block 1d

<400> SEQUENCE: 90

```
gcgttgctgg cgtttttcca taggcttcgc gcccctgacg agcatcacaa aaatcgacgc     60

tcaagtcaga ggacgcgtaa cccgacagga ctataaagat accaggcgtt tcccccctgga   120

agctccctcg tgcgctctcc tgttccgacc ctgccgctta ccggatacct gtccgccttt    180

ctcccttcgg gaagcgtggc gctttctcat agctcacgct gtaggtatct cagttcggtg    240

taggtcgttc gctccaagct gggctgtgtg cacgaacccc ccgttcagcc cgaccgctgc    300

gccttatccg gtaactatcg tcttgagtcc aacccggtaa gacacgactt atcgccactg    360

gcagcagcca ctggtaacag gattagcaga gcgaggtatg taggcggtgc tacagagttc    420

ttgaagtggt ggcctaacta c                                              441
```

<210> SEQ ID NO 91
<211> LENGTH: 443

<212> TYPE: DNA
<213> ORGANISM: Artificial Sequence
<220> FEATURE:
<223> OTHER INFORMATION: Gene block 1e

<400> SEQUENCE: 91

```
gcgttgctgg cgtttttcca taggctccgc ccccctgacg acgcatcaca aaaatcgacg     60

cgtcaagtca gaggtggcga aacccgacag gactataaag ataccaggcg tttccccctg    120

gaagctccct cgtgcgctct cctgttccga ccctgccgct taccggatac ctgtccgcct    180

ttctcccttc gggaagcgtg gcgctttctc atagctcacg ctgtaggtat ctcagttcgg    240

tgtaggtcgt tcgctccaag ctgggctgtg tgcacgaacc ccccgttcag cccgaccgct    300

gcgccttatc cggtaactat cgtcttgagt ccaacccggt aagacacgac ttatcgccac    360

tggcagcagc cactggtaac aggattagca gagcgaggta tgtaggcggt gctacagagt    420

tcttgaagtg gtggcctaac tac                                            443
```

<210> SEQ ID NO 92
<211> LENGTH: 443
<212> TYPE: DNA
<213> ORGANISM: Artificial Sequence
<220> FEATURE:
<223> OTHER INFORMATION: Gene block 1b

<400> SEQUENCE: 92

```
gcgttgctgg cgtttttcca taggctccgc ccccctgacg agcatcacaa aaatcgacgc     60

tcaagtcaga ggtggcgaaa cccgacagga ctataaagat accaggcgtt tccccctgga    120

agctccctcg tgcgctctcc tgttccgacc ctgccgctta ccggatacct gtccgccttt    180

ctcccttcgg gaagcgtggc gctttctcat agctcacgct gtaggtatct cagttcggtg    240

taggtcgttc gctccaagct acgcgtgtgt gcacgaaccc cccgttcacg cgtgaccgct    300

gcgccttatc cggtaactat cgtcttgagt ccaacccggt aagacacgac ttatcgccac    360

tggcagcagc cactggtaac aggattagca gagcgaggta tgtaggcggt gctacagagt    420

tcttgaagtg gtggcctaac tac                                            443
```

<210> SEQ ID NO 93
<211> LENGTH: 441
<212> TYPE: DNA
<213> ORGANISM: Artificial Sequence
<220> FEATURE:
<223> OTHER INFORMATION: Gene block 1c

<400> SEQUENCE: 93

```
gcgttgctgg cgtttttcca taggctccgc ccccctgacg agcatcacaa aaatcgacgc     60

tcaagtcaga ggtggcgaaa cccgacagga ctataaagat accaggcgtt tccccctgga    120

agctccctcg tgcgctctcc tgttccgacc cgacgcgtta ccggatacct gtccgccttt    180

ctcccttcgg gaagcgtggc gctttctcat agctcacgct gtaggtatct cagttgcgag    240

taggtcgttc gctccaagct gggctgtgtg cacgaacccc ccgttcagcc cgaccgctgc    300

gccttatccg gtaactatcg tcttgagtcc aacccggtaa gacacgactt atcgccactg    360

gcagcagcca ctggtaacag gattagcaga gcgaggtatg taggcggtgc tacagagttc    420

ttgaagtggt ggcctaacta c                                              441
```

<210> SEQ ID NO 94
<211> LENGTH: 444
<212> TYPE: DNA

<213> ORGANISM: Artificial Sequence
<220> FEATURE:
<223> OTHER INFORMATION: Gene block 1f

<400> SEQUENCE: 94
gcgttgctgg cgtttttcca taggctccgc ccccctgacg agcatcacaa aaatcgacgc 60
gtcaagtcag aggtggcgaa acccgacagg actataaaga taccaggcgt ttccccctgg 120
aagctccctc gtgcgctctc ctgttccgac cctgccgctt accggatacc tgtccgcctt 180
tctcccttcg ggaagcgtgg cgctttctca tagctcacgc tgtaggtatc tcagttcggt 240
gtaggtcgtt cgctccaagc tacgcgtgtg tgcacgaacc ccccgttcac gcgtgaccgc 300
tgcgccttat ccggtaacta tcgtcttgag tccaacccgg taagacacga cttatcgcca 360
ctggcagcag ccactggtaa caggattagc agagcgaggt atgtaggcgg tgctacagag 420
ttcttgaagt ggtggcctaa ctac 444

<210> SEQ ID NO 95
<211> LENGTH: 442
<212> TYPE: DNA
<213> ORGANISM: Artificial Sequence
<220> FEATURE:
<223> OTHER INFORMATION: Gene block 1g

<400> SEQUENCE: 95
gcgttgctgg cgtttttcca taggctccgc ccccctgacg agcatcacaa aaatcgacgc 60
gtcaagtcag aggtggcgaa acccgacagg actataaaga taccaggcgt ttccccctgg 120
aagctccctc gtgcgctctc ctgttccgac ccgacgcgtt accggatacc tgtccgcctt 180
tctcccttcg ggaagcgtgg cgctttctca tagctcacgc tgtaggtatc tcagttgcga 240
gtaggtcgtt cgctccaagc tgggctgtgt gcacgaaccc cccgttcagc ccgaccgctg 300
cgccttatcc ggtaactatc gtcttgagtc caacccggta agacacgact tatcgccact 360
ggcagcagcc actggtaaca ggattagcag agcgaggtat gtaggcggtg ctacagagtt 420
cttgaagtgg tggcctaact ac 442

<210> SEQ ID NO 96
<211> LENGTH: 467
<212> TYPE: DNA
<213> ORGANISM: Artificial Sequence
<220> FEATURE:
<223> OTHER INFORMATION: Gene block 2b

<400> SEQUENCE: 96
agttcttgaa gtggtggcct aactacggct acactagaag aacagtattt ggtatctgcg 60
ctctgctgaa gccagttacc ttcggaaaaa gagttggtag ctcttgatcc ggcaaacaaa 120
ccaccgctgg tagcggtggt ttttttgttt gcaagcagca gattacgcgc agaaaaaaag 180
gatctcaaga agatcctttg atcttttcta cggggtctga cgcgtcagtg gaacgaaaac 240
tcacgttaag ggattttggt catgagatta tcaaaaagga tcttcaccta gatcctttta 300
aattaaaaat gaagttttaa atcaatctaa agtatatatg agtaaacttg gtctgacagt 360
tagaaaaact catcgagcat caaatgaaac tgcaatttat tcatatcagg attatcaata 420
ccatattttt gaaaaagccg tttctgtaat gaaggagaaa actcacc 467

<210> SEQ ID NO 97
<211> LENGTH: 443
<212> TYPE: DNA
<213> ORGANISM: Artificial Sequence
<220> FEATURE:
<223> OTHER INFORMATION: Gene block 1n

<400> SEQUENCE: 97

```
gcgttgctgg cgtttttcca taggctccgc ccccctgacg acgcatcaca aaaatcgacg     60
cgtcaagtca gaggtggcga aacccgacag gactataaag ataccaggcg tttccccctg    120
gaagctccct cgtgcgctct cctgttccga ccctgccgct taccggatac ctgtccgcct    180
ttctcccttc gggaagcgtg gcgctttctc atagctcacg ctgtaggtat accagttcgg    240
tgtaggtcgt tcgctccaag ctgggctgtg tgcacgaacc ccccgttcag cccgaccgct    300
gcgccttatc cggtaactat cgtcttgagt ccaacccggt aagacacgac ttatcgccac    360
tggcagcagc cactggtaac aggattagca gagcgaggta tgtaggcggt gctacagagt    420
tcttgaagtg gtggcctaac tac                                            443
```

<210> SEQ ID NO 98
<211> LENGTH: 443
<212> TYPE: DNA
<213> ORGANISM: Artificial Sequence
<220> FEATURE:
<223> OTHER INFORMATION: Gene block 1o

<400> SEQUENCE: 98

```
gcgttgctgg cgtttttcca taggctccgc ccccctgacg acgcatcaca aaaatcgacg     60
cgtcaagtca gaggtggcga aacccgacag gactataaag ataccaggcg tttccccctg    120
gaagctccct cgtgcgctct cctgttccga ccctgccgct taccggatac ctgtccgcct    180
ttctcccttc gggaagcgtg gcgctttctc atagctcacg ctgtaggtat ctcagttcgg    240
tgtaggtcgt tcgctccaag ctgggctgtg tatacgaacc ccccgttcag cccgaccgct    300
gcgccttatc cggtaactat cgtcttgagt ccaacccggt aagacacgac ttatcgccac    360
tggcagcagc cactggtaac aggattagca gagcgaggta tgtaggcggt gctacagagt    420
tcttgaagtg gtggcctaac tac                                            443
```

<210> SEQ ID NO 99
<211> LENGTH: 443
<212> TYPE: DNA
<213> ORGANISM: Artificial Sequence
<220> FEATURE:
<223> OTHER INFORMATION: Gene block 1p

<400> SEQUENCE: 99

```
gcgttgctgg cgtttttcca taggctccgc ccccctgacg acgcatcaca aaaatcgacg     60
cgtcaagtca gaggtggcga aacccgacag gactataaag ataccaggcg tttccccctg    120
gaagctccct cgtgcgctct cctgttccga ccctgccgct taccggatac ctgtccgcct    180
ttctcccttc gggaagcgtg gcgctttctc atagctcacg ctgtaggtat ctcagttcgg    240
tgtaggtcgt tcgctccaag ctgggctgtg tgcacgaacc ccccgttcag cccgaccgct    300
gcgccttatc cggtaactat cgtcttgagt ccaacccggt aagacacgac ttatcgccac    360
tggcagcagc cactggtaac aggattagca gagcgaggta tacaggcggt gctacagagt    420
tcttgaagtg gtggcctaac tac                                            443
```

<210> SEQ ID NO 100
<211> LENGTH: 1557
<212> TYPE: DNA
<213> ORGANISM: Artificial Sequence
<220> FEATURE:

<223> OTHER INFORMATION: seAP coding sequence

<400> SEQUENCE: 100

```
atgttgctgc tcctgcttct tcttgggctt aggcttcaac ttagtcttgg gataattccg     60
gttgaagaag agaaccctga tttttggaat agagaggccg ccgaagcctt gggtgccgct    120
aagaagctgc aacctgcaca aactgctgcg aaaaacctta tcatcttcct tggtgatgga    180
atgggagtgt ctacagtgac cgctgcgcgc atcctcaagg gacagaagaa ggacaaattg    240
gggccagaga tcccgctggc aatggacaga tttccttatg tggccctgag caagacttac    300
aatgtcgaca agcacgtccc cgattcaggg gctacagcta cagcatatct gtgcggtgta    360
aagggcaatt tccagaccat cggcctcagc gccgctgcaa gattcaatca atgcaacacc    420
actcgaggga acgaagtgat ctcagtgatg aacagagcca aaaaggccgg aaagtctgtt    480
ggtgtcgtga cgactacccg cgtgcagcat gctagccctg ctggtacata cgctcataca    540
gtcaaccgga actggtacag cgacgccgac gttcccgcgt cagcacgcca agagggttgc    600
caggatattg caactcaact tatcagcaac atggatattg atgtgatttt gggaggagga    660
cgcaagtata tgtttaggat gggcacccca gatccagaat atccagacga ttactcacaa    720
gggggcactc ggctggacgg caagaacctg gttcaggaat ggcttgccaa acgacaggga    780
gcgaggtatg tctggaatag gactgagctt atgcaagcat ccctcgaccc ctccgtaacc    840
catctgatgg gactctttga gcctggggat atgaagtatg aaattcaccg cgactccaca    900
ttggacccat cactgatgga gatgacagag gccgcacttc gcctcctgtc acggaaccct    960
cgaggcttct ttctgttcgt tgaaggaggg aggatagacc acggacacca cgaaagtagg   1020
gcctatagag cactcacgga aaccattatg ttcgacgacg ctatcgaaag ggctggtcag   1080
cttacctctg aggaggacac cctctccctg gtgacagccg accattccca cgtgttcagc   1140
ttcggcggct acccacttag gggtcctctc atttttggac tggcgccagg caaagcccgg   1200
gataggaagg cttacaccgt gttgctctac gggaacggtc ccggctacgt cctgaaggac   1260
ggtgcgaggc ccgacgtcac agagagcgag tctggaagcc ctgagtatag gcaacaatca   1320
gcagtacccc tcgacgagga gactcacgca ggcgaggatg tcgctgtgtt cgccagaggg   1380
ccacaggccc acctggtcca cggagtgcaa gagcaaactt tcatcgctca cgtcatggca   1440
ttcgccgctt gccttgagcc ctacacggca tgtgacctgg cccctccggc agggacaact   1500
gacgctgctc acccaggtta cagtcgcgtg ggcgctgctg gcaggttcga gcagacc      1557
```

<210> SEQ ID NO 101
<211> LENGTH: 1968
<212> TYPE: DNA
<213> ORGANISM: Artificial Sequence
<220> FEATURE:
<223> OTHER INFORMATION: GS selection marker

<400> SEQUENCE: 101

```
ctgtggaatg tgtgtcagtt agggtgtgga aagtccccag gctccccagc aggcagaagt     60
atgcaaagca tgcatctcaa ttagtcagca accaggtgtg gaaagtcccc aggctcccca    120
gcaggcagaa gtatgcaaag catgcatctc aattagtcag caaccatagt cccgccccta    180
actccgccca tcccgcccct aactccgccc agttccgccc attctccgcc ccatggctga    240
ctaatttttt ttatttatgc agaggccgag gccgcctctg cctctgagct attccagaag    300
tagtgaggag gcttttttgg aggcctaggc ttttgcaaaa agctcccggg agcttgtata    360
tccattttcg gatctgatca gcacgtgttg acaattaatc atcggcatag tatatcggca    420
```

```
tagtataata cgacaaggtg aggcaacagg tgagtaagcg cagttgtcgt ctcttgcggt    480
gccgttgctg gttctcacac cttttaggtc tgttctcgtc ttccgttctg actctctctt    540
tttcgttgca ggccatggcc acctcagcaa gttcccactt gaacaaaaac atcaagcaaa    600
tgtacttgtg cctgccccag ggtgagaaag tccaagccat gtatatctgg gttgatggta    660
ctggagaagg actgcgctgc aaaacccgca ccctggactg tgagcccaag tgtgtagaag    720
agttacctga gtggaatttt gatggctcta gtacctttca gtctgagggc tccaacagtg    780
atatgtatct cagccctgtt gccatgtttc gggacccctt ccgcagagat cccaacaagc    840
tggtgttctg tgaagttttc aagtacaacc ggaagcctgc agagaccaat ttaaggcact    900
cgtgtaaacg gataatggac atggtgagca accagcaccc ctggtttgga atggaacagg    960
agtacactct gatgggaaca gatgggcacc cttttggttg gccttccaat ggctttcctg   1020
ggccccaagg tccgtattac tgtggtgtgg gcgcagacaa agcctatggc agggatatcg   1080
tggaggctca ctaccgcgcc tgcttgtatg ctggggtcaa gattacagga acaaatgcag   1140
aggtcatgcc tgcccagtgg gagttccaaa taggaccctg tgaaggaatc cgcatgggag   1200
atcatctctg ggtggcccgt ttcatcttgc atcgagtatg tgaagacttt ggggtaatag   1260
caacctttga ccccaagccc attcctggga actggaatgg tgcaggctgc cataccaact   1320
ttagcaccaa ggccatgcgg gaggagaatg gtctgaagca catcgaggag gccatcgaga   1380
aactaagcaa gcggcaccgg taccacattc gagcctacga tcccaagggg ggcctggaca   1440
atgcccgtcg tctgactggg ttccacgaaa cgtccaacat caacgacttt tctgctggtg   1500
tcgccaatcg cagtgccagc atccgcattc cccggactgt cggccaggag aagaaaggtt   1560
actttgaaga ccgccgcccc tctgccaatt gtgacccctt tgcagtgaca gaagccatcg   1620
tccgcacatg ccttctcaat gagactggcg acgagccctt ccaatacaaa aactaagcta   1680
agcacttcgt ggccgaggag caggactgac acgtgctacg agatttcgat tccaccgccg   1740
ccttctatga aaggttgggc ttcggaatcg ttttccggga cgccggctgg atgatcctcc   1800
agcgcgggga tctcatgctg gagttcttcg cccaccccaa cttgtttatt gcagcttata   1860
atggttacaa ataaagcaat agcatcacaa atttcacaaa taaagcattt ttttcactgc   1920
attctagttg tggtttgtcc aaactcatca atgtatctta tcatgtct                1968
```

```
<210> SEQ ID NO 102
<211> LENGTH: 10
<212> TYPE: PRT
<213> ORGANISM: Artificial Sequence
<220> FEATURE:
<223> OTHER INFORMATION: N-terminal amino acids kanamycin resistance
      marker

<400> SEQUENCE: 102

Met Ser His Ile Gln Arg Glu Thr Ser Cys
1               5                   10


<210> SEQ ID NO 103
<211> LENGTH: 11
<212> TYPE: PRT
<213> ORGANISM: Artificial Sequence
<220> FEATURE:
<223> OTHER INFORMATION: N-terminal amino acidskanamycin resistance
      marker variant

<400> SEQUENCE: 103

Met Ser His Ile Gln Thr Arg Glu Thr Ser Cys
```

1 5 10

<210> SEQ ID NO 104
<211> LENGTH: 11
<212> TYPE: PRT
<213> ORGANISM: Artificial Sequence
<220> FEATURE:
<223> OTHER INFORMATION: N-terminal amino acidskanamycin resistance marker variant

<400> SEQUENCE: 104

Met Ser His Ile Gln Arg Glu Thr Arg Ser Cys
1 5 10

<210> SEQ ID NO 105
<211> LENGTH: 816
<212> TYPE: DNA
<213> ORGANISM: Artificial Sequence
<220> FEATURE:
<223> OTHER INFORMATION: Kanamycin resistance marker wt CDS

<400> SEQUENCE: 105
atgagccata ttcaacggga aacgtcttgc tctaggccgc gattaaattc caacatggat 60
gctgatttat atgggtataa atgggctcgc gataatgtcg ggcaatcagg tgcgacaatc 120
tatcgattgt atgggaagcc cgatgcgcca gagttgtttc tgaaacatgg caaaggtagc 180
gttgccaatg atgttacaga tgagatggtc agactaaact ggctgacgga atttatgcct 240
cttccgacca tcaagcattt tatccgtact cctgatgatg catggttact caccactgcg 300
atccctggga aaacagcatt ccaggtatta gaagaatatc ctgattcagg tgaaaatatt 360
gttgatgcgc tggcagtgtt cctgcgccgg ttgcattcga ttcctgtttg taattgtcct 420
tttaacagcg atcgcgtatt tcgtctcgct caggcgcaat cacgaatgaa taacggtttg 480
gttgatgcga gtgattttga tgacgagcgt aatggctggc ctgttgaaca agtctggaaa 540
gaaatgcata aacttttgcc attctcaccg gattcagtcg tcactcatgg tgatttctca 600
cttgataacc ttatttttga cgaggggaaa ttaataggtt gtattgatgt tggacgagtc 660
ggaatcgcag accgatacca ggatcttgcc atcctatgga actgcctcgg tgagttttct 720
ccttcattac agaaacggct ttttcaaaaa tatggtattg ataatcctga tatgaataaa 780
ttgcagtttc atttgatgct cgatgagttt ttctaa 816

<210> SEQ ID NO 106
<211> LENGTH: 858
<212> TYPE: DNA
<213> ORGANISM: Artificial Sequence
<220> FEATURE:
<223> OTHER INFORMATION: Ampicillin resistance marker wt CDS

<400> SEQUENCE: 106
atgagtattc aacatttccg tgtcgccctt attccctttt ttgcggcatt ttgccttcct 60
gtttttgctc acccagaaac gctggtgaaa gtaaaagatg ctgaagatca gttgggagca 120
cgagtgggtt acatcgaact ggatctcaac agcggtaaga tccttgagag ttttcgcccc 180
gaagaacgtt ttccaatgat gagcactttt aaagttctgc tatgtggcgc ggtattatcc 240
cgtattgacg ccgggcaaga gcaactcggt cgccgcatac actattctca gaatgacttg 300
gttgagtact caccagtcac agaaaagcat cttacggatg gcatgacagt aagagaatta 360
tgcagtgctg ccataaccat gagtgataac actgcggcca acttacttct gacaacgatc 420
ggaggaccga aggagctaac cgcttttttg cacaacatgg gggatcatgt aactcgcctt 480
gatcgttggg aaccggagct gaatgaagcc ataccaaacg acgagcgtga caccacgatg 540
cctgtagcaa tggcaacaac gttgcgcaaa ctattaactg gcgaactact tactctagct 600
tcccggcaac aattaataga ctggatggag gcggataaag ttgcaggacc acttctgcgc 660
tcggcccttc cggctggctg gtttattgct gataaatctg gagccggtga gcgtgggtct 720
cgcggtatca ttgcagcact ggggccagat ggtaagccct cccgtatcgt agttatctac 780
acgacgggga gtcaggcaac tatggatgaa cgaaatagac agatcgctga gataggtgcc 840
tcactgatta agcattgg 858

<210> SEQ ID NO 107
<211> LENGTH: 375
<212> TYPE: DNA
<213> ORGANISM: Artificial Sequence
<220> FEATURE:
<223> OTHER INFORMATION: Zeocin resistance marker wt CDS

<400> SEQUENCE: 107
atggccaagt tgaccagtgc cgttccggtg ctcaccgcgc gcgacgtcgc cggagcggtc 60
gagttctgga ccgaccggct cgggttctcc cgggacttcg tggaggacga cttcgccggt 120
gtggtccggg acgacgtgac cctgttcatc agcgcggtcc aggaccaggt ggtgccggac 180
aacaccctgg cctgggtgtg ggtgcgcggc ctggacgagc tgtacgccga gtggtcggag 240
gtcgtgtcca cgaacttccg ggacgcctcc gggccggcca tgaccgagat cggcgagcag 300
ccgtgggggc gggagttcgc cctgcgcgac ccggccggca actgcgtgca cttcgtggcc 360
gaggagcagg actga 375

<210> SEQ ID NO 108
<211> LENGTH: 660
<212> TYPE: DNA
<213> ORGANISM: Artificial Sequence
<220> FEATURE:
<223> OTHER INFORMATION: Chloramphenicol resistance marker wt CDS

<400> SEQUENCE: 108
atggagaaaa aaatcactgg atataccacc gttgatatat cccaatggca tcgtaaagaa 60
cattttgagg catttcagtc agttgctcaa tgtacctata accagaccgt tcagctggat 120
attacggcct ttttaaagac cgtaaagaaa aataagcaca agttttatcc ggcctttatt 180
cacattcttg cccgcctgat gaatgctcat ccggaatttc gtatggcaat gaaagacggt 240
gagctggtga tatgggatag tgttcaccct tgttacaccg ttttccatga gcaaactgaa 300
acgttttcat cgctctggag tgaataccac gacgatttcc ggcagtttct acacatatat 360
tcgcaagatg tggcgtgtta cggtgaaaac ctggcctatt tccctaaagg gtttattgag 420
aatatgtttt tcgtctcagc caatccctgg gtgagtttca ccagttttga tttaaacgtg 480
gccaatatgg acaacttctt cgcccccgtt ttcaccatgg gcaaatatta tacgcaaggc 540
gacaaggtgc tgatgccgct ggcgattcag gttcatcatg ccgtttgtga tggcttccat 600
gtcggcagaa tgcttaatga attacaacag tactgcgatg agtggcaggg cggggcgtaa 660

<210> SEQ ID NO 109
<211> LENGTH: 351
<212> TYPE: DNA
<213> ORGANISM: Artificial Sequence
<220> FEATURE:
<223> OTHER INFORMATION: LacZalpha marker

<400> SEQUENCE: 109

```
atgaccatga ttacgccaag cttgcatgcc tgcaggttta aacagtcgac tctagactta     60

attaaggatc cggcgcgccc ccgggtaccg agctcgaatt cactggccgt cgttttacaa    120

cgtcgtgact gggaaaaccc tggcgttacc caacttaatc gccttgcagc acatccccct    180

ttcgccagct ggcgtaatag cgaagaggcc cgcaccgatc gcccttccca acagttgcgc    240

agcctgaatg gcgaatggcg cctgatgcgg tattttctcc ttacgcatct gtgcggtatt    300

tcacaccgca tatggtgcac tctcagtaca atctgctctg atgccgcata g             351
```

<210> SEQ ID NO 110
<211> LENGTH: 861
<212> TYPE: DNA
<213> ORGANISM: Artificial Sequence
<220> FEATURE:
<223> OTHER INFORMATION: Ampicillin resistance marker

<400> SEQUENCE: 110

```
atgagcatcc agcatttccg tgtcgccctt attccctttt ttgcggcatt ttgccttcct     60

gtttttgctc acccagaaac gctggtgaaa gtaaaagatg ctgaagatca gttgggagca    120

cgcgtgggtt acatcgaact ggatctcaac agcggtaaga tccttgagag ttttcgcccc    180

gaagaacgtt ttccaatgat gagcactttt aaagttctgc tatgtggcgc ggtattatcc    240

cgtattgacg ccgggcaaga gcaactcggt cgccgcatac actattctca gaatgacttg    300

gttgagtact caccagtcac agaaaagcat cttacggatg gcatgacagt aagagaatta    360

tgcagtgctg ccataaccat gagtgataac actgcggcca acttacttct gacaacgatc    420

ggaggaccga aggagctaac cgcttttttg cacaacatgg gggatcatgt aacgcgtctt    480

gatcgttggg aaccggagct gaatgaagcc ataccaaacg acgagcgtga caccacgatg    540

cctgtagcaa tggcaacaac gttgcgcaaa ctattaactg gcgaactact tactctagct    600

tcccggcaac aattaataga ctggatggag gcggataaag ttgcaggacc acttctgcgc    660

tcggcccttc cggctggctg gtttattgct gataaatctg gagccggtac gcgtgggtct    720

cgcggtatca ttgcagcact ggggccagat ggtaagccct cccgtatcgt agttatctac    780

acgacgggga gtcaggcaac tatggatgaa cgaaatagac agatcgctga gataggtgcc    840

tcactgatta agcattggta a                                              861
```

<210> SEQ ID NO 111
<211> LENGTH: 861
<212> TYPE: DNA
<213> ORGANISM: Artificial Sequence
<220> FEATURE:
<223> OTHER INFORMATION: Ampicillin resistance marker

<400> SEQUENCE: 111

```
atgagcatcc agcatttccg tgtcgccctt attccctttt ttgcggcatt ttgccttcct     60

gtttttgctc acccagaaac gctggtgaaa gtaaaagatg ctgaagatca gttgggagca    120

cgcgtgggtt acatcgaact ggatctcaac agcggtaaga tccttgagag ttttcgcccc    180

gaagaacgtt ttccaatgat gagcactttt aaagttctgc tatgtggcgc ggtattatcc    240

cgtattgacg ccgggcaaga gcaactcggt cgccgcatac actattctca gaatgacttg    300

gttgagtact caccagtcac agaaaagcat cttacggatg gcatgacagt aagagaatta    360

tgcagtgctg ccataaccat gagtgataac actgcggcca acttacttct gacaacgatc    420

ggaggaccga aggagctaac cgcttttttg cacaacatgg gggatcatgt aacgcgtctt    480
```

```
gatcgttggg aaccggagct gaatgaagcc ataccaaacg acgagcgtga caccacgatg    540

cctgtagcaa tggcaacaac gttgcgcaaa ctattaactg gcgaactact tactctagct    600

tcccggcaac aattaataga ctggatggag gcggataaag ttgcaggacc acttctgcgc    660

tcggcccttc cggctggctg gtttattgct gataaatctg gagccggtga gcgtgggacg    720

cgtggtatca ttgcagcact ggggccagat ggtaagccct cccgtatcgt agttatctac    780

acgacgggga gtcaggcaac tatggatgaa cgaaatagac agatcgctga gataggtgcc    840

tcactgatta agcattggta a                                              861
```

<210> SEQ ID NO 112
<211> LENGTH: 861
<212> TYPE: DNA
<213> ORGANISM: Artificial Sequence
<220> FEATURE:
<223> OTHER INFORMATION: Ampicillin resistance marker

<400> SEQUENCE: 112

```
atgagcatcc agcatttccg tgtcgccctt attccctttt ttgcggcatt ttgccttcct     60

gtttttgctc acccagaaac gctggtgaaa gtaaaagatg ctgaagatca gttgggagca    120

cgcgtgggtt acatcgaact ggatctcaac agcggtaaga tccttgagag ttttcgcccc    180

gaagaacgtt ttccaatgat gagcactttt aaagttctgc tatgtggcgc ggtattatcc    240

cgtattgacg ccgggcaaga gcaactcggt cgccgcatac actattctca gaatgacttg    300

gttgagtact caccagtcac agaaaagcat cttacggatg gcatgacagt aagagaatta    360

tgcagtgctg ccataaccat gagtgataac actgcggcca acttacttct gacaacgatc    420

ggaggaccga aggagctaac cgcttttttg cacaacatgg gggatcatgt aacgcgtctt    480

gatcgttggg aaccggagct gaatgaagcc ataccaaacg acgagcgtga caccacgatg    540

cctgtagcaa tggcaacaac gttgcgcaaa ctattaactg gcgaactact tactctagct    600

tcccggcaac aattaataga ctggatggag gcggataaag ttgcaggacc acttctgcgc    660

tcggcccttc cggctggctg gtttattgct gataaatctg gagccggtga gcgtgggtct    720

cgcggtatca ttgcagcact ggggccagat ggtaagccca cgcgtatcgt agttatctac    780

acgacgggga gtcaggcaac tatggatgaa cgaaatagac agatcgctga gataggtgcc    840

tcactgatta agcattggta a                                              861
```

<210> SEQ ID NO 113
<211> LENGTH: 861
<212> TYPE: DNA
<213> ORGANISM: Artificial Sequence
<220> FEATURE:
<223> OTHER INFORMATION: Ampicillin resistance marker

<400> SEQUENCE: 113

```
atgagcatcc agcatttccg tgtcgccctt attccctttt ttgcggcatt ttgccttcct     60

gtttttgctc acccagaaac gctggtgaaa gtaaaagatg ctgaagatca gttgggagca    120

cgcgtgggtt acatcgaact ggatctcaac agcggtaaga tccttgagag ttttcgcccc    180

gaagaacgtt ttccaatgat gagcactttt aaagttctgc tatgtggcgc ggtattatcc    240

cgtattgacg ccgggcaaga gcaactcggt cgccgcatac actattctca gaatgacttg    300

gttgagtact caccagtcac agaaaagcat cttacggatg gcatgacagt aagagaatta    360

tgcagtgctg ccataaccat gagtgataac actgcggcca acttacttct gacaacgatc    420
```

```
ggaggaccga aggagctaac cgcttttttg cacaacatgg gggatcatgt aacgcgtctt    480

gatcgttggg aaccggagct gaatgaagcc ataccaaacg acgagcgtga caccacgatg    540

cctgtagcaa tggcaacaac gttgcgcaaa ctattaactg gcgaactact tactctagct    600

tcccggcaac aattaataga ctggatggag gcggataaag ttgcaggacc acttctgcgc    660

tcggcccttc cggctggctg gtttattgct gataaatctg gagccggtga gcgtgggtct    720

cgcggtatca ttgcagcact ggggccagat ggtaagccct cccgtatcgt agttatctac    780

acgacgcgta gtcaggcaac tatggatgaa cgaaatagac agatcgctga gataggtgcc    840

tcactgatta agcattggta a                                              861
```

<210> SEQ ID NO 114
<211> LENGTH: 861
<212> TYPE: DNA
<213> ORGANISM: Artificial Sequence
<220> FEATURE:
<223> OTHER INFORMATION: Ampicillin resistance marker

<400> SEQUENCE: 114

```
atgagcatcc agcatttccg tgtcgccctt attccctttt ttgcggcatt ttgccttcct     60

gtttttgctc acccagaaac gctggtgaaa gtaaaagatg ctgaagatca gttgggagca    120

cgcgtgggtt acatcgaact ggatctcaac agcggtaaga tccttgagag ttttcgcccc    180

gaagaacgtt ttccaatgat gagcactttt aaagttctgc tatgtggcgc ggtattatcc    240

cgtattgacg ccgggcaaga gcaactcggt cgccgcatac actattctca gaatgacttg    300

gttgagtact caccagtcac agaaaagcat cttacggatg gcatgacagt aagagaatta    360

tgcagtgctg ccataaccat gagtgataac actgcggcca acttacttct gacaacgatc    420

ggaggaccga aggagctaac cgcttttttg cacaacatgg gggatcatgt aacgcgtctt    480

gatcgttggg aaccggagct gaatgaagcc ataccaaacg acgagcgtga caccacgatg    540

cctgtagcaa tggcaacaac gttgcgcaaa ctattaactg gcgaactact tactctagct    600

tcccggcaac aattaataga ctggatggag gcggataaag ttgcaggacc acttctgcgc    660

tcggcccttc cggctggctg gtttattgct gataaatctg gagccggtga gcgtgggtct    720

cgcggtatca ttgcagcact ggggccagat ggtaagccct cccgtatcgt agttatctac    780

acgacgggga gtcaggcaac tatggatacg cgtaatagac agatcgctga gataggtgcc    840

tcactgatta agcattggta a                                              861
```

<210> SEQ ID NO 115
<211> LENGTH: 861
<212> TYPE: DNA
<213> ORGANISM: Artificial Sequence
<220> FEATURE:
<223> OTHER INFORMATION: Ampicillin resistance marker

<400> SEQUENCE: 115

```
atgagcatcc agcatttccg tgtcgccctt attccctttt ttgcggcatt ttgccttcct     60

gtttttgctc acccagaaac gctggtgaaa gtaaaagatg ctgaagatca gttgggagca    120

cgcgtgggtt acatcgaact ggatctcaac agcggtaaga tccttgagag ttttcgcccc    180

gaagaacgtt ttccaatgat gagcactttt aaagttctgc tatgtggcgc ggtattatcc    240

cgtattgacg ccgggcaaga gcaactcggt cgccgcatac actattctca gaatgacttg    300

gttgagtact caccagtcac agaaaagcat cttacggatg gcatgacagt aagagaatta    360

tgcagtgctg ccataaccat gagtgataac actgcggcca acttacttct gacaacgatc    420
```

```
ggaggaccga aggagctaac cgctttttg cacaacatgg gggatcatgt aacgcgtctt    480

gatcgttggg aaccggagct gaatgaagcc ataccaaacg acgagcgtga caccacgatg    540

cctgtagcaa tggcaacaac gttgcgcaaa ctattaactg gcgaactact tactctagct    600

tcccggcaac aattaataga ctggatggag gcggataaag ttgcaggacc acttctgcgc    660

tcggcccttc cggctggctg gtttattgct gataaatctg gagccggtga gcgtgggtct    720

cgcggtatca ttgcagcact ggggccagat ggtaagccct cccgtatcgt agttatctac    780

acgacgggga gtcaggcaac tatggatgaa cgaacgcgtc agatcgctga gataggtgcc    840

tcactgatta agcattggta a                                               861

<210> SEQ ID NO 116
<211> LENGTH: 861
<212> TYPE: DNA
<213> ORGANISM: Artificial Sequence
<220> FEATURE:
<223> OTHER INFORMATION: Ampicillin resistance marker

<400> SEQUENCE: 116

atgagcatcc agcatttccg tgtcgccctt attccctttt ttgcggcatt ttgccttcct     60

gtttttgctc acccagaaac gctggtgaaa gtaaaagatg ctgaagatca gttgggagca    120

cgcgtgggtt acatcgaact ggatctcaac agcggtaaga tccttgagag ttttcgcccc    180

gaagaacgtt ttccaatgat gagcactttt aaagttctgc tatgtggcgc ggtattatcc    240

cgtattgacg ccgggcaaga gcaactcggt cgccgcatac actattctca gaatgacttg    300

gttgagtact caccagtcac agaaaagcat cttacggatg gcatgacagt aagagaatta    360

tgcagtgctg ccataaccat gagtgataac actgcggcca acttacttct gacaacgatc    420

ggaggaccga aggagctaac cgctttttg cacaacatgg gggatcatgt aacgcgtctt    480

gatcgttggg aaccggagct gaatgaagcc ataccaaacg acgagcgtga caccacgatg    540

cctgtagcaa tggcaacaac gttgcgcaaa ctattaactg gcgaactact tactctagct    600

tcccggcaac aattaataga ctggatggag gcggataaag ttgcaggacc acttctgcgc    660

tcggcccttc cggctggctg gtttattgct gataaatctg gagccggtga gcgtgggtct    720

cgcggtatca ttgcagcact ggggccagat ggtaagccct cccgtatcgt agttatctac    780

acgacgggga gtcaggcaac tatggatgaa cgagaacgcg tgatcgctga gataggtgcc    840

tcactgatta agcattggta a                                               861

<210> SEQ ID NO 117
<211> LENGTH: 443
<212> TYPE: DNA
<213> ORGANISM: Artificial sequence
<220> FEATURE:
<223> OTHER INFORMATION: Gene block 1i

<400> SEQUENCE: 117

gcgttgctgg cgtttttcca taggctccgc ccccctgacg acgcatcaca aaaatcgacg     60

cgtcaagtca gaggtggcga aacccgacag gactataaag ataccaggcg tttccccctg    120

gaagctccct cgtgcgctct cctgttccga ccctgccgct taccggatac ctgtccgcct    180

ttctcccttc gggaagcgtg gcgctttctc atagctcacg ctgtaggtat ctcagttcgg    240

tgtaggtcgt tcgctccaag ctgggctgtg tgcacgaacc ccccgttcag cccgaccgct    300

gcgccttatc cggtaactat cgtcttgagt ccaacccggt aagacacgac ttatcgcgac    360
```

-continued

```
tggcagcagc cacgcgtaac aggattagca gagcgaggta tgtaggcggt gctacagagt    420

tcttgaagtg gtggcctaac tac                                            443


<210> SEQ ID NO 118
<211> LENGTH: 444
<212> TYPE: DNA
<213> ORGANISM: Artificial sequence
<220> FEATURE:
<223> OTHER INFORMATION: Gene block 11

<400> SEQUENCE: 118

gcgttgctgg cgtttttcca taggctccgc ccccctgacg acgcatcaca aaaatcgacg     60

cgtcaagtca gaggtggcga aacccgacag gactataaag ataccaggcg tttccccctg    120

gaagctccct cgtgcgctct cctgttccga ccctgccgct taccggatac ctgtccgcct    180

ttctcccttc gggaagcgtg gcgctttctc atagctcacg ctgtaggtat ctcagttcgg    240

tgtaggtcgt tcgctccaag ctgggctgtg tgcacgaacc ccccgttcag cccgaccgct    300

gcgccttatc cggtaactat cgtcttgagt ccaacacgcg taagacacga cttatcgcca    360

ctggcagcag ccactggtaa caggattagc agagcgaggt atgtaggcgg tgctacagag    420

ttcttgaagt ggtggcctaa ctac                                           444
```

SELF-IMMOLATIVE PLASMID BACKBONE

FIELD OF THE INVENTION

The invention is in the field of polynucleotides and their production. The invention relates to a method for separating a polynucleotide insert from a polynucleotide vector backbone. The backbone has a plurality of cleavage sites distributed such that the backbone is converted into fragments when the sites are cleaved. This allows straightforward separation of the insert from the backbone. The invention also relates to backbones for use in such a method, and to plasmids and kits comprising such backbones.

BACKGROUND ART

Some uses of polynucleotides such as DNA require that a DNA fragment of interest is preserved and purified while other fragments are not needed and therefore are to be discarded. This can be the case when high purity polynucleotides are required, or when high efficiency of polynucleotide handling is required where contaminations would reduce handling efficiency. Separation of polynucleotides with a desired sequence from undesired polynucleotides is an essential, common process that is routinely carried out in molecular biology. Typically a fragment of interest (FOI) is present in a vector which is propagated in a bacterium. When this FOI is needed for later use, it needs to be separated from the remainder of the vector, which is generally a bacterial sequence. This time consuming effort requires molecular cloning activities, and is required to optimize the results of any follow-up experiment carried out with the purified polynucleotide.

In conventional purification of an insert from a vector, typically, restriction enzymes are used that allow the polynucleotide to be digested resulting in two fragments: a desired fragment and an unwanted fragment. After the actual digestion reaction has been carried out, the reaction mixture is loaded on an agarose gel to separate the fragments based on their size-determined difference in migration, and the desired fragment is subsequently collected from the agarose gel by cutting out the proper gel piece. The insert is then purified from the agarose gel material by centrifugation and precipitation, often using specific gel-dissolving solutions. While it is a routine process, this protocol is cumbersome and time consuming, which can lead to lower yields of desired fragments than theoretically possible. Additionally, preparation of desired polynucleotide often is further complicated when the size difference between the desired fragment and the undesired fragment is small, for in that case a more specific digestion protocol needs to be developed and carried out. Thus there is a need for a system that limits the amount of steps.

Besides common cloning activities, large scale polynucleotide isolations also often require removal of undesired polynucleotide fragments. For instance, for gene therapy applications significant amounts of DNA are desired from which part of the plasmid is removed out of safety concerns (antibiotic resistance markers [New Generation of Plasmid Backbones Devoid of Antibiotic Resistance Marker for Gene Therapy Trials. G Vandermeulen et al., Mol Therapy 2011 19, 1942-1949.], induced inflammatory responses [An araC-controlled bacterial cre expression system to produce DNA minicircle vectors for nuclear and mitochondrial gene therapy. B W Bigger et al., J Biol Chem. (2001) 276, 23018-23027.]), or because it negatively affects gene performance. Thus extensive research has been devoted to develop DNA material in which parts of a plasmid are removed. For example the resistance marker can be removed (see above Vandermeulen et al,) or both the resistance marker(s) as well as the genetic material that is essential to produce the plasmid in a microorganism can be removed. DNA fragments devoid of bacterial selection markers and/or all bacterial backbone sequences also are known to improve the expression of the eukaryotic gene that is to be expressed in a cultured mammalian host cell.

Currently, specific bacterial cell hosts are used to generate miniplasmid DNA. Following the production of a plasmid it is opened inside the cell with a specific enzyme. After removal of undesired sequences it is recicularised to form a miniplasmid. The DNA that is obtained after opening the bacterial cells needs to be purified from original full size plasmids and DNA debris. Combining efficient in vitro isolation of a desired DNA fragment with degradation and elimination of the backbone offers a simplification and an improvement of the process.

An improved method for separating polynucleotide fragments of interest from unwanted sections of polynucleotide is highly desired, for instance to facilitate isolation of an insert from a vector backbone. Polynucleotides for use in such improved methods are also desired.

SUMMARY OF THE INVENTION

The invention relates to a backbone for use in a vector, primed to allow the backbone to be degraded into small fragments by using cleavage means (e.g. restriction enzymes), while leaving the insert of the vector intact. The cleavage sites in the backbone are separated in such a way that the backbone is divided into small fragments. Such cleavage sites are not present in the insert. As a result, treatment of the vector backbone with for example the appropriate restriction enzymes will leave the insert as the sole polynucleotide fragment of considerable length. This enables easy separation between the desired fragment and the undesired backbone debris.

Accordingly, in a first aspect the invention provides a method for separating a polynucleotide insert from a polynucleotide vector backbone, the method comprising the steps of i) providing a recombinant polynucleotide vector comprising the insert and the vector backbone, wherein the vector backbone comprises a first plurality of cleavage sites that divide the vector backbone into fragments having a length of at most 1000 bp;
ii) contacting the recombinant vector with cleavage means capable of specifically cleaving the first plurality of cleavage sites to produce backbone fragments; and optionally,
iii) separating the insert from the backbone fragments of step ii).

In preferred embodiments the separation of step iii uses a technique selected from a spin column, a size exclusion column, and solid phase reversible immobilization (SPRI). In preferred embodiments the cleavage means are selected from the group consisting of a restriction enzyme, an RNA-guided DNA endonuclease enzyme, a sequence-specific nuclease, sequence-specific ultrasonication, a sequence-specific oxidative small molecule such as bleomycin, and a sequence-specific hydrolyzing small molecule such as a lanthanide complex. In more preferred embodiments the cleavage sites are restriction endonuclease recognition sites. Preferably, the cleavage means comprise 3, 2, or 1 species of restriction enzymes, preferably wherein the restriction enzyme recognizes a restriction site of 6 or 7 nucleotides, more preferably selected from the group consisting of BstZ17I and MluI. Preferably, the insert does not comprise a cleavage site of the first plurality of cleavage sites. Preferably, the vector backbone further comprises a polynucleotide encoding a functional selection marker, wherein the polynucleotide encoding a functional selection marker is preferably selected from SEQ ID NOs: 14-18, 79, and 110-116, or from a polynucleotide encoding a selection marker selected from SEQ ID NOs: 69, 70, and 81-88. Preferably, the fragments have a length of at most 900, 800, 700, 650, 600, 550, 500, 450, 400, 350, 300, 250, 200, 150, or 100 bp or less, preferably of at most 550 bp, such as about 500 bp. In preferred embodiments is provided the method wherein the vector backbone comprises a multiple cloning site that does not comprise a cleavage site of the first plurality of cleavage sites.

In a second aspect is provided a polynucleotide vector backbone as defined in the first aspect. Preferably, the vector backbone has at least 70% sequence identity with any one of SEQ ID NOs: 68 and 80. In preferred embodiments is provided a recombinant polynucleotide vector comprising a polynucleotide insert and a polynucleotide vector backbone as defined above.

In a third aspect is provided a method for amplifying a polynucleotide of interest, the method comprising the steps of: i) providing a recombinant polynucleotide vector comprising the polynucleotide of interest as an insert, and a vector backbone according to the second aspect; ii) amplifying the recombinant polynucleotide vector of step i) by transforming a suitable microorganism with it, and culturing said transformed microorganism in a culture medium under conditions suitable for vector amplification to obtain amplified recombinant polynucleotide vector; iii) isolating the amplified recombinant polynucleotide vector from the culture medium of step ii) to obtain isolated amplified recombinant polynucleotide vector; iv) contacting the isolated amplified recombinant polynucleotide vector with cleavage means capable of cleaving the first plurality of cleavage sites to produce backbone fragments; and optionally, v) separating the nucleotide sequence of interest from the backbone fragments of step iv).

In a fourth aspect the invention provides a kit of parts comprising: i) a polynucleotide vector backbone according to the second aspect, and at least one of iia) materials for use in a separation technique as defined in the first aspect, such as spin filters; or iib) cleavage means as defined in the first aspect.

In a fifth aspect the invention provides the use of a polynucleotide vector backbone according to the second aspect for the purification of a polynucleotide insert. In preferred embodiments this use is in a method for enhancing transcription of a nucleotide sequence of interest in a eukaryotic cell, the method comprising the steps of: i) providing a recombinant polynucleotide vector comprising the polynucleotide of interest as an insert, and a vector backbone according to the second aspect; ii) amplifying the recombinant polynucleotide vector of step i) by transfecting it to a suitable microorganism and culturing said microorganism in a culture medium under conditions suitable for vector amplification to obtain amplified recombinant polynucleotide vector; iii)isolating the amplified recombinant polynucleotide vector from the culture medium of step ii) to obtain isolated amplified recombinant polynucleotide vector; iv) contacting the isolated amplified recombinant polynucleotide vector with cleavage means capable of cleaving the first plurality of cleavage sites to produce backbone fragments; v) separating the nucleotide sequence of interest from the backbone fragments of step iv) to obtain an isolated nucleotide sequence of interest; vi) integrating the isolated nucleotide sequence of interest in the genome of a eukaryotic cell, preferably a mammalian cell or an insect cell, to obtain a transgenic cell; vii) culturing the transgenic cell under conditions conducive to expression of the nucleotide sequence of interest.

DESCRIPTION OF EMBODIMENTS

Self-Immolative Polynucleotide Vector Backbone

The invention relates to a backbone that can be used in a vector, which is primed to allow the backbone to be shredded by the use of cleavage means such as restriction enzymes, while leaving the insert (which generally comprises a region of interest) intact. The backbone is divided into small fragments by cleavage sites, which are not present in the insert, and thus the vector backbone is primed for degradation. After cleavage the insert remains as the sole polynucleotide fragment of considerable length, enabling easy separation between the desired fragment and the undesired debris that remains of the vector backbone. The invention is easily implemented without the requirement of additional hardware, and can be practiced in any lab equipped for molecular cloning. The self-immolative backbone can be used in methods for the production of polynucleotide fragments. Such methods can also be used for efficient preparation of specific homology-directed repair (HDR) template DNA in CRISPR/Cas mediated DNA-editing, or for preparation of RNA for use in synthetic biology. Such methods can also be used to prepare (circular) RNA for use in e.g. synthetic biology. The method is easier and faster than existing methods and leads to improved insert yields.

In a first aspect the invention provides a polynucleotide vector backbone, wherein the vector backbone comprises a first plurality of cleavage sites that divide the vector backbone into fragments having a length of at most 1000 bp. Such a polynucleotide vector backbone is referred to herein as a backbone according to the invention. An insert that is intended to be used with the backbone is similarly referred to as an insert for use in the invention; a vector comprising a backbone according to the invention is referred to as a vector according to the invention. Because the backbone can disassemble into fragments, it is reminiscent of synthetic self-immolative polymers that disassemble into monomers when a trigger is provided. While the backbone does not disassemble into monomers, it does disassemble into fragments that are sufficiently small to be easily disposed of. For ease of reference, sequences of polynucleotide that together constitute a single fragment (that is: a discrete molecule) after degradation are also referred to as a fragment when the intact backbone is discussed (that is: when the fragments are still joined in the backbone). It will be apparent from context whether a fragment refers to a discrete polynucleotide molecule that is a degradation product of a backbone according to the invention, or whether it refers to a polynucleotide sequence in between two cleavage sites in the intact backbone. FIG. 1 illustrates this aspect.

A vector, sometimes referred to as a plasmid, is herein understood to mean a man-made, or recombinant, nucleic acid molecule resulting from the use of recombinant polynucleotide technology, and which for example can be used to deliver exogenous DNA into a host cell. As used herein, "vector" and "recombinant vector" are used interchangeably as non-recombinant vectors are not part of the invention.

Vectors are preferably circular, and usually comprise further genetic elements to facilitate their use in molecular cloning, such as for example selectable markers, multiple cloning sites, et cetera. A vector is said to be recombinant when it comprises sequences that originally derive from different sources, such as from different organisms. The vector is a polynucleotide, which means that it can be DNA or RNA. Because it is more convenient to use in practice, in preferred embodiments the polynucleotide is DNA.

A vector is generally used to either amplify a specific sequence of interest, or to isolate, identify, and express a sequence of interest, or to express one. The vector is then designed around this sequence of interest, with said sequence being referred to as an insert, and with the remainder of the vector being referred to as the backbone of the vector. Often the insert in a plasmid represents exogenous DNA while the backbone of the plasmid facilitates its use and multiplication. This is known to a skilled person. In general, a vector consists of a backbone (which is responsible for functionality in that it harbours features such as a selection marker or a multiple cloning site or an origin of replication) and an insert, which is the polynucleotide that comprises the sequence of interest. It can for example encode a gene of interest. However, some vectors do not comprise an insert. For example, for production of the backbone it is convenient to amplify a plasmid consisting only of the backbone. This is often referred to as an empty vector. Through standard cloning techniques an insert can be incorporated, for example in the multiple cloning site. Because of this close interrelation, any reference to a vector can also be read as a reference to the backbone of that vector, and conversely any reference to a backbone can be read as a reference to a vector, particularly to an empty vector, such as shown in FIG. 2.

Many vectors and their accompanying backbones are known in the art, and are commercially available. A vector may for example be part of a recombinant viral vector for expression of a protein in a plant or plant cell (e.g. a vector derived from cauliflower mosaic virus, CaMV, or tobacco mosaic virus, TMV) or in a mammalian organism or mammalian cell system (e.g. a vector derived from Moloney murine leukemia virus (MMLV), a Retrovirus, a Lentivirus, an Adeno-associated virus (AAV) or an adenovirus (AdV)). Accordingly a preferred backbone is a viral backbone, such as a CaMV, TMV, MMLV, retroviral, lentiviral, AAV, or AdV backbone. In preferred embodiments of this aspect, the backbone according to the invention is comprised in a recombinant polynucleotide vector; accordingly, in preferred embodiments the invention provides a recombinant polynucleotide vector comprising a polynucleotide insert and a backbone according to the invention. More preferred embodiments consist of such a backbone and such an insert. It is to be understood that when a vector is said to consist of a given set of elements, this does not imply that some short linker sequences or individual base pairs, for example vestiges from a cloning process, cannot be present at all; rather it is to be understood that a vector consisting of specific elements does not comprise any substantial further elements.

Examples of suitable backbones according to the invention are shown in the examples and provided in SEQ ID NOs: 68 and 80. Examples of suitable backbones that can be modified by introduction of cleavage sites, thus forming backbones according to the invention, are provided in SEQ ID NOs: 1-6. A skilled person knows that silent mutations can be made in such backbones, leading to identical or substantially identical functionality; and that rearrangement of functional units within the backbone can be made, or that individual units can be inverted, or that one functional unit such as a marker can be replaced by a different functional unit of the same type such as a different marker, or combinations of any of these changes. Therefore, in preferred embodiments is provided a polynucleotide vector backbone according to the invention, wherein the vector backbone has at least 70%, 75%, 80%, 85%, 90%, 91%, 92%, 93%, 94%, 95%, 96%, 97%, 98%, 99%, or 100% sequence identity with any one of SEQ ID NOs: 1-6, 68, and 80, preferably 68 and 80; preferably having at least 90%, 91%, 92%, 93%, 94%, 95%, 96%, 97%, 98%, 99%, or 100% sequence identity with any one of SEQ ID NOs: 1-6, 68, and 80, preferably 68 and 80; more preferably having at least 95%, 96%, 97%, 98%, 99%, or 100% sequence identity with any one of SEQ ID NOs: 1-6, 68, and 80, preferably 68 and 80; most preferably having at least 98%, 99%, or 100% sequence identity with any one of SEQ ID NOs: 1-6, 68, and 80, preferably 68 and 80.

To prevent its degradation, it is preferred that the insert in such a vector not have a cleavage site that is involved in the immolation of the backbone, accordingly, in preferred embodiments is provided a recombinant polynucleotide vector comprising a polynucleotide insert and a backbone according to the invention, wherein the insert does not comprise a cleavage site of the first plurality of cleavage sites; more preferably the insert does not comprise a species of cleavage site of the first plurality of cleavage sites.

Cleavage Sites, Cleavage Means, and Fragments

To enable its use, the backbone according to the invention has a first plurality of cleavage sites. A cleavage site is a well-defined region of the backbone that can be cleaved by controlled means. A very common example of a cleavage site is a restriction site. Many such cleavage sites are known in the art. A cleavage site is often a particular short sequence, and can be cleaved, for example hydrolyzed, by a cleavage means. For example, a restriction site of six nucleotides in length can be recognized for example by its recognition sequence, and then cleaved by a restriction enzyme. As is known in the art, this cleavage can be inside the recognition site, or at one of its extremes, or even one or two or more nucleotides away from the site. As is known, a cleavage site can in some cases be non-contiguous, as for example is the case for restriction enzyme AccB7I, which recognizes CCA directly followed by any five nucleotides, directly followed by TGG; such a cleavage site has a restriction recognition site of six defined nucleotides, yet it is a cleavage site of 11 nucleotides in length. The cleavage means recognizes the cleavage site (most preferably because of a recognition sequence) and for example causes a double-stranded chain break, cutting the polynucleotide at the cleavage site. Of course, a cleavage site can be such that the actual chain break is at an area outside the actual recognition sequence, but it is common to still refer to cleavage induced by such a site as "cleavage of that site". Each cleavage site has its associated cleavage means. A cleavage site preferably has a length of at least 3, 4, 5, or 6 nucleotides, more preferably at least 4, most preferably at least 5 nucleotides. A cleavage site preferably has a recognition sequence that has a length of at least 3, 4, 5, or 6 nucleotides, more preferably at least 4, even more preferably at least 5, most preferably at least 6 nucleotides. A cleavage site or a recognition sequence preferably has a length of at most 20 nucleotides, more preferably at most 15, even more preferably at most 10, still more preferably at most 9, still more preferably at most 8 nucleotides.

Types of cleavage site, such as restriction sites, can have multiple species, such as restriction sites that are recognized by different restriction enzymes. Another example is that the type of cleavage site that is RNA-guided DNA endonuclease recognition sites, has multiple species of cleavage site, such as cleavage sites that are recognized by RNA-guided DNA endonuclease enzymes comprising different guide RNAs.

In preferred embodiments, the cleavage means are selected from the group consisting of restriction enzymes, RNA-guided DNA endonuclease enzymes, sequence-specific nucleases, sequence-specific ultrasonication, sequence-specific oxidative small molecules such as bleomycin, and sequence-specific hydrolyzing small molecules such as lanthanide complexes. More preferred cleavage means are selected from the group consisting of restriction enzymes, RNA-guided DNA endonuclease enzymes, and sequence-specific nucleases. Restriction enzymes are most preferred. Accordingly, in preferred embodiments is provided a backbone according to the invention, wherein the cleavage sites from the first plurality of cleavage sites are restriction endonuclease recognition sites.

Restriction enzymes are broadly known in the art and are widely commercially available (see e.g. Loenen et al., Nucleic Acids Res. 2014 42(1): 3-19 DOI: 10.1093/nar/gkt990). They are also known as restriction endonucleases. A restriction enzyme or restriction endonuclease is an enzyme that cleaves polynucleotides such as DNA into fragments at or near a specific recognition site. A restriction site, or restriction recognition site, or a restriction endonuclease recognition site, is a location on a DNA molecule containing a specific sequence of nucleotides, typically 4-8 base pairs in length and often palindromic, that is recognized by a restriction enzyme. Preferred restriction sites are non-contiguous restriction sites because they allow non-defined nucleotide positions; in preferred embodiments, the first plurality of cleavage sites comprises at least one non-contiguous restriction site. Examples of restriction enzymes are AanI, AarI, AasI, AatI, AatII, AbsI, AccI, AccIII, Acc16I, Acc36I, Acc65I, Acc113I, AccB1I, AccB7I, AccBSI, AciI, AclI, AclWI, AcoI, AcsI, AcuI, AcvI, AcyI, AdeI, AfaI, AfeI, AfiI, AflIII, AgeI, AhdI, AhlI, AjiI, AjnI, AjuI, AleI, AlfI, AloI, AluI, AluBI, AlwI, Alw21I, Alw26I, Alw44I, AlwNI, Ama87I, Aor13HI, Aor51HI, ApaI, ApaLI, ApeKI, ApoI, AscI, AseI, AsiGI, AsiSI, Asp700I, Asp718I, AspA2I, AspEI, AspLEI, AspS9I, AsuII, AsuC2I, AsuHPI, AsuNHI, AvaI, AvaII, AviII, AvrII, AxyI, BaeI, BaeGI, BalI, BamHI, BanI, BanII, BanIII, BarI, BauI, BbeI, BbrPI, BbsI, BbuI, BbvI, Bbv12I, BbvCI, BccI, BceAI, BcgI, BciVI, BciT130I, BclI, BcnI, BcoDI, BcuI, BdaI, BfaI, BfiI, BfmI, BfoI, BfuI, BfuAI, BfuCI, BglI, BglII, BisI, BlnI, BlpI, BlsI, BmcAI, Bme18I, Bme1390I, Bme15801, BmeRI, BmeT110I, BmgBI, BmgT120I, BmiI, BmrI, BmrFI, BmsI, BmtI, BmuI, BoxI, BpiI, BplI, BpmI, Bpu10I, Bpu14I, Bpu1102I, BpuAI, BpuEI, BpuMI, BpvUI, BsaI, Bsa29I, BsaAI, BsaBI, BsaHI, BsaJI, BsaMI, BsaWI, BsaXI, Bsc4I, Bse1I, Bse3DI, Bse8I, Bse21I, Bse118I, BseAI, BseBI, BseCI, BseDI, BseGI, BseJI, BseLI, BseMI, BseMII, BseNI, BsePI, BseRI, BseBI, BseXI, BseX3I, BseYI, BsgI, BshVI, Bsh1285I, BshFI, BshNI, BshTI, BsiEI, BsiHKAI, BsiHKCI, BsiSI, BsiWI, BsiYI, BslI, BslFI, BsmI, BsmAI, BsmBI, BsmFI, BsnI, Bso31I, BseBI, Bsp13I, Bsp19I, Bsp68I, Bsp119I, Bsp120I, Bsp143I, Bsp1286I, Bsp1407I, Bsp1720I, BspACI, BspCNI, BspDI, BspEI, BspHI, BspLI, BspLU11I, BspMI, BspO1, BspPI, BspQI, BspTI, BspT104I, BspT107I, BspTNI, BspXI, BsrI, BsrBI, BsrDI, BsrFI, BsrGI, BsrSI, BssAI, BssECI, BssHII, BssKI, BssMI, BssNI, BssNAI, BssSαI, BssT1I, Bst2BI, Bst2UI, Bst4CI, Bst6I, Bst1107I, BstACI, BstAPI, BstAUI, BstBI, BstBAI, BstC8I, BstDEI, BstDSI, BstEII, BstENI, BstF5I, BstH2I, BstHHI, BstHPI, BstKTI, BstMAI, BstMBI, BstMCI, BstMWI, BstNI, BstNSI, BstOI, BstPI, BstPAI, BstSCI, BstSFI, BstSLI, BstSNI, BstV1I, BstV2I, BstXI, BstX2I, BstYI, BstZI, BstZ17I, Bsu15I, Bsu36I, BsuRI, BsuTUI, BtgI, BtgZI, BtrI, BtsCI, BtslMutI, BtsαI, BtuMI, BveI, Cac8I, CaiI, CciI, CciNI, CelII, CfoI, CfrI, Cfr9I, Cfr10I, Cfr13I, Cfr42I, ClaI, CpoI, CsiI, CspI, Csp6I, Csp45I, CspAI, CspCI, CviJI, CviKI-1, CviQI, DdeI, DinI, DpnI, DpnII, DraI, DraII, DraIII, DrdI, DriI, DseDI, EaeI, EagI, Eam1104I, Eam1105I, EarI, EciI, Ecl136II, EclXI, Eco24I, Eco31I, Eco32I, Eco47I, Eco47III, Eco52I, Eco53kI, Eco57I, Eco57MI, Eco72I, Eco81I, Eco88I, Eco91I, Eco105I, Eco130I, Eco147I, EcolCRI, EcoNI, EcoO65I, EcoO109I, EcoP15I, EcoRI, EcoRII, EcoRV, EcoT14I, EcoT22I, EcoT38I, EgeI, EheI, ErhI, Esp3I, FalI, FaqI, FauI, FauNDI, FbaI, FblI, Fnu4H1, FokI, FriOI, FseI, Fsp4HI, FspI, FspAI, FspBI, GlaI, GluI, GsaI, GsuI, HaeII, HaeIII, HapII, HhaI, HinII, Hin4I, Hin6I, HincII, HindII, HindIII, HinfI, HinP1I, HpaI, HpaII, HphI, Hpy8I, Hpy99I, Hpy166II, Hpy188I, Hpy188III, HpyAV, HpyCH4III, HpyCH4IV, HpyCH4V, HpyF3I, HpyF10VI, Hsp92I, HspAI, I-CeuI, I-PpoI, I-SceI, ItaI, KasI, KflI, KpnI, Kpn2I, KspI, Ksp22I, Ksp632I, KspAI, Kzo9I, LguI, Lsp1109I, LweI, MabI, MaeI, MaeII, MalI, MamI, MauBI, MbiI, MboI, MboII, MfeI, MflI, MhlI, MlsI, MluI, MluCI, MluNI, MlyI, Mly113I, MmeI, MnlI, Mph1103I, MreI, MroI, MroNI, MroXI, MscI, MslI, MspI, Msp20I, MspA1I, MspR9I, MssI, MunI, MvaI, Mva1269I, MwoI, NaeI, NarI, NciI, NcoI, NdeI, NdeII, NgoMIV, NheI, NlaIV, NmeAIII, NotI, NruI, NsbI, NsiI, NspI, NspV, OliI, PacI, PaeI, PaeR7I, PagI, PalAI, PasI, PauI, PceI, PciI, PciSI, PctI, PdiI, PdmI, PfeI, Pfl23II, PflMI, PfoI, Phot, PI-PspI, PI-SceI, PinAI, PleI, Ple19I, PluTI, PmaCI, PmeI, PmlI, PpiI, PpsI, Ppu21I, PpuMI, PscI, PshAI, PshBI, PsiI, Psp5II, Psp6I, Psp124BI, Psp1406I, PspCI, PspEI, PspFI, PspGI, PspLI, PspN4I, PspOMI, PspPI, PspPPI, PspXI, PsrI, PstI, PsuI, PsyI, PteI, PvuI, PvuII, RcaI, RgaI, RigI, RruI, RsaI, RsaNI, RseI, RsrII, Rsr2I, SacI, SadI, SaiI, SanDI, SapI, SatI, Sau3AI, Sau96I, SbfI, ScaI, SchI, ScrFI, SdaI, SduI, SetI, SexAI, SfaAI, SfaNI, SfcI, SfiI, SfoI, Sfr274I, Sfr303I, SfuI, SgfI, SgrAI, SgrBI, SgrDI, SgsI, SinI, SiaI, SmaI, SmiI, SmiMI, SmoI, SmuI, SnaBI, SpeI, SphI, SilI, Sse9I, Sse8387I, SseBI, SsiI, SspI, SspBI, SspDI, SstI, SstII, StuI, StyI, StyD4I, SwaI, TaaI, TaiI, TaqI, TagiI, TaqaI, TasI, TatI, TauI, TfiI, TliI, TscAI, TseI, TsoI, Tsp509I, TspDTI, TspEI, TspGWI, TspMI, TspRI, TstI, Van91I, VneI, VpaK11BI, VspI, XagI, XapI, XbaI, XceI, XcmI, XhoI, XhoII, XmaI, XmaCI, XmaJI, XmiI, XmnI, XspI, ZraI, ZrmI, Zsp2I, and their isoschizomers or neoschizomers. Preferred restriction enzymes are endonucleases that recognise a DNA sequence, more preferably a DNA sequence of at least 6 nucleotides, even more preferably at least 6 or 7 nucleotides. Preferred restriction enzymes recognize a site of at most 7 nucleotides, more preferably of at most 6 nucleotides. Preferred restriction enzymes are not sensitive to methylation. Preferred restriction enzymes do not show star activity, more preferably do not show star activity under conditions used for the method according to the invention, even more preferably do not show star activity when no organic solvent is present, the ionic strength of the reaction buffer is at least 100 mM, and the pH of the reaction buffer is at most 7.6, most preferably do not show star activity at all. Restriction enzymes that do not see frequent use in routine cloning are very convenient because they would not interfere with common cloning processes involving a backbone according to the invention. Accordingly highly preferred restriction enzymes recognize at least 6 or 7, preferably 6 nucleotides and are not AgeI, BamHI, BssHII, DraI, EagI, EcoRI, EcoRV, HindIII, NcoI, PstI, PvuI, SalI, XbaI, XhoI, or XmaI, more preferably not AgeI, BamHI, BbsI, BfuAI, BglII, BsaI, BsmBI, BssHII, DraI, EagI, EcoRI, EcoRV, HindIII, NcoI, PstI, PvuI, SalI, XbaI, XhoI, or XmaI. Most preferred restriction enzymes for degrading the backbone according to the invention are BstZ17I and MluI.

A cleavage means can also be an RNA-guided DNA endonuclease enzyme, as used in the CRISPR/Cas technology and referred to hereinafter as a Cas endonuclease. A preferred Cas endonuclease is a Cas9 endonuclease. This technology is generally known, see for example Khan et al., Journal of Biomedical Science, 2018, 25:29, DOI: 10.1186/s12929-018-0425-5. A Cas endonuclease is guided by an RNA having any sequence of choice, and will cleave any cleavage site that its guide RNA points it to. This makes Cas endonucleases very versatile for cleaving a backbone according to the invention. Other Cas and Cas-like proteins can be used as well as different protospace adjacent motifs (PAMs).

Any other sequence-specific nuclease can be used to cleave its associated sequence. Zinc finger nucleases and TALEN belong to this group. An advantage of using restriction enzymes is their high fidelity of sequence specificity. Restriction enzymes have known, predictable and reliable specificity and fidelity.

Other suitable cleavage means are sequence-specific ultrasonication (see Grokhovsky et al., Biophys J. 2011; 100(1): 117-125; DOI: 10.1016/j.bpj.2010.10.052), a sequence-specific oxidative small molecule such as bleomycin or a modified porphyrin (see for example Van Dongen et al., Nature Chem. 5, p. 945-951 (2013) DOI: 10.1038/nchem.1752), and a sequence-specific hydrolyzing small molecule such as a lanthanide complex (see for example Hall et al., Nucleic Acids Res. 1996; 24(18): 3522-3526. PMID: 8836177). More preferred cleavage means are selected from the group consisting of a restriction enzyme, an RNA-guided DNA endonuclease enzyme, and a sequence-specific nuclease. A restriction enzyme is most preferred, for example because of its ready availability and convenient usability.

As mentioned above, a cleavage site is cleaved by its associated cleavage means. In the context of this document, cleavage is meant to refer to a break in the polynucleotide, which generally means a double-stranded break, as vectors and backbones are preferably double-stranded. In the context of this invention, cleavage refers to the controlled cleavage of a cleavage site, as effected by the associated cleavage means. The cleavage can be a direct double cleavage, leading to blunt ends, or it can be a set of two nicks in opposing strands, the nicks not being separated by more than about 15, preferably 10 nucleotides, leading to sticky ends. As long as adjoining fragments are no longer substantially associated with one another, the cleavage can be considered suitable for use in this invention. In preferred embodiments, cleavage is promoted by an increase in medium temperature or ionic strength, preferably medium temperature. Optionally, in these embodiments, additional agents may be added to increase dissociation of the cleaved fragments. Such agents are known in the art; examples are DMSO and formamide.

The first plurality of cleavage sites is configured to convert the backbone according to the invention to fragments. It is convenient when the cleavage sites in the first plurality can be cleaved in one single reaction step, possibly involving multiple different types or species cleavage means if the plurality comprises different types or species of cleavage sites. For example when the cleavage sites are restriction sites, the degradation can be performed by a mixture of restriction enzymes that can cleave their respective cleavage sites under the same reaction conditions. A mixture of cleavage means is not limited as to how many different cleavage means are comprised, as the invention relates to the degradation of the backbone and not in the details of how this is achieved precisely.

Nonetheless, for convenience it is preferred when the cleavage sites in the first plurality are not very diverse, and are generally of the same type. In preferred embodiments, the cleavage sites in the first plurality can all be cleaved under the same reaction conditions. For this reason, in preferred embodiments, all cleavage sites in the first plurality are restriction sites. In other preferred embodiments, all cleavage sites in the first plurality are recognition sites for an RNA-guided DNA endonuclease enzyme. In other preferred embodiments, all cleavage sites in the first plurality are recognition sites for a sequence-specific nuclease.

When the cleavage sites in the first plurality are all of the same type, it is preferred that the associated cleavage means is similarly of low diversity, and therefore substantially of the same species. For example, for ease of preparation, a mixture of cleavage means preferably comprises at most 5, 4, 3, 2, or 1 species of cleavage means, such as different restriction enzymes or RNA-guided DNA endonucleases with different guide RNAs. Accordingly, in preferred embodiments is provided the backbone according to the invention, wherein the cleavage sites comprise at most 5, 4, 3, 2, or 1 different cleavage sites, preferably at most 3, 2, or 1 different cleavage sites, more preferably at most 2 or 1 different cleavage sites, most preferably only 1 species of cleavage site.

In preferred embodiments, the first plurality of cleavage sites comprises only restriction sites, and comprises no more than 6, 5, 4, 3, 2, or 1, preferably no more than 3, 2, or 1, more preferably no more than 2 or 1, most preferably comprises only 1, species of restriction site, wherein the restriction sites are preferably selected from the group consisting of restriction sites for restriction enzymes as described above, more preferably selected from the group consisting of restriction sites for BssHI, BstZ17I, and MluI, most preferably selected from restriction sites for BstZ17I and MluI.

In preferred embodiments, the first plurality of cleavage sites comprises only recognition sites for an RNA-guided DNA endonuclease enzyme, and comprises no more than 5, 4, 3, 2, or 1, preferably no more than 3, 2, or 1, more preferably no more than 2 or 1, most preferably comprises only 1, species of recognition site.

Degradation of the Backbone

As explained earlier herein, the invention revolves around a backbone that can be degraded into smaller fragments, to allow easy isolation of an insert. The vector backbone is divided into fragments by the cleavage sites from the first plurality. As demonstrated in the examples, the efficiency of size-based separation of polynucleotide fragments depends on the method that is used for this separation. When the size difference between an insert and the fragments is larger, the separation will be easier and/or more complete. When the size difference is smaller, separation can still be performed, but might lose efficiency, for example leading to incomplete separation.

The fragments can have any length and any distribution of lengths. For practical purposes, it is preferred to divide the backbone into fragments having a length of at most 1000 bp, to allow easier separation from relatively small inserts. In preferred embodiments is provided the backbone according to the invention, wherein the fragments have a length of at most 900, 800, 700, 650, 600, 550, 500, 450, 400, 350, 300, 250, 200, 150, or 100 bp or less, preferably of at most 700, 650, 600, 550, 500, 450, 400, 350, 300, 250, 200, 150, or 100 bp or less, more preferably of at most 550 bp, such as of about 500 bp or less. Variation in length by single nucleotides or by ten or fewer nucleotides is not expected to have a substantial effect on the behavior of a fragment, so fragment size is preferably seen as a target size and not as an absolute barrier. The length of a fragment is preferably defined as the length of the resulting fragment after cleavage has been performed. For practival purposes, it is preferred to divide the backbone into fragments having a length of at least 20, 30, 40, 50, 60, 70, 80, 90, 100, 110, 120, 130, 140, 150, 160, 170, 180, 190, 200, 210, 220, 230, 240, or 250 bp, more preferably at least about 100 bp, even more preferably at least about 150 bp, most preferably at least about 200 bp.

In other preferred embodiments, the fragments have a length of at most 40%, 35%, 30%, 25%, 20%, 15%, 10%, or 5% of the length of the insert. Fora backbone without an insert, or for an empty vector according to the invention, this can mean that the fragments have a length relative to an intended insert. Length in this context relates to the number of nucleotides.

For ease of use, it is preferable to have fragments that are substantially of the same size. This allows the use of more specialized separation techniques. Accordingly, in preferred embodiments, the fragments have a length distribution wherein the shortest fragment has at least 20%, 25%, 30%, 35%, 40%, 45%, 50%, 55%, 60%, 65%, 70%, 75%, 80%, 85%, 90%, 95%, or 98% of the length of the longest fragment. Of course the insert is not to be considered a fragment, despite its release during fragmentation. In other preferred embodiments, the length difference between the shortest and the longest fragment is no more than 400, 350, 300, 250, 200, 150, 100, 50, or 20 bp, preferably no more than 250 bp.

The application of cleavage means to cleave the first plurality of cleavage sites, leading to fragments, is referred to herein as degradation, immolation, shredding, or cleavage, as will be apparent from context. A polynucleotide sequence that is divided into fragments is referred to herein as a self-immolative sequence, or a degradation-ready sequence, or a sequence primed for degradation.

Possible Functional Elements of the Backbone or of the Insert

The backbone according to the invention and an insert for use in the invention can comprise different polynucleotide elements that each serve a particular function; these are referred to as functional elements. Examples of functional elements are markers, multiple cloning sites, expression enhancing elements, origins of replication, and promoters. Backbone design and vector design are an established field of art, and a skilled person will know how to design a backbone or insert for a particular application.

Marker

In preferred embodiments a backbone according to the invention or an insert for use in the invention comprises a polynucleotide encoding a functional marker, preferably a selection marker, wherein the polynucleotide encoding a functional marker is preferably selected from SEQ ID NOs: 14-18, 79, and 110-116, or from a polynucleotide encoding a marker selected from SEQ ID NOs: 69, 70, 81-88; the polynucleotide encoding the functional marker is preferably in the backbone. The marker is preferably derived from SEQ ID NOs: 7-13.

Selection markers are known in the art. A selection marker, also known as a selectable marker, is a gene that when introduced into a cell, especially a bacterium or to cells in culture, confers a trait suitable for artificial selection. Examples of selection markers are resistance markers that confer resistance to for example antibiotics, and biosynthesis markers that complement auxotrophy, or are used for screening, such as LacZalpha. Preferred selection markers are resistance markers, more preferably antibiotic resistance markers. Suitable antibiotic resistance markers are resistance genes against kanamycin, spectinomycin, streptomycin, ampicillin, carbenicillin, bleomycin, erythromycin, polymyxin B, tetracycline, chloramphenicol, and zeocin. In preferred embodiments, the selection marker provides resistance against an antibiotic selected from the group consisting of zeocin (zeo), chloramphenicol (cam), tetracyclin (tet), streptomycin (str), kanamycin (kan), and ampicillin (amp). In more preferred embodiments, this antibiotic is selected from kanamycin (kan) and ampicillin (amp).

The polynucleotide encoding a functional marker is preferably any one of SEQ ID NOs: 14-18, 79, and 110-116. Such a sequence preferably has 70, 75, 80, 85, 90, 91, 92, 93, 94, 95, 96, 97, 98, 99, or 100% sequence identity with the selected SEQ ID NO, more preferably it has 90, 91, 92, 93, 94, 95, 96, 97, 98, 99, or 100% sequence identity, even more preferably it has 95, 96, 97, 98, 99, or 100% sequence identity, most preferably it has 98, 99, or 100% sequence identity, such as 99% or 100% sequence identity. In more preferred embodiments, the polynucleotide encoding a functional marker is selected from any one of SEQ ID NOs: 14-15. A preferred marker is a marker that comprises at least one cleavage site from the first plurality of cleavage sites.

Alternately, the nucleotide encoding a functional marker encodes a functional marker that is preferably derived from any one of Kan, Amp, Zeo, LacZalpha, and chloramphenicol, more preferably from Kan or Amp. The functional marker is preferably derived from any one of SEQ ID NOs: 7-13. It preferably encodes a polypeptide that has 70, 75, 80, 85, 90, 91, 92, 93, 94, 95, 96, 97, 98, 99, or 100% sequence identity with the selected SEQ ID NO, more preferably it has 90, 91, 92, 93, 94, 95, 96, 97, 98, 99, or 100% sequence identity, even more preferably it has 95, 96, 97, 98, 99, or 100% sequence identity, most preferably it has 98, 99, or 100% sequence identity, such as 99% or 100% sequence identity. In more preferred embodiments, a functional marker is derived from any one of SEQ ID NOs: 7-10 or 13, even more preferably from any one of SEQ ID NOs: 7-8. In this context, a marker derived from an amino acid sequence is preferably a polynucleotide encoding that amino acid sequence.

In another aspect the invention provides a polynucleotide encoding a functional marker as defined above, preferably comprising at least 1, 2, 3, or 4 cleavage sites; for polynucleotides wherein not all mutations relative to the wild-type are silent mutations, the encoded polypeptide is also encompassed by the invention.

A marker has no direct utility when it is not functional. Mutation to established markers may decrease their functionality. However, decreased functionality does not equate lack of functionality. For example, decreased functionality may result in more stringent selection when for example an antibiotic resistance marker is less efficient in its function, effectively conferring less resistance. Such an effect is not necessarily detrimental to the backbone—in fact, it is known that less efficient resistance markers can lead to increased copy number of the plasmid, as more selection marker activity is required to allow cell survival. On the other hand, when a self-immolative resistance marker has an activity that is closer to that of the wild type, its will be easier to use that resistance marker in existing protocols because its behavior will be more predictable. Accordingly, the level of functionality of a selection marker is dependent on the intended use of the backbone. In preferred embodiments, the activity of a self-immolative resistance marker is at least 30, 40, 50, 60, 70, 80, 90, 95, 99, or 100% of that of wild type resistance marker, more preferably at least 70%, even more preferably at least 90%.

Vectors with a marker, or elements for activity selection of a specific sequence, can be easily selected after transfection of the vector. Vectors without a marker can have increase utility in gene therapy, for example as described in WO9605297.

Multiple Cloning Site

A multiple cloning site (MCS) is a sequence in a backbone harbouring a number of recognition sites for restriction enzymes to facilitate cloning of fragments in that vector. This sequence is commonly small (<100 bp) and the recognition site sequences are generally uniquely present in the multiple cloning site, and not found in the rest of the backbone or the fragment of interest to be cloned (the insert). Multiple coning sites are commonly known in the art. Preferred MCS have a length of at most 300, 250, 200, 190, 180, 170, 160, 150, 140, 130, 120, 110, 100, 90, 80, 70, or fewer bp. Preferred MCS comprise about 4-30, 6-25, 8-20, 10-15 restriction sites.

In preferred embodiments is provided the vector backbone according to the invention, wherein the vector backbone comprises a polynucleotide encoding a multiple cloning site. An MCS can also be in an insert for use in the invention; this can be advantageous when amplification of the polynucleotide encoding the MCS is required. Preferably, a multiple cloning site does not comprise a cleavage site of the first plurality of cleavage sites, and/or comprises at least one restriction site that is not in the first plurality of cleavage sites. This allows use of the MCS without triggering immolation of the backbone. A preferred MCS comprises a BssHII restriction site. BssHII is compatible with MluI which is a preferred cleavage means for triggering immolation. Conversely, a cleavage site present in an MCS can be used to help divide the backbone into smaller fragments, when a restriction enzyme recognizing that cleavage site is used as additional cleavage means for immolation. Preferably, the MCS comprises restriction sites for restriction enzymes that can be used under the same reaction conditions as the cleavage means. This allows exact liberation of the insert simultaneous with immolation, which improves control over the insert that can be obtained after immolation.

In preferred embodiments, the backbone according to the invention comprises a polynucleotide encoding an MCS that shares at least 80%, more preferably at least 90%, most preferably at least 98% or 100% sequence identity with SEQ ID NO: 19. More preferably, the backbone according to the invention comprises a polynucleotide encoding an MCS that comprises the same restriction sites as SEQ ID NO: 19. In preferred embodiments, the backbone according to the invention comprises a polynucleotide encoding an MCS with recognition sites for restriction enzymes as described above, preferably for restriction enzymes that recognise six or seven nucleotides. It is preferred when recognition sites are for enzymes that result in the same overhang as any restriction enzymes in the first plurality of cleavage means. An example is BssHII, MauBI and AscI when MluI is in the first plurality.

A backbone can have an MCS when it is to be used with any type of insert, in which case the MCS allows tailored selection of a restriction enzyme for insertion of an insert into the plasmid. A backbone that is designed for use with only a single insert, or with an insert that is always inserted using the same restriction enzyme, does not need an MCS.

Promoter

In preferred embodiments the backbone according to the invention or the insert for use in the invention comprises a promoter, preferably a promoter that is configured to be operably linked to a sequence of interest in the insert, or to a nucleotide sequence encoding a marker as defined earlier herein. Accordingly, the promoter can be configured to be operably linked to a sequence that is not present in the backbone itself, when no insert is present. Promoter refers to a nucleic acid sequence, located upstream or 5' to a translational start codon of an open reading frame (or protein-coding region) of a gene or to a nucleic acid sequence that functions to control the transcription of DNA, and that is involved in recognition and binding of RNA polymerase II and other proteins (trans-acting transcription factors) to initiate transcription. The term promoter refers to a nucleic acid fragment that functions to control the transcription of one or more nucleic acid sequences, located upstream with respect to the direction of transcription of the transcription initiation site of the sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one skilled in the art to act directly or indirectly to regulate the amount of transcription from the promoter. The promoter does not include the transcription start site (TSS) but rather ends at nucleotide −1 of the transcription site, and does not include nucleotide sequences that become untranslated regions in the transcribed mRNA such as the 5'-UTR. Promoters suitable for use in a backbone according to the invention may be tissue-specific, tissue-preferred, cell-type specific, inducible and constitutive promoters. Tissue-specific promoters are promoters which initiate transcription only in certain tissues or within certain cells of that tissue. Expression in a tissue-specific manner may be only in individual tissues or in combinations of tissues. Tissue-preferred promoters are promoters that preferentially initiate transcription in certain tissues. Cell-type-specific promoters are promoters that primarily drive expression in certain cell types. Inducible promoters are promoters that are capable of activating transcription of one or more DNA sequences in response to an inducer. The DNA sequences will not be transcribed when the inducer is absent or when an inhibitor is present, such as for the Tet-off promoter. Activation of an inducible promoter is established by application of the inducer or by absence of the inhibitor. Constitutive promoters are promoters that are active under many environmental conditions and in many different tissue types. Preferably, capability to initiate transcription is established in an expression system using an expression construct comprising said promoter operably linked to a nucleotide sequence of interest using a suitable assay such a RT-PCR or Northern blotting. A promoter is said to be capable to start transcription if a transcript can be detected or if an increase in a transcript level is found of at least 5%, 10%, 15%, 20%, 30%, 40%, 50%, 60%, 70%, 80%, 90%, 100%, 200%, 300%, 500%, 1000%, 1500%, 2000%, 4000%, 8000%, 16000%, or more as compared to transcription using a construct which only differs in that it is free of said promoter. In a further preferred embodiment, capability to initiate expression is established in an expression system using an expression construct comprising said promoter operably linked to a nucleotide sequence encoding a protein or polypeptide of interest. Preferably, said protein or polypeptide of interest is a secreted protein or polypeptide and expression of said protein or polypeptide of interest is detected by a suitable assay such as an ELISA assay, Western blotting or, dependent on the identity of the protein or polypeptide of interest, any suitable protein identification and/or quantification assay known to the person skilled in the art. Absent expression-suppressing factors, a promoter is said to be capable to initiate expression if the protein or polypeptide of interest can be detected or if an increase in an expression level is found of at least 5%, 10%, 15%, 20%, 30%, 40%, 50%, 60%, 70%, 80%, 90%, 100%, 200%, 300%, 500%, 1000%, 1500%, 2000%, 4000%, 6000%, or 10000% as compared to expression using a construct which only differs in that it is free of said promoter. A promoter is preferably configured to be operably linked to a polynucleotide sequence comprised in the insert.

Examples of promoters suitable for use in a backbone according to the invention are constitutive promoters or inducible promoters, preferably inducible promoters. In preferred embodiments the backbone according to the invention of the insert for use in the invention comprises a polynucleotide sequence encoding Lac promoters, trp, tac, Bla promoter, chloramphenicol resistance promoter (Pcat), phage promoters such as Lambda promoters P1, P5, P22 and Pr, P2, pPrpB, pTetO, and hybrid promoters such as lac-trp, Tac (lactose/IPTG inducible), alcB, T7, LacO, araBAD, pBAD (arabinose inducible, glucose repressible), pTrc, hybrid of trp and lac promoters (Lactose/IPTG inducible), *Bacillus subtilus* promoters, Pspac, SacB system promoters, P43, M13K07 genes 1-8 promoters, promoters active in mammalian cells such as CMV, SV40, EF1a, CAG (Eukaryotic promoter database (EPD), available at epd.vital-it.ch/index.php); other promoters such as UAS, PolII (H1/U6), MT, unc-54, Polyhedrin, SP6, TMV, plant promoters used in plants such as CaMV, 35S, Ubiquitin, Actin, Lat52, PR1a, PR2d, synthetic plant promoters (W. Liu and C. N. Steward, Current Opinion in Biotechnology 2016, 37:36-44), promoters active in yeast such as Gal4, AOX, PGK, ADH1, ADE2, TRP1.

Preferred promoters can be used to clone, identify and/or isolate fragments of interest. They include promoters involved in expression of markers as well as promoters involved of expression of gene sequence of the sequence of interest. Promoters include viral, archaeal, prokaryotic and eukaryotic promoters. Preferably bacterial, fungal, plant, insect or animal promoters, more preferably promoters known in the art used for cloning fragments of interest, like Lac promoters, or promoter useful for activity cloning or expression cloning (viral, archaeal, prokaryotic, eukaryotic).

More preferred promoters are Bla, T7, Pcat, pBAD, hybrid promoters, SP6, AOX, ADH, GAL, TRP1, CMV EF1a, and SV40; most preferred promoters are Bla, T7, Pcat, hybrid promoters, SP6, AOX, ADH, GAL, CMV, and SV40. A highly preferred promoter is a promoter that comprises at least one cleavage site from the first plurality of cleavage sites.

Vectors with a promoter that is configured to be operably linked to an insert can readily express a polynucleotide sequence encoded on that insert. Vectors that are intended for use solely in insert amplification have no use for a promoter and are more efficiently amplified when no such excess sequence is present.

Origin of Replication

An origin of replication (also called the replication origin, or Ori) is a particular sequence in a genome, a plasmid, or a vector at which replication is initiated. This can either involve the replication of DNA in living organisms such as prokaryotes and eukaryotes, or that of DNA or RNA in viruses, such as double-stranded RNA viruses. Oris can vary between organisms. They commonly feature a distinctive region containing a higher than average number of adenine and thymine residues (the AT-rich region) where, during the process of replication initiation, the initial destabilization (opening) of the double helix takes place.

In preferred embodiments, the backbone according to the invention comprises a polynucleotide that encodes a functional Ori, preferably wherein the Ori comprises at least one cleavage site from the first plurality of cleavage sites, or wherein preferably the Ori is immediately preceded and followed by a cleavage site from the first plurality of cleavage sites. This allows fragmentation of the Ori, or its immolation into a distinct fragment that is sufficiently small to allow practice of the invention. Accordingly, when the Ori has a length more than the desired size of degraded fragments, such as more than 1000 bp, it should contain a cleavage site from the first plurality; if not, it can be preceded and followed by such a cleavage site to allow efficient fragmentation of the backbone comprising such an Ori.

A functional Ori as used herein is an Ori that allows replication of a vector it is comprised in. Functionality of an Ori is preferably expressed as a percentage, wherein the percentage represents the relative copy number at which a vector is maintained when comprising a mutated Ori as compared to the copy number of a vector comprising that Ori it is derived from, such as the wildtype Ori, or such as the Ori as it is known in the art. Preferably, a functional Ori allows a plasmid to be maintained at a copy number that is at least about 0.01% of the copy number that would be achieved with the Ori it is derived from, preferably under conditions as described in the examples. More preferably, the copy number is at least 0.1%, 1%, 5%, 10%, 25%, 50%, 75%, 80%, 85%, 90%, 95%, or 100%. Even more preferably, the copy number is at least 5%, 10%, 25%, 50%, 75%, 80%, 85%, 90%, 95%, or 100%; still more preferably it is at least 10%, 25%, 50%, 75%, 80%, 85%, 90%, 95%, or 100%. In preferred embodiments, the copy number in pSC is at least 3, 4, or 5, more preferably at least 5. In preferred embodiments, the copy number in pMB is at least 10, 11, 12, 13, 14, or 15, more preferably at least 15. In preferred embodiments, the copy number in pUC is at least 350, 400, 450, or 500, more preferably at least 500. In preferred embodiments, the copy number in *E. coli* is at least 3, 4, or 5, more preferably at least 5; this is preferable for backbones derived from pSC. In preferred embodiments, the copy number in *E. coli* is at least 10, 11, 12, 13, 14, or 15, more preferably at least 15; this is preferable for backbones derived from pMB. In preferred embodiments, the copy number in *E. coli* is at least 350, 400, 450, or 500, more preferably at least 500; this is preferable for backbones derived from pUC.

The polynucleotide encoding a functional Ori is preferably derived from a yeast, bacterial, or viral Ori, such as from any one of SEQ ID NOs: 20-26. Such a sequence preferably has 70, 75, 80, 85, 90, 91, 92, 93, 94, 95, 96, 97, 98, 99, or 100% sequence identity with the selected SEQ ID NO, more preferably it has 90, 91, 92, 93, 94, 95, 96, 97, 98, 99, or 100% sequence identity, even more preferably it has 95, 96, 97, 98, 99, or 100% sequence identity, most preferably it has 98, 99, or 100% sequence identity, such as 99% or 100% sequence identity. In more preferred embodiments, the polynucleotide encoding a functional Ori has at least 70, 75, 80, 85, 90, 91, 92, 93, 94, 95, 96, 97, 98, 99, or 100% sequence identity with any one of SEQ ID NOs: 27-29, even more preferably from any one of SEQ ID NOs: 27-28. This sequence identity is preferably at least 90%, more preferably at least 95%, still more preferably at least 98%, most preferably 99% or 100%, such as 100%.

A backbone with an Ori is useful for amplification of the backbone or of a vector comprising a backbone and an insert. A backbone without an Ori is useful in gene therapy, or when an Ori is encoded by the (intended) fragment of interest, or in case of preparative PCR.

Expression Enhancing Elements

Specific additional polynucleotide sequences can increase the utility of a backbone according to the invention, or of an insert for use in the invention; particularly, certain polynucleotide sequences can enhance the expression of polypeptides or RNAs encoded by vectors comprising a backbone according to the invention, or of systems into which inserts for use in the invention are inserted after their isolation from a self-immolative backbone. These enhancing polynucleotide sequences are referred to herein as expression enhancing polynucleotides. In preferred embodiments is provided a recombinant polynucleotide vector according to the invention, wherein the backbone according to the invention or preferably the polynucleotide insert (that is: the polynucleotide for use in the invention) comprises an expression enhancing polynucleotide having at least 70% sequence identity with any one of SEQ ID NOs: 30-67. In more preferred embodiments, the expression enhancing polynucleotide has at least 75, 80, 85, 90, 91, 92, 93, 94, 95, 96, 97, 98, 99, or 100% sequence identity with any one of SEQ ID NOs: 30-35, 37, 51-60, 63-65, and 67, even more preferably at least 90%, more preferably still at least 95%, most preferably at least 98%, such as 100%. A preferred expression enhancing element is an expression enhancing element that comprises no cleavage site from the first plurality of cleavage sites.

Examples of expression enhancing polynucleotides are known in the art. For example, EP1432808 discloses SEQ ID NO: 30, which enhances expression of sequences of interest of which it is comprised in the 5'UTR. Another example is WO2012044171, which discloses SEQ ID NO: 31, which enhances expression of sequences of interest of which it is comprised in the 5'UTR. Another example is WO2015102487, which discloses nucleic acid sequences encoding a first promoter, a second promoter, and an optional nucleotide sequence of interest, wherein said first promoter and second promoters are configured to be both operably linked to said optional nucleotide sequence of interest, and wherein said second promoter is an intronic promoter, flanked by a first intronic sequence located upstream of said promoter and a second intronic sequence located downstream of said promoter. Exemplary embodiments of such dual promoter constructs featuring both a conventional promoter and an intronic promoter are represented by SEQ ID NOs: 55-58. Preferred examples of further expression enhancing polynucleotides are SEQ ID NOs: 59-67.

Selection and Design of Functional Elements

Functional elements as described herein often comprise a cleavage site from the first plurality of cleavage sites. This is because the polynucleotides encoding the functional elements can have a size that is larger than the intended size of the fragments. To introduce a cleavage site into a polynucleotide that encodes a polypeptide, it is most convenient to analyze the sequence of the functional element to find sequences that already have high sequence identity with the sequence of an intended cleavage site. For example when it is intended to introduce the cleavage site GAATTC (the restriction recognition site for the restriction endonuclease EcoRI) in a polynucleotide, it is convenient to analyze the polynucleotide for sequences of six nucleotides that already share 3, 4, 5, or all 6 of those nucleotides; preferably that already share 5 or 6 of those nucleotides. When 6 nucleotides are shared, no mutations are required. When 5 nucleotides are shared, only a single mutation is required. For such screening it is convenient to use freely available online tools, such as REBASE (Roberts et al., *Nucleic Acids Research,* 43 D1, 2015, D298-D299, DOI: 10.1093/nar/gku1046), where nucleotide sequences can be compared (blasted) against known restriction enzyme recognition sites.

Conversely, when analysis of a polynucleotide sequence reveals a sequence known to be a possible cleavage site, it can be convenient to consider this cleavage site to be a cleavage site of the first plurality. Use of its associated cleavage means will contribute to fragmentation of the functional element comprising said cleavage site. For example, when a given restriction recognition site is natively present in a marker, introduction of this restriction recognition site in other regions of the backbone according to the invention can facilitate backbone design. Screening of polynucleotide sequences can be done using freely available online tools, such as NEBcutter (Vincze et al., *Nucleic Acids Res.* 31: 3688-3691 (2003)).

It is preferable to introduce a silent mutation that introduces the cleavage site. A silent mutation is a mutation in a polynucleotide that does not alter the encoded polypeptide. Silent mutations are known in the art, and can be made based on the known codon tables.

When no silent mutations can be made, conservative mutations can be made wherein an encoded amino acid residue is mutated to a similar amino acid residue. Conservative mutations are known in the art, and for example preserve residue charge, polarity, or size. Examples of conservative mutations are Arg to Lys, Glu to Asp, Asn to Gln, Gly to Ala, Ser to Thr, Leu to Ile, etc. Non-silent mutations are preferably made in unordered regions of the encoded polypeptide, such as in random coils or close to a terminus such as the N-terminus.

When neither silent nor conservative mutations can be made to introduce a cleavage site, a non-conservative mutation or an insertion of an amino acid residue can be made. Preferred amino acid residues for insertion are small, uncharged amino acid residues such as Ala, Gly, Ser, or Thr, preferably Ala, Ser, or Thr, more preferably Thr. For example, the dipeptide Thr-Arg can be encoded by ACGCGT, which is a recognition site for the MluI restriction endonuclease. Thus, when an encoded polypeptide comprises Arg, insertion of Thr can lead to insertion of a cleavage site, namely the MluI restriction site. Similarly, when an encoded polypeptide comprises Thr, insertion of Arg can lead to insertion of a cleavage site. Insertion of Thr is preferred because it is known in the art that insertion of small, uncharged residues is less likely to disrupt the functionality of a polypeptide. The effect of a mutation, when not a silent mutation, can be assessed using any method known in the art. Examples of mutation planning and assessment are for example given by Morrison and Weiss (2001) "Combinatorial alanine-scanning" *Curr Opin Chem Biol* 5(3): 302-7, DOI: 10.1016/S1367-5931 (00)00206-4.

When a cleavage site is to be introduced in a functional element that does not encode a polypeptide, it is preferred to introduce a cleavage site through a mutation that preserves known sequence motifs. For example, a mutation in an AT-rich region preferably introduces either T or A. For example, when a mutation known to be in the stem of a stem-loop region is introduced, it is preferably accompanied by a complementarity-preserving mutation in the base pairing residue at the other arm of the stem.

A skilled person knows how to introduce specific mutations in a polynucleotide, and polynucleotides with custom sequences are commercially available from various contract suppliers. Once a self-immolative functional element or a backbone according to the invention has been designed, it can be tested for functionality using routine techniques. For example, a backbone comprising a selection marker can be subjected to the associated selection pressure. Alternatively, a self-immolative backbone can be equipped with an insert encoding a reporter polypeptide operably linked to a promoter. In such a case, the expression of the reporter polypeptide is correlated to backbone functionality. Examples of reporter polypeptides are fluorescent proteins such as GFP or DsRed, and enzymes that can be easily assayed such as alkaline phosphatase, secreted alkaline phosphatase (SeAP), or luciferase.

In preferred embodiments a backbone according to the invention or an insert for use in the invention comprises a polynucleotide encoding an origin of replication, a polynucleotide encoding a promoter, a polynucleotide encoding a functional marker, an expression enhancing polynucleotide, and a polynucleotide encoding a multiple cloning site; more preferably the origin of replication, the multiple cloning site, and the functional marker are comprised in the backbone according to the invention, and the expression enhancing nucleotide and optionally the promoter are more preferably comprised in the insert for use in the invention.

In preferred embodiments a backbone according to the invention or an insert for use in the invention comprises a polynucleotide encoding an origin of replication, a polynucleotide encoding a functional marker, an expression enhancing polynucleotide, and a polynucleotide encoding a multiple cloning site; more preferably the origin of replication, the multiple cloning site, and the functional marker are comprised in the backbone according to the invention, and the expression enhancing nucleotide is more preferably comprised in the insert for use in the invention.

In preferred embodiments a backbone according to the invention or an insert for use in the invention comprises a polynucleotide encoding an origin of replication, a polynucleotide encoding a functional marker, and a polynucleotide encoding a multiple cloning site; more preferably the origin of replication, the multiple cloning site, and the functional marker are comprised in the backbone according to the invention.

In preferred embodiments a backbone according to the invention or an insert for use in the invention comprises a polynucleotide encoding an origin of replication, and a polynucleotide encoding a functional marker; more preferably the origin of replication and the functional marker are comprised in the backbone according to the invention.

In preferred embodiments a backbone according to the invention or an insert for use in the invention comprises a polynucleotide encoding an origin of replication, a polynucleotide encoding a functional marker, and a polynucleotide encoding a multiple cloning site, wherein the cleavage sites are endonuclease recognition sites; more preferably the origin of replication, the multiple cloning site, and the functional marker are comprised in the backbone according to the invention.

In preferred embodiments a backbone according to the invention or an insert for use in the invention comprises a polynucleotide encoding an origin of replication, and a polynucleotide encoding a functional marker, wherein the cleavage sites are endonuclease recognition sites; more preferably the origin of replication and the functional marker are comprised in the backbone according to the invention.

In preferred embodiments a backbone according to the invention or an insert for use in the invention comprises a polynucleotide encoding an origin of replication, a polynucleotide encoding a functional marker, and a polynucleotide encoding a multiple cloning site, wherein the cleavage sites are endonuclease recognition sites, and wherein the fragments have a length of at most 650 bp, preferably of at most 450 bp, more preferably of at most 350 bp, most preferably of at most 200 bp; more preferably the origin of replication, the multiple cloning site, and the functional marker are comprised in the backbone according to the invention.

In preferred embodiments a backbone according to the invention or an insert for use in the invention comprises a polynucleotide encoding an origin of replication, and a polynucleotide encoding a functional marker, wherein the cleavage sites are endonuclease recognition sites, and wherein the fragments have a length of at most 650 bp, preferably of at most 450 bp, more preferably of at most 350 bp, most preferably of at most 200 bp; more preferably the origin of replication and the functional marker are comprised in the backbone according to the invention.

Within this aspect the invention also provides compositions comprising a backbone according to the invention or a vector according to the invention, and further comprising at least one physiologically acceptable excipient. Examples of physiologically acceptable excipients are water, purified water, and aqueous buffers, for example buffers such as described elsewhere herein.

Method of Using the Backbone

The backbones according to the invention allow efficient isolation of inserts. Methods of using backbones according to the invention therefore focus on this separation. Such methods can be used for efficient preparation of any insert, such as a polynucleotide encoding a polypeptide of interest, or a specific homology-directed repair (HDR) template DNA in CRISPR/Cas mediated DNA-editing, or for preparation of RNA for use in synthetic biology or pharmacy. Such methods can also be used to prepare (circular) RNA for use in e.g. synthetic biology [Programming cells and tissues. New toolkits of biological parts allow powerful cell programming by synthetic biologists DS Glass and U Alon Science (21 Sep. 2018) 361, 1199-1200].

Accordingly, in another aspect, the invention provides a method for separating a polynucleotide insert from a polynucleotide vector backbone, the method comprising the steps of i) providing a recombinant polynucleotide vector comprising the insert and the vector backbone, wherein the vector backbone comprises a first plurality of cleavage sites that divide the vector backbone into fragments having a length of at most 1000 bp;
ii) contacting the recombinant vector with cleavage means capable of specifically cleaving the first plurality of cleavage sites to produce backbone fragments; and optionally, iii) separating the insert from the backbone fragments of step ii). Such a method is referred to herein as a method according to the invention. These steps are preferably performed in numerical order.

Step i)—Provision of a Self-Immolative Vector

The vector, backbone, and insert of step i) are a vector according to the invention, a backbone according to the invention, and an insert for use according to the invention as described elsewhere herein. Accordingly, in preferred embodiments is provided the method according to the invention, wherein the cleavage sites are restriction endonuclease recognition sites. In preferred embodiments is provided the method according to the invention, wherein the insert does not comprise a cleavage site of the first plurality of cleavage sites. Effectively this ensures that when the first plurality of cleavage sites is cleaved, the insert is not cleaved because it has no matching cleavage site that is comprised in the first plurality of cleavage sites. In other words, in preferred embodiments the insert does not comprise a cleavage site that is also comprised in the first plurality of cleavage sites, or does not comprise a cleavage site that also exists in the first plurality of cleavage sites. In preferred embodiments is provided the method according to the invention, wherein the vector backbone further comprises a polynucleotide encoding a functional marker, wherein the polynucleotide encoding a functional marker is preferably selected from SEQ ID NOs: 14-18. In preferred embodiments is provided the method according to the invention, wherein the fragments have a length of at most 900, 800, 700, 650, 600, 550, 500, 450, 400, 350, 300, 250, 200, 150, or 100 bp or less, preferably of at most 550 bp, such as about 500 bp. In preferred embodiments is provided the method according to the invention, wherein the vector backbone comprises a multiple cloning site that does not comprise a cleavage site of the first plurality of cleavage sites. Preferred backbones according to the invention as described herein are preferred for use in a method according to the invention.

Provision of the vector can be from any source. Typically, the vector will be a vector that has been isolated from a culture, wherein the culturing was performed for the purpose of amplifying the vector. In preferred embodiments, the vector is in a composition. In preferred embodiments, the vector has been isolated from a microbial culture, more preferably from a bacterial culture. In preferred embodiments, the vector is in purified water or in a physiologically acceptable aqueous buffer, preferably a buffer that is compatible with the cleavage means of step ii).

Step ii)—Degrading the Backbone

In step ii) the self-immolative vector that was provided in step i) is degraded into its fragments, liberating the insert. This is because in step ii) the recombinant vector is contacted with cleavage means capable of specifically cleaving the first plurality of cleavage sites to produce backbone fragments. Suitable cleavage means have been described earlier herein. In preferred embodiments is provided the method according to the invention, wherein the cleavage means are selected from the group consisting of a restriction enzyme, an RNA-guided DNA endonuclease enzyme, a sequence-specific nuclease, sequence-specific ultrasonication, a sequence-specific oxidative small molecule such as bleomycin, and a sequence-specific hydrolyzing small molecule such as a lanthanide complex; more preferably the cleavage means are selected from the group consisting of a restriction enzyme, an RNA-guided DNA endonuclease enzyme, and a sequence-specific nuclease; even more preferably the cleavage means are selected from the group consisting of a restriction enzyme and an RNA-guided DNA endonuclease enzyme, most preferably a restriction enzyme.

The contacting of step ii) amounts to using the cleavage means according to its known use. Commonly, the contacting entails the addition of the vector of step i) to a suitable reaction buffer comprising an effective amount of the cleavage means; conversely an effective amount of the cleavage means can be added to a suitable reaction buffer comprising the vector of step i). Suitable buffers depend on the cleavage means and are well known in the art. For example, when the cleave means comprise restriction enzymes, a suitable buffer can be CutSmart (registered trademark) buffer from New England BioLabs (NEB), which comprises 50 mM potassium acetate, 20 mM tris-acetate, 10 mM magnesium acetate, 100 μg/ml BSA, pH 7.9 at 25° C.; another suitable buffer is restriction enzyme buffer SH from Sigma-Aldrich (PubChem Substance ID 24891729); other suitable buffers are described in Khan et al., cited earlier herein. The use of cleavage means per se to cleave a polynucleotide is broadly known in the art, and a skilled person can select suitable conditions to perform the cleavage.

The cleavage means specifically cleave the cleavage sites of the first plurality. This means that only the cleavage sites of the first plurality are cleaved, which degrades the vector into its constituent fragments, resulting in a mixture comprising said fragments and further comprising the insert. Because the insert is devoid of cleavage sites of the first plurality, it is not cleaved into smaller fragments, allowing easy separation of the insert from the smaller backbone fragments. Because the cleavage means are specific for the cleavage sites of the first plurality, no other polynucleotide products are produced besides the fragments and the insert.

In preferred embodiments is provided the method according to the invention, wherein the cleavage means comprise 3, 2, or 1 species of restriction enzymes, preferably wherein the restriction enzyme recognizes a restriction site of 6 or 7 nucleotides, more preferably selected from the group consisting of BstZ17I and MluI. More preferred embodiments provide the method according to the invention, wherein the first plurality of cleavage sites comprises only restriction sites, and comprises no more than 6, 5, 4, 3, 2, or 1, preferably no more than 3, 2, or 1, more preferably no more than 2 or 1, most preferably comprises only 1, species of restriction site, wherein the restriction sites are preferably selected from the group consisting of restriction sites for restriction enzymes as defined earlier herein, most preferably selected from restriction sites for BstZ17I and MluI.

Step iii)—Isolation of the Insert

Step iii) is an optional step wherein the insert is isolated, that is wherein it is separated from the backbone fragments of step ii). In preferred embodiments of the method according to the invention, step iii) is included. An advantage of the invention is that the insert has a size that is larger, often substantially larger, than that of any other polynucleotide present in the mixture from which the insert is to be isolated. In conventional insert isolation the insert is often smaller than the opened vector backbone, or both molecules can have a similar size. This means that for conventional insert isolation gel extraction is often the most likely choice of separation technique.

In molecular biology, "gel extraction" or gel isolation is a technique used to isolate a desired fragment of intact DNA from an agarose gel following agarose gel electrophoresis. An example of gel extraction is described in the examples, where it is used as a reference technique. Gel extraction is laborious, requires manual dexterity, and is prone to contaminate the isolated insert with for example chemical contaminants, as described in the example. In preferred methods according to the invention, step iii) does not comprise gel extraction, or does not comprise preparative gel electrophoresis. In this context, preparative gel electrophoresis is electrophoresis that is performed with the intent of later isolating a fraction from the gel.

In preferred embodiments is provided the method according to the invention, wherein the separation of step iii) uses a technique selected from a spin column, a size exclusion column, and solid phase reversible immobilization (SPRI). Preferred separation techniques are a spin column, a size exclusion column, and solid phase reversible immobilization (SPRI); a spin column is most preferred, for its convenience.

The size difference between the insert and the fragments allows convenient separation using size exclusion techniques. Size exclusion techniques are known in the art, for example as described by Potschka (Macromolecules, 1991, 24(18), pp 5023-5039, DOI: 10.1021/ma00018a008). Size exclusion techniques generally use a column material. The smaller fragments can be captured in or by the column material, while the larger insert elutes with a low retention time. Inversely, the smaller fragments can elute in void volume while the larger insert is captured in or by the column material owing to its size. This latter technique can also be seen as a solid phase extraction, or solid phase reversible immobilization (SPRI), because it relies on the fact that the larger insert binds to the column material, often silica, owing in part to its size, while the smaller fragments do not bind. Later elution of the insert then allows its isolation. Examples of size exclusion techniques are size exclusion chromatography using a spin column, and size exclusion chromatography using a size exclusion column. A size exclusion column is generally used on a benchtop, and liquids flow through it under gravitational force or under action of a pump. The use of such columns is described in handbooks cited elsewhere herein.

A spin column is generally a disposable miniaturized size exclusion column that can be mounted on a receptacle fit for use in a centrifuge. Once the spin column is filled with sample it can be centrifuged to drive the sample through the size exclusion material. The spin column can then optionally be filled with additional volumes of buffer and centrifuged further times. Spin columns are widely commercially available and are well known, for example as described in Shi et al., PLOS ONE, 2018, DOI: 10.1371/journal.pone.0203011. Spin columns can be columns that retain, such as bind or capture, the fragments, for example in size exclusion material only permeable to small fragments, or due to complementarity to sticky ends of the fragments. Spin columns can also be columns that do not retain the backbone fragments, for example in solid phase reversible immobilization of the insert. Spin columns that retain the fragments and that do not retain the inserts are preferred, particularly spin columns with size exclusion material that captures the fragments.

Alternately the fragments can be removed from the mixture by fragment pulldown based on sticky overhang hybridization. If the cleavage means leads to sticky ends for the fragments it generates, these sticky ends can be used to pull down those fragments. Generally, in such a technique, the fragments associate with a solid-phase carrier complementary to the sticky overhangs. Later removal of the solid-phase carrier thus removes the fragments, leaving the isolated insert in solution.

The separation techniques as described above, and the materials for use in such separation techniques, are known in the art. A skilled person can select an appropriate technique, and can select appropriate materials for use in such a technique. The separation technique of choice preferably provides the insert with a purity of at least 50%, 60%, 70%, 75%, 80%, 85%, 90%, 95%, 96%, 97%, 98%, 99%, 99.5%, 99.6%, 99.7%, 99.8%, 99.9%, or higher, such as 100%. More preferably a purity of at least 95%, 96%, 97%, 98%, 99%, 99.5%, 99.6%, 99.7%, 99.8%, 99.9%, or higher is obtained, even more preferably of at least 99% or higher, most preferably of at least 99.7% or higher.

Method for Amplifying an Insert

The use of a backbone according to the invention also allows the convenient amplification of an insert. In another aspect the invention provides a method for amplifying a polynucleotide of interest, the method comprising the steps of i) providing a recombinant polynucleotide vector comprising the polynucleotide of interest as an insert, and a vector backbone according to the invention;
ii) amplifying the recombinant polynucleotide vector of step i) by transforming a suitable microorganism with it and culturing said transformed microorganism in a culture medium under conditions suitable for vector amplification to obtain amplified recombinant polynucleotide vector;
iii) isolating the amplified recombinant polynucleotide vector from the culture medium of step ii) to obtain isolated amplified recombinant polynucleotide vector;
iv) contacting the isolated amplified recombinant polynucleotide vector with cleavage means capable of cleaving the first plurality of cleavage sites to produce backbone fragments; and optionally,
v) separating the nucleotide sequence of interest from the backbone fragments of step iv).

This method is referred to herein as a production method according to the invention. Its steps are preferably performed in numerical order.

In step i) a vector according to the invention is provided, which comprises the polynucleotide of interest as an insert, and which further comprises a backbone according to the invention. Preferably, the vector consists of said insert and said backbone.

In step ii) this vector is transformed into a suitable microorganism. In preferred embodiments the recombinant vector is transected to a suitable microorganism. A skilled person is well aware of which microorganisms can be used for vector amplification, such as *E. coli* or a suitable yeast or fungus—numerous handbooks on the topic exist, such as Sambrook et al., Molecular cloning: a laboratory manual. New York: Cold spring harbor laboratory press, 1989; or Green and Sambrook, 2012, ISBN 978-1-936113-42-2. Similarly, transformation and transfection are known in the art, and can be performed in any way a skilled person sees fit, for example such as described in Sambrook et al. Examples of suitable transfection methods are transfection using transfection lipids such as those described in Damen et al., (MedChemComm 2018, 9(9):1404-1425, DOI: 10.1039/c8md00249e), using transfection polymers such as described in Zhang and Wagner (Top. Curr. Chem. 2017, 375(2):26, DOI: 10.1007/s41061-017-0112-0), electroporation, transformation using competent or supercompetent cells, microinjection, gene bombardment, et cetera. After this transformation the transformed microorganism comprising the vector is cultured to amplify the vector. Again, such steps are broadly known in the art and a skilled person can select the appropriate steps by routine selection, optionally guided by the sources cited above.

In step iii) the amplified vector is isolated. The amplified vector comprises the insert, which has been amplified along with the vector as it is therein comprised. Isolation of a vector from a microorganism is a standard procedure that is commonly known, and can be performed in any way a skilled person sees fit, optionally guided by the sources cited above, or by the examples described later herein. Suitable methods are plasmid preparation such as miniprepration, midipreparation, or maxipreparation, for example as described by Birnboim and Doly (1979) Nucleic Acids Res. 7(6): 1513-23, DOI: 10.1093/nar/7.6.1513.

In step iv) of the production method according to the invention the isolated vector according to the invention is degraded or immolated, similar to step ii) of the method according to the invention. Features and definitions as provided there are also applicable for step iv) of the production method according to the invention.

In step v) of the production method according to the invention, which is an optional step, the insert is isolated, that is it is separated from the backbone fragments of step iv). In preferred production methods according to the invention, step v) is included. This step is substantially similar to step iii) of the method according to the invention. Features and definitions as provided there are also applicable for step iv) of the production method according to the invention.

Use of the Backbone or Vector

The backbone according to the invention and the vector according to the invention can be used in methods according to the invention, or in production methods according to the invention. Accordingly, in a further aspect the invention provides use of a polynucleotide vector backbone according to the invention, or of a recombinant polynucleotide vector according to the invention, for the purification of a polynucleotide insert.

The invention also provides use of a cleavage means for converting a polynucleotide vector comprising an insert and a vector backbone into:

fragments having a length of at most 1000 bp; and the separate insert. Features and definitions have been provided elsewhere herein.

This use is particularly envisioned for cleavage means such as RNA-guided DNA endonuclease enzymes, which can be configured to recognize any particular sequence as a cleavage site.

In preferred embodiments the backbone according to the invention is used in a method for enhancing transcription of a nucleotide sequence of interest in a eukaryotic cell, the method comprising the steps of:

i) providing a recombinant polynucleotide vector comprising the polynucleotide of interest as an insert, and a vector backbone according to the invention;
ii) amplifying the recombinant polynucleotide vector of step i) by transfecting it to a suitable microorganism and culturing said microorganism in a culture medium under conditions suitable for vector amplification to obtain amplified recombinant polynucleotide vector;
iii) isolating the amplified recombinant polynucleotide vector from the culture medium of step ii) to obtain isolated amplified recombinant polynucleotide vector;
iv) contacting the isolated amplified recombinant polynucleotide vector with cleavage means capable of cleaving the first plurality of cleavage sites to produce backbone fragments;
v) separating the nucleotide sequence of interest from the backbone fragments of step iv) to obtain an isolated nucleotide sequence of interest;
vi) integrating the isolated nucleotide sequence of interest in the genome of a eukaryotic cell, preferably a mammalian cell or an insect cell, to obtain a transgenic cell;
vii) culturing the transgenic cell under conditions conducive to expression of the nucleotide sequence of interest.

For steps i) through v) features and definitions as described above apply. In step vi) the isolated nucleotide sequence of interest is integrated into the genome of a eukaryotic cell to obtain a transgenic cell. This can be done via any means known in the art, such as via lipid transfection or electroporation, more preferably such as described in Example 4.3. In preferred embodiments a pool of transgenic cells is obtained. In step vii) the transgenic cell, or optionally the pool of transgenic cells, is cultured to express the nucleotide sequence of interest. Preferably, this expression is higher than expression of the amplified recombinant polynucleotide vector of step iii) when it has been not been degraded as in step iv), but has instead been linearized, for example using a restriction enzyme for which only a single restriction site was present in the backbone.

Kit of Parts

The backbones and vectors according to the invention can be provided as components in a kit of parts. Therefore, in another aspect the invention provides a kit of parts comprising:

i) a polynucleotide vector backbone according to the invention, or a recombinant polynucleotide vector according to the invention; and at least one of
iia) materials for use in a separation technique as defined elsewhere herein, such as spin filters; or
iib) cleavage means as defined elsewhere herein.

Such a kit is referred to herein as a kit according to the invention.

A kit according to the invention always comprises a polynucleotide vector backbone according to the invention, or a recombinant polynucleotide vector according to the invention. It can have various further parts, described above as iia or iib. In preferred embodiments, both the parts of iia and iib are comprised.

The further parts under iia are materials for use in separating the fragments from the insert. Such materials have been described under step ii) of the method according to the invention.

The further parts under iib are cleavage means, preferably at least all cleavage means required for immolation of the vector or backbone according to the invention. The cleavage means are preferably provided in a suitable separate container. In preferred embodiments the cleavage means are restriction enzymes, and are provided in plastic containers suitable for subzero storage. Suitable containers for each cleavage means are known in the art, and can be selected based on the cleavage means that is to be contained.

Method for Designing a Self-Immolative Backbone

The invention further relates to a method for designing a backbone according to the invention, the method comprising steps selected from:

i) providing a polynucleotide vector backbone;
ii) screening the provided vector backbone for endonuclease restriction sites;
iii) screening the provided vector backbone for sequences that share 4, 5, 6, or 7 nucleotides with an endonuclease restriction site;
iv-a) implementing at least one silent mutation in the provided vector backbone to convert a sequence of step iii) into an endonuclease restriction site; and/or
iv-b) implementing at least one mutation in the provided vector backbone to convert a sequence of step iii) into an endonuclease restriction site.

Reduction to practice of this method is demonstrated in the Examples. Features and definitions are as described elsewhere herein. Preferably, the method comprises steps i), ii), iii), and at least one of iv-a) and iv-b); more preferably the method comprises steps i), ii), iii), and iv-a). Steps are preferably performed in numerical order.

The silent mutation of step iv-a) is a mutation that alters the oligonucleotide sequence, preferably to introduce an endonuclease restriction site, while not altering the amino acid sequence of an encoded polypeptide, or alternately while not substantially altering the functionality of an encoded polypeptide or of the oligonucleotide sequence. Alteration of functional elements and their functionality is described elsewhere herein.

The mutation in step iv-b) can be the insertion, deletion, or mutation of any residue in the polynucleotide. In preferred embodiments it is the insertion of a codon to introduce an amino acid, or the mutation of one or more nucleotides to alter a codon for one amino acid to a codon for another amino acid. Preferably, this alteration of codons leads to a conservative mutation of amino acids, such as from a charged amino acid to another amino acid with a similar charge, or from a small amino acid to another small amino acid. Conservative mutations are known in the art.

General Definitions

The term "derived from" in the context of being derived from a particular naturally occurring gene or sequence is defined herein as being chemically synthesized according to a naturally occurring gene or sequence and/or isolated and/or purified from a naturally occurring gene or sequence. A species derived from another species is preferably mutated, in that at least one residue of an amino acid sequence, or of a polynucleotide, or of a polynucleotide encoding the amino acid sequence, is not the same as in the naturally occurring gene or sequence. Techniques for chemical synthesis, isolation and/or purification of nucleic acid molecules are well known in the art. In general, a derived sequence is a partial sequence of the naturally occurring gene or sequence or a fraction of the naturally occurring gene or sequence. Optionally, the derived sequence comprises nucleic acid substitutions or mutations, preferably resulting in a sequence being at least 50%, 55%, 60%, 65%, 70%, 75%, 80%, 85%, 90%, 91%, 92%, 93%, 94%, 95%, 96%, 97%, 98% or 99% identical over its whole length to the naturally occurring gene partial gene or sequence or partial sequence.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value more or less 1% of the value.

Whenever a parameter of a substance is discussed in the context of this invention, it is assumed that unless otherwise specified, the parameter is determined, measured, or manifested under physiological conditions. Physiological conditions are known to a person skilled in the art, and comprise aqueous solvent systems, atmospheric pressure, pH-values between 6 and 8, a temperature ranging from room temperature to about 37° C. (from about 20° C. to about 40° C.), and a suitable concentration of buffer salts or other components.

In the context of this invention, a decrease or increase of a parameter to be assessed preferably means a change of at least 5% of the value corresponding to that parameter. More preferably, a decrease or increase of the value means a change of at least 10%, even more preferably at least 20%, at least 30%, at least 40%, at least 50%, at least 70%, at least 90%, or 100%. In this latter case, it can be the case that there is no longer a detectable value associated with the parameter.

"Sequence identity" or "identity" in the context of amino acid- or nucleic acid-sequence is herein defined as a relationship between two or more amino acid (peptide, polypeptide, or protein) sequences or two or more nucleic acid (nucleotide, polynucleotide) sequences, as determined by comparing the sequences. In the art, "identity" also means the degree of sequence relatedness between amino acid or nucleotide sequences, as the case may be, as determined by the match between strings of such sequences. In this document, sequence identity with a particular sequence indicated with a particular SEQ ID NO preferably means sequence identity over the entire length of said particular polypeptide or polynucleotide sequence indicated with said particular SEQ ID NO.

However, sequence identity with a particular sequence indicated with a particular SEQ ID NO may also mean that sequence identity is assessed over a part of said SEQ ID NO. A part may mean at least 50%, 60%, 70%, 80%, 90% or 95% of the length of said SEQ ID NO. The sequence information as provided herein should not be so narrowly construed as to require inclusion of erroneously identified bases. The skilled person is capable of identifying such erroneously identified bases and knows how to correct for such errors.

"Identity" can be readily calculated by known methods, including but not limited to those described in Computational Molecular Biology, Lesk, A. M., ed., Oxford University Press, New York, 1988. Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, MD 20894; Altschul, S., et al., J. Mol. Biol. 215:403-410 (1990). The well-known Smith Waterman algorithm may also be used to determine identity. Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons. Preferred program and parameter for assessing identity for nucleic acid comparison is calculated using EMBOSS Needle Nucleotide Alignment algorithm with the following parameters: DNAfull matrix with the following gap penalties: open=10; extend=0.5.

The present invention has been described above with reference to a number of exemplary embodiments. Modifications and alternative implementations of some parts or elements are possible, and are included in the scope of protection as defined in the appended claims. All citations of literature and patent documents are hereby incorporated by reference.

DESCRIPTION OF DRAWINGS

FIG. 4—Separation of insert from backbone fragments by a ChromaSpin-1000 method. Input is MluI/BstZ17I digested vector (see Example 2). Lane 1: 2 Log marker; Lane 3: 100 μl 1.5 μg/μl Input; Lane 4: Flow-through.

EXAMPLES

Figure 1:
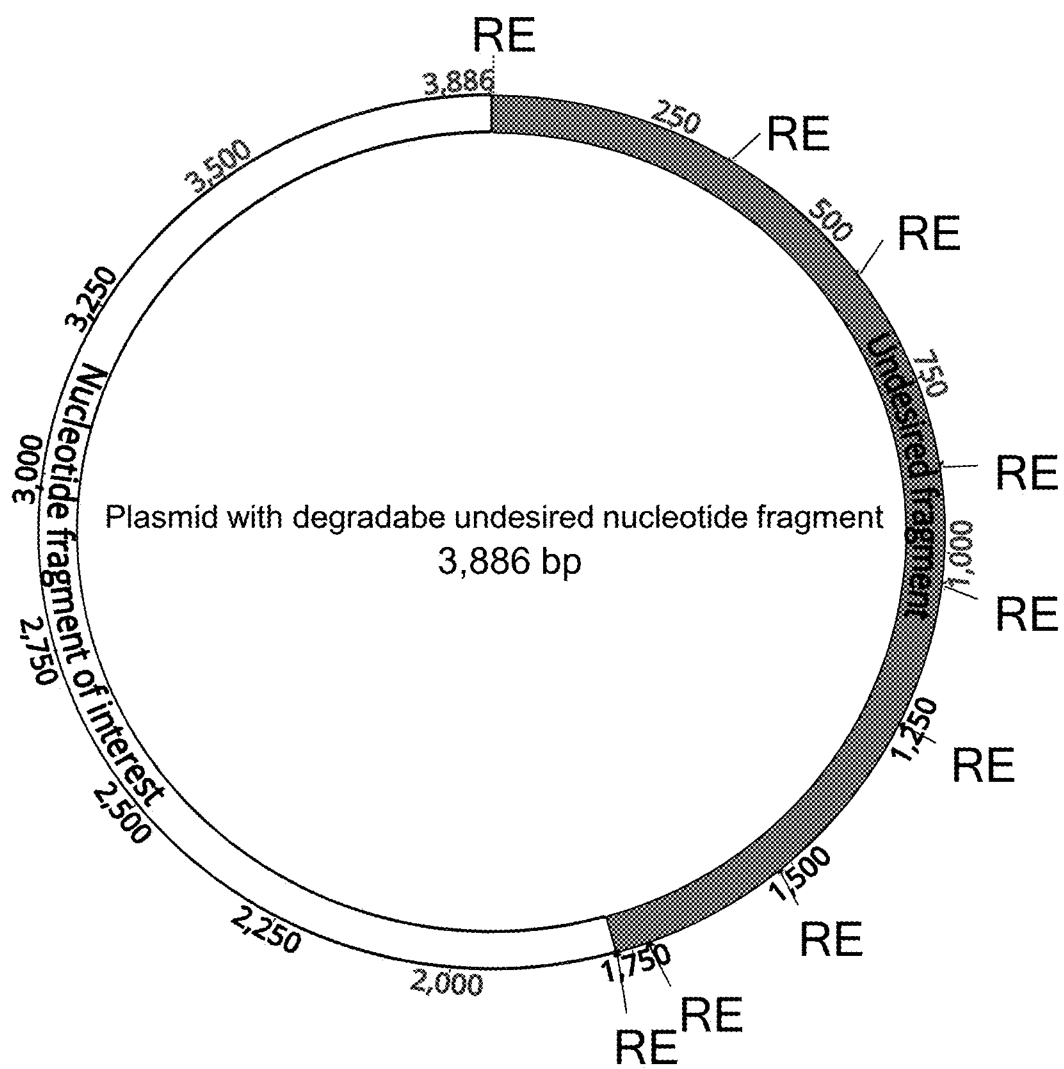
FIG. 1—Schematic representation of a backbone degradation primed plasmid. The undesired nucleotide sequence, e.g. bacterial backbone, is presented in grey; the fragment of interest is colourless. The backbone harbours regularly distributed cleavage sites such as recognition sites for restriction enzymes (indicated as RE). These sites are not present in the fragment of interest. Cleavage of the cleavage sites triggers degradation of the backbone, allowing one-step quantitative separation of the fragment of interest from the degraded undesired nucleotide sequence.
Figure 2:
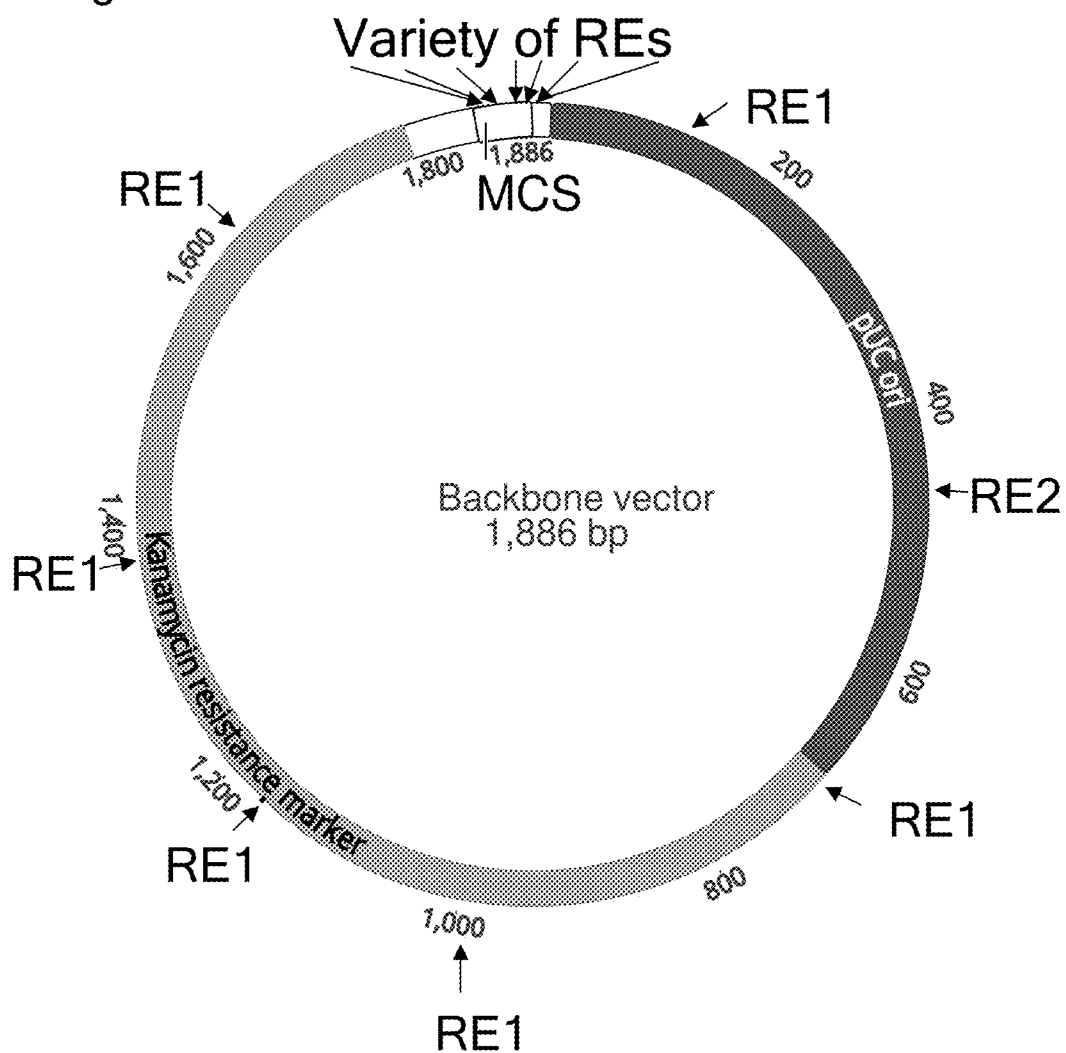
FIG. 2—Schematic representation of backbone degradation vector without fragment of interest. Functional units kanamycin marker (grey), origin of replication (black) and multiple cloning site (MCS, white) are indicated. The vector from example 1 has a kanamycin resistance gene as marker, and harbours restriction sites for MluI (indicated as RE1) and BstZ17I (indicated as RE2). After degradation of its sequence by restriction digestion the size of the backbone vector fragments ranges from 121 to 342 bp. The sequence of backbone vector of Example 1 is SEQ ID NO: 68.

Example 1—Design and Preparation of a Vector with a Self-Immolative Backbone 1.1 Design of a Vector: Introduction of Restriction Enzyme Sites in the Backbone A design for a vector comprising an insert was made by introducing cleavage sites, in this case restriction sites, for a minimal number of restriction enzymes resulting in fragments smaller than 350 bps. This fragment size allows one-step purification of fragments of interest with a size starting at 1500 bp and higher (see Example 2). The number of enzymes to be used as cleavage means was kept as low as possible to simplify the digestion process and to minimize the number of restriction sites that were to be avoided during synthesis and/or cloning of fragments-of-interest. In this example, two restriction enzymes were selected: MluI and BstZ17I.

While not essential features of all plasmids, typical functional elements of a cloning plasmid are the origin of replication (Ori), a marker, and a multiple cloning site (MCS). Outside of these functional elements, the introduction of restriction sites is relatively easy as no functionality is present. To obtain fragments of maximum 350 bp, introduction of restriction sites is required within the marker and the origin of replication.

1.2. Modification of Markers

Polynucleotides encoding for markers can be modified to allow cleavage sites to divide the coding sequence into fragments. In this example the kanamycin and ampicillin selection markers were divided into fragments of at most about 350 bp.

1.2.1 Self-Immolative Kanamycin

In Silico Gene Analysis and Options for Modification

The sequence of the selection marker gene was taken from GenBank JF826242.2. The kanamycin selection marker gene coding for aminoglycoside-3'-phosphotransferase (APH(3')) and its 816 nt coding sequence are annotated as nt 841-1656 (complement). At the 5' site of the coding sequence a 130 nt promoter sequence is present. The 145 nt sequence at the 3' of the coding DNA sequence (CDS) was also considered to be important for gene expression.

Four silent mutations were selected that introduce MluI sites, cutting the CDS into fragments smaller than 200 bp. No silent mutations could be made at the 5' end of the gene, resulting in a fragment of approximately 430 bp. To allow further digestion within this fragment, inclusion of a cleavage site such as MluI just inside the coding sequence was necessary. The N-terminal 10 amino acid sequence was selected as a target for mutations that would still yield APH(3') expression and activity. These first 10 amino acids (MSHIQRETSC—SEQ ID NO: 102) were highly promising, because they are unordered (D. Nurizzo et al., The crystal structure of aminoglycoside-3'-phosphotransferase-IIa, an enzyme responsible for antibiotic resistance. J Mol Biol (2003) 327, 491-506) and they apparently do not play a role in the structural function of the enzyme. Moreover, the amino acid sequence at the N-terminal end is not conserved, with different lengths and sequences occurring throughout known variants. Based on this the following two variants were designed: 1) MSHIQTRETSC (SEQ ID NO: 103, first 11 amino acids of SEQ ID NO: 69) with a Thr inserted; the dipeptide TR can be encoded by a MluI recognition site (ACGCGT) and 2) MSHIQRETRSC (SEQ ID NO: 104, first 11 amino acids of SEQ ID NO: 70) with an Arg inserted. These two variants, together with wild-type sequence, were tested for capacity to allow selection on kanamycin.

Experimental Gene Modifications, Functional and Sequence Analysis

Backbone plasmid was created using five geneblocks (Integrated DNA technologies (IDT), Leuven, Belgium, SEQ ID NOs: 71-75). The geneblocks were dissolved to 0.1 μM in water. Combinations forming a complete backbone (i.e. one variant or wildtype for each of the five fragments were made in 16 μl final reaction volume, containing 0.4 μl of each geneblock at 0.1 μM, 8 μl HiFi assembly mix (NEB E2621), and 6 μl of water (Sigma W4502). Mixtures were incubated 1 hr at 50° C., and stored at −20° C. till further use. Top10 chemically competent cells (Life Technologies C404010) were transformed according the manufacturer's instructions with 2 μl of the assembly reactions. Functionality of the kanamycin resistance gene, i.e. expression and activity of APH(3'), was tested by the ability of the plasmid to confer kanamycin resistance, which is observed by plating the transformants onto LB-Kan plates. Combinations were first made with 1 out of the 5 wildtype fragments replaced with a variant fragment.

In one fragment the four silent mutations in the kanamycin gene were introduced (SEQ ID: 76). Wildtype fragments were used to generate the reference plasmid. Introducing the four silent mutations did not adversely affect kanamycin resistance. Next, either the threonine (SEQ ID NO: 77, encoding the polypeptide of SEQ ID NO: 69) or the arginine insertion (SEQ ID NO: 78, encoding the polypeptide of SEQ ID NO: 70) was introduced to the plasmid with the four silent mutations. The insertion of threonine also resulted in proper transformants, while transformants with an arginine introduced in the N-terminal sequence of APH(3') were less viable. In subsequent experiments plasmids were used in which the four silent mutations and the threonine-inserted APH(3') are present.

1.2.2 Self-Immolative Ampicillin

The DNA sequence conferring ampicillin resistance to bacteria was redesigned to allow degradation into small fragments. Two silent mutations were introduced into the β-lactamase coding sequence to introduce MluI restriction sites. This lead to a division into fragments of 310, 352, and 524 bp. The resulting selection marker (SEQ ID NO: 79) can be used in backbones according to the invention, for example instead of the kanamycin marker described in Example 1.2.1. To obtain fragments smaller than 400 bp, single amino acid changes by introducing additional MluI and BstZ17I recognition sites were designed, so that the resulting fragments have sizes of at most 352 bp; the resulting selection marker has SEQ ID NO: 15. An example of a vector comprising this selection marker is SEQ ID NO: 80. This redesigned ampicillin resistance gene can be applied for use in a plasmid with a self-immolative backbone. Other suitable self-immolative functional ampicillin variants with one or more altered amino acid were designed and functional: SEQ ID NOs: 81-88. These variants can also be used to generate a self-immolative backbone. One self-immolative ampicillin (SEQ ID NO: 89) was found to not be functional.

1.3 Self-Immolative Ori

In Silico Analysis and Experimental Approach

In the 674 bp region of the origin of replication several mutations were taken into account. The changes selected for were based on the different domains or structures present in the Ori (A. Waugh et al., RNAML: A standard syntax for exchanging RNA information. RNA (2002) 8, 707-717). The initial design consisted of a variety of changes in the 300 bp at the 3' of the Ori.

Multiple mutations in a conventional Ori derived from pUC (SEQ ID NO: 20) were designed harbouring single nucleotide changes (SEQ ID NO: 90) as well as single nucleotide insertions (SEQ ID NO: 91) at the 3' of Ori, as well as insertions and nucleotide changes in the center of the Ori (SEQ ID NO: 92) and the stem-loop (SEQ ID NO: 93) which is located between nucleotides 220-310 of the original plasmid backbone sequence (SEQ ID NO: 1). Transformants harboring the mutated Ori were generated as described above. In vivo, the performance of the Ori-modified plasmids was dependent on the exact sequence. For instance, specific mutations at the 3' of the Ori (see SEQ ID NO: 90) resulted in an Ori whose plasmids yielded transformants with reduced viability, as did the mutations in SEQ ID NOs: 117 and 118.

Successful designs (consisting of changes SEQ ID NO: 94 and SEQ ID NO: 95) and an insert upstream of the Ori (SEQ ID NO: 96) were found using the process described above. They were combined to obtain an Ori with MluI restriction sites that were separated by a maximum of 580 nt. This Ori, in turn, was combined with three new mutations in the Ori bearing the restriction sites for BstZ17I (SEQ ID NO: 97, SEQ ID NO: 98, and SEQ ID NO: 99). SEQ ID NO: 99 was selected for further use and the plasmid harbouring it was fully functional, displaying a copy number and plasmid yield similar to SEQ ID NO: 1. SEQ ID NO: 98 and SEQ ID NO: 97 were also functional.

1.4 Self-Immolative Multiple Cloning Site (MCS)

A 52 bp multiple cloning site (MCS) was introduced, including unique recognition sites for SbfI, PstI, NotI, BssHII, SalI and AflII (SEQ ID NO: 19). Owing to its short size, this MCS does not require a cleavage site that is one of the self-immolative cleavage sites.

BssHII is compatible with MluI, so the use of the combination of these three enzymes is beneficial for easy introduction or removal of a fragment of interest via BssHII, and later plasmid degradation via MluI and BstZ17I.

1.5 Assembly into a Vector

A self-immolative vector comprising a resistance marker (SEQ ID NO: 14), an Ori (SEQ ID NO: 27), and a MCS (SEQ ID NO: 19) was assembled (SEQ ID NO: 68) and sequence verified. The plasmid could be selected, had good copy number, and features an MCS allowing insertion of a region of interest. After degradation of its sequence by restriction digestion the size of the backbone vector fragments ranges from 121 to 342 bp (342-241-301-173-211-269-210-121 bp).

Example 2—Isolating an Insert from Degraded Backbone 2.1 Immolation of a Plasmid with an Insert Into a plasmid consisting of a self-immolative backbone (SEQ ID NO: 68) an insert was introduced consisting of a secreted alkaline phosphatase (SeAP) coding sequence (SEQ ID NO: 100), preceded by Expression Enhancing Element 1 (SEQ ID NO: 59) and the CMV promoter (SEQ ID NO: 61) and the GS selection marker (SEQ ID NO: 101). This plasmid was treated with MluI and BStZ17I under conditions prescribed by the enzymes' supplier. After digestion, the insert was purified as described below.

2.2.1 Size Exclusion Chromatography, Milliliter Scale

Sephacryl S-500 gel filtration column chromatography was carried out to purify the insert from degraded undesired DNA. A HiPrep 16/60 Sephacryl S-500 HR ID16 mm column (GE Healthcare Life Science) mounted on an Akta Pure was rinsed with degassed milliQ water and equilibrated with running buffer (RB=100 mM NaCl, 10 mM Tris/HCl pH=8.5) with a flow of 0.5 ml/min at 37° C. 0.95 ml DNA solution was applied. The column was run with running buffer at a flow of 0.5 ml/min. 2 ml fractions were collected.

Figure 3:
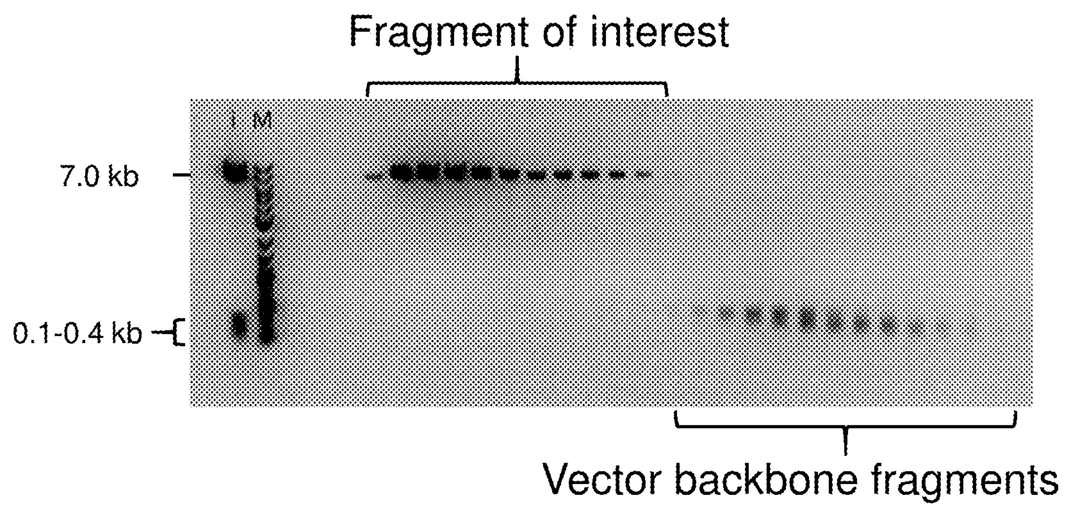
FIG. 3—Baseline separation of Fragment of interest from backbone fragments by Sephacryl S500HR filtration. Analysis of samples: Lane 1 (I) Input sample; Lane 2 (M) 2 Log DNA ladder; Lane 3 to 28: Fractions. The lanes comprising insert are indicated as "Fragment of interest" and the lanes comprising backbone fragments are indicated as "Vector backbone fragments."

Samples were analyzed by gel-electrophoresis (FIG. 3). The insert containing the region of interest (band >7000) and the backbone fragments (121-342 bp) are present in distinct fractions. The method clearly allows a purity level of >99.9%, as fragment of interest is fully separated from backbone fragments.

2.2.2 Size Exclusion Chromatography, Microliter Scale (ChromaSpin-1000)

The ChromaSpin-1000 column (Takara/Clontech) was developed for size-dependent separation of DNA. Suppliers' specifications indicate removal of DNA smaller than 420 bp with an efficiency of at least 90% and a removal efficiency of at least 99% efficiency for DNA smaller than 300 bps. The capacity, for 100 μl sample volume and over 90% recovery, is 1 mg/ml.

A ChromaSpin-1000 column was prepared for use by resuspending the matrix by inverting the column ten times, removing bottom and top cap, and placing the column in a collection tube. The column, with the collection tube, was placed in a 14 ml falcon tube and spun (5 min @ 700×g) at room temperature. Columns were placed in fresh collection tubes, 100 μl sample (MluI/BstZ17I digested plasmid (see 2.1) was applied onto the centre of the column matrix and the column with the collection tube, was placed in a 14 ml falcon tube and spun again (5 min @ 700×g) at room temperature. The eluate in the collection tube is the purified insert.

Figure 4:
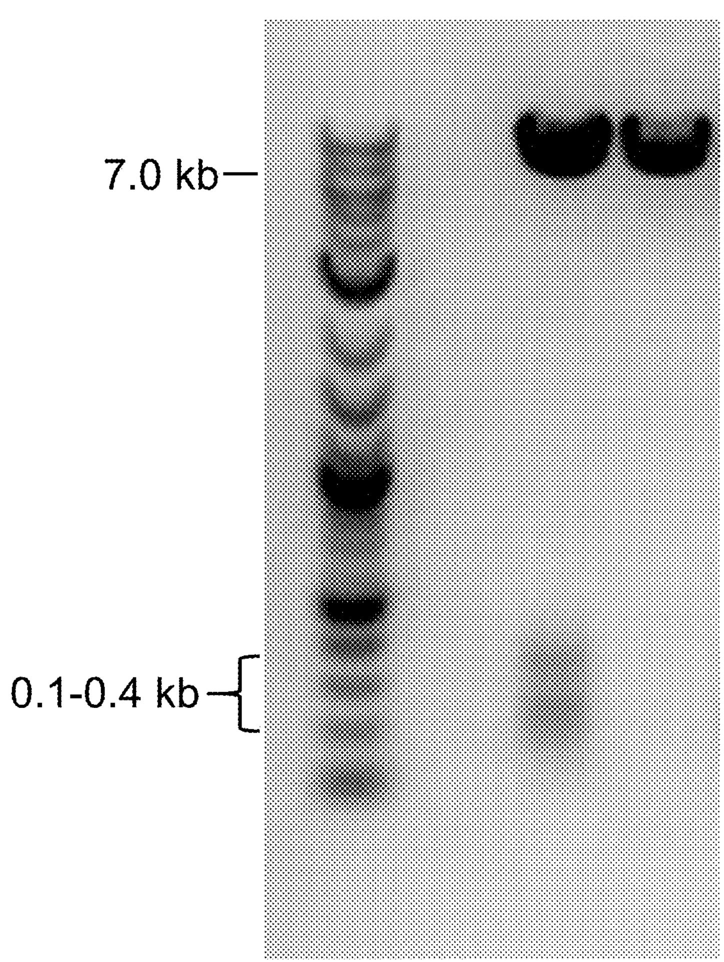

The eluate was analyzed by agarose gel electrophoresis, which indicates that degraded backbone is removed (FIG. 4). Typically, 2-4 mg of plasmid is isolated from 500-600 ml bacterial culture, using Plasmid Maxi Kit (Qiagen). Upon digestion of 100 μl, 1 μg/μl DNA and carrying out clean-up of the insert using the spin column results in 100 μl, 0.4 μg/μl DNA in the filtrate. Thus backbone fragments could be removed after a single non-diluting purification step.

Example 3—Fragment Size and Insert Size can be Matched to Isolation Techniques Dependent on the applications, insert sizes range from approximately 1500 (an average size of a protein gene) to 7000-10000 bp (for multimeric protein-specific cassettes and selection marker sequences). A bacterial backbone (including a resistance marker) is approximately 2000 bp. In this example it was studied whether the properties of commercially available spin column material can separate the fragments. Such spin columns are highly convenient for isolating an insert.

Figure 5:
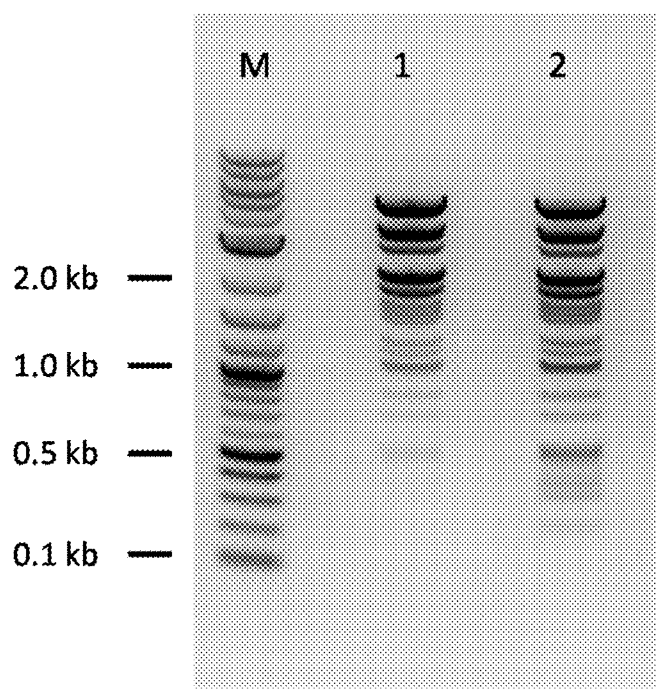
FIG. 5—Separation pattern of spin column material to determine viable ranges of size difference between degraded backbone fragments and insert for a particular spin column. (M): 2 log ladder NEB; (1): Chromaspin1000 eluate of HincII digested λ DNA; (2): HincII digested λ DNA (unpurified).

DNA from Phage Lambda (NEB) was digested with HincII (NEB). Digested DNA was applied on a spin column (see Example 2) and the eluate was analysed by agarose gel electrophoresis (See FIG. 5). Comparison of fragment pattern before and after spin column separation indicates that fragments smaller than 400-500 kb are removed from the eluate whereas fragments larger than 2000 bp are retained in the eluate. Fragments with a size between 500 and 2000 bp are partially captured by the column material. The values are in accordance with the suppliers' specifications which states that over 90% of >2000 bp fragment will in the eluate. With respect to removing fragment DNA it states that over 90% of fragments smaller than 420 bp and over 99% of fragments smaller than 300 bp will be removed from the sample. This confirms that these particular spin columns are best used to remove undesired fragments with a size of 400 bp or smaller from inserts with a size of 2000 bp or larger.

By using different spin column materials (e.g. Sephacryl S-500 HR (GE Healthcare) in columns (Pierce) or Chromaspin 400) differently sized fragments are separated. For the latter, 90% fragments of smaller than 170 bp are captured by the column, while over 90% of the fragments larger than 950 bp freely pass the column (Chroma Spin Columns User Manual, Clontech, February 2011).

Thus, depending on the preferred size of the insert, a degradable vector backbone may be selected with cleavage sites in the backbone that result in fragments which are removed by choosing the best-fitting separation material, using for example spin columns, sephacryl, or other materials.

Example 4—Quality Verification of Insert Isolated from Degraded Backbone 4.1 DNA Purity Analysis of Agarose-Gel Isolated and Shredded-Spin Column Purified DNA The invention allows omitting the use of a purification step (agarose purification) which is prone to chemical and biological contamination of isolated DNA. A key chemical impurity in DNA after isolation from agarose gel is guanidinium, which is used to dissolve agarose gel. Its presence can be detected during DNA concentration determination and analysis with nanodrop measurement equipment (OD 230/OD 260/OD280).

DNA was purified using either Chroma Spin columns or agarose gel isolation. Agarose gel isolation consists of the following steps: 1. Running a quantitative amount of DNA on agarose gel; 2. Isolation of the DNA by cutting out the piece of gel harbouring the DNA of interest; 3. Dissolving the agarose by adding 2 volumes of guanidinium containing buffer per volume of agarose gel; 4. Applying the DNA to column material, rinsing the column material twice and eluting the DNA from the column (in two steps).

The use of spin columns is described in the previous examples. Besides not requiring manual dexterity for cutting out a relevant piece of gel, the spin columns only required about 15 minutes of time, where the gel extraction required about 3 hours in total.

In a gel-extraction experiment one time the protocol was followed meticulously, while in a parallel experiment the centrifugation step was different. DNA quality is measured by absorbance ratio's (260:280 nm and 260:230 nm). Isolation from agarose gel provided the following values for isolated inserts:

$$A260/A280=1.79-1.80, A260/A230=0.5-0.75; \quad \text{Experiment 1:}$$

$$A260/A280=1.86-1.86, A260/A230=1.96-2.11. \quad \text{Experiment 2:}$$

Only the values of the second experiment meet common specifications (PCR clean-up Gel extraction User manual NucleoSpin® Gel and PCR Clean-up, Machery-Nagel February 2017/Rev. 04). The cause for the deviating values of the first experiment was attributed to the presence of guanidium due to incomplete removal of the agarose solubilizing buffer. The second experiment was carried out meticulously according to protocol.

The data from three representative insert isolation experiments using the backbone-degradation spin column removal method resulted in the following quality levels:

$$A260/A280=1.87, A260/A230=2.01; \quad \text{Experiment 1:}$$

$$A260/A280=1.85, A260/A230=2.05; \quad \text{Experiment 2:}$$

$$A260/A280=1.88, A260/A230=1.99. \quad \text{Experiment 3:}$$

All three experiments resulted in values that meet specifications. Thus it follows that adequate purification from agarose gel depends on properly carrying out protocol, while purification by (spin)column results in DNA which is of at least the same quality as agarose-gel purified DNA, but which is much more robust in variations in protocol.

4.2 Endotoxin Contamination Measurements

A relevant biological DNA contaminant is endotoxin. The quality of isolated materials is also determined by the risk of the DNA isolation method to introduce endotoxin. Therefore, in a parallel experiment, a comparison was made between the endotoxin level in DNA samples purified using either agarose gel isolation (see example 4.1) or spin columns (see example 2). The detection was carried out using an assay kit. This method utilizes a modified Limulus Amebocyte Lysate (LAL) in the presence of a chromogenic substrate. In the presence of endotoxin the LAL reacts with the substrate resulting in a quantitative change in absorbance. The endotoxin level of samples was determined relative to the amount of endotoxin in a standard range using the manual of the supplier (ToxinSensor™ Chromogenic LAL Endotoxin Assay Kit, GenScript). The absorbance was measured at 540 nm (EnSpire, Perkin Elmer).

Endotoxin levels of 9 spin column purified DNA samples ranged from $3E^{-6}$ to $9E^{-3}$ EU/μg DNA and an average of $2.1E^{-3}$ EU/μg DNA. Conversely, the levels, measured for three gel-purified DNA samples, ranged from $2.6E^{-1}$ to $3.5E^{-1}$ EU/μg DNA, with an average of $3.2E^{-1}$ EU/μg DNA. It follows that the self-immolative vector allows use of convenient techniques that also contribute to avoiding contaminants.

4.3 Functionality of Isolated Inserts

The functionality of backbone degraded-spin column purified fragment of interest was compared with fragment of interest generated by classical digestion-agarose purification. As example the expression of SeAP in stable mammalian cell pools was measured.

4.3.1 Transfection of Agarose Insert and Self-Immolation Insert

Two DNA solutions were made to compare the effect of the DNA purification method on the expression of seAP in CHO-GS−/− cells. The expression cassettes (see Example 2) were identical and harboured an intronic promoter and an additional expression regulating element (see also WO2015/102487). In one case the seAP expression cassette was isolated from the vector backbone using agarose gel isolation (see earlier Example); in the second case MluI/Bst17I digestion of the plasmid, resulting in fragmentation of the backbone, was followed by spin-column purification of the expression cassette (see method in earlier Example).

CHO-GS−/− cells (Horizon Discovery) were maintained per manufacturer's instructions. Quadruplicate transfections were performed using $3E^{6}$ cells in 3 ml CD CHO medium (Gibco), 5 μg of agarose-gel purified or backbone degraded/spin column purified DNA and 5 μl FreeStyle MAX Reagent (Life Technologies). Post-transfection pools were selected static in 6 well plates in 4 ml CD CHO medium (Gibco) at 37° C., 6% $CO_2$. At the start of recovery cells were transferred to T75 Flasks and cultured into 8-12 ml till a VCD of >$1E^{6}$ cells/ml and >60% viable.

Cells were transferred to a 125 ml shake flask and cultured until cells reached a viable cell density above 90%. Stable pools were seeded in 30 ml CD forti CHO medium (Gibco) at a density of $4E^{5}$ cells/ml in shake flasks. The cells were cultured for 9-11 days till viable cell density dropped below 40%. The SeAP exhaust titers were determined with a SEAP Reporter Gene Assay Kit (ab13307, Abcam) using the Enspire (Perkin Elmer).

Exhaust titers of stable cell pools with backbone degraded/spin column purified DNA were 2.0 U/ml, whereas the titer of cells with the agarose fragment isolated DNA was 1.7 U/ml. So the yield of SeAP is similar irrespective whether backbone degraded/spin column purified or agarose-gel purified fragment of interest is used.

In the same experiment the effect of removing the bacterial backbone per se was also determined. Stable cell pools generated with spin column purified, linearized plasmid, i.e. without digesting the plasmid backbone, resulted in an exhaust seAP titer of 1.1 U/ml. This indicates that removal of the backbone by application of the shredder-removal method improves the performance of the expression cassette described in WO 2015/102487.

The invention claimed is:

1. A method for separating a polynucleotide insert from a polynucleotide vector backbone, the method comprising the steps of i) providing a recombinant polynucleotide vector comprising the insert and the vector backbone, wherein the vector backbone comprises a first plurality of cleavage sites that divide the vector backbone into fragments, wherein all fragments are selected from a length of at most 1000 bp and at least 40 bp;

ii) contacting the recombinant vector with cleavage means capable of specifically cleaving the first plurality of cleavage sites to produce backbone fragments and the insert; and optionally, iii) separating the insert from the backbone fragments of step ii).

2. The method according to claim 1, wherein the separation of step iii uses a technique selected from the group consisting of a spin column, a size exclusion column, and solid phase reversible immobilization (SPRI).

3. The method according to claim 1, wherein the cleavage means are selected from the group consisting of a restriction enzyme, an RNA-guided DNA endonuclease enzyme, a sequence-specific nuclease, sequence-specific ultrasonication, a sequence-specific oxidative small molecule, and a sequence-specific hydrolyzing small molecule.

4. The method according to claim 1, wherein the cleavage sites from the first plurality of cleavage sites are restriction sites.

5. The method according to claim 1, wherein the cleavage means comprise 3, 2, or 1 species of restriction enzymes.

6. The method according to claim 1, wherein the insert inside does not comprise a cleavage site of the first plurality of cleavage sites.

7. The method according to claim 1, wherein the vector backbone further comprises a polynucleotide encoding a functional selection marker.

8. The method according to claim 1, wherein the fragments have a length of at most 900, 800, 700, 650, 600, 550, 500, 450, 400, 350, 300, 250, 200, 150, or 100 bp or less.

9. The method according to claim 1, wherein the vector backbone further comprises a multiple cloning site that does not comprise a cleavage site of the first plurality of cleavage sites.

10. A method for amplifying a polynucleotide of interest, the method comprising the steps of i) providing a recombinant polynucleotide vector comprising the polynucleotide of interest as an insert, and the vector backbone as defined in claim 1;

ii) amplifying the recombinant polynucleotide vector of step i) by transforming a suitable microorganism with the recombinant polynucleotide vector, and culturing said transformed microorganism in a culture medium under conditions suitable for vector amplification to obtain amplified recombinant polynucleotide vector;

iii) isolating the amplified recombinant polynucleotide vector from the culture medium of step ii) to obtain isolated amplified recombinant polynucleotide vector;

iv) contacting the isolated amplified recombinant polynucleotide vector with cleavage means capable of cleaving the first plurality of cleavage sites to produce backbone fragments and the polynucleotide of interest; and optionally, v) separating the polynucleotide of interest from the backbone fragments of step iv).

11. A polynucleotide vector backbone as defined in claim 1.

12. The polynucleotide vector backbone according to claim 11, wherein the vector backbone has at least 70% sequence identity with any one of SEQ ID NOs: 68 and 80.

13. The polynucleotide vector backbone according to claim 11, wherein the cleavage sites from the first plurality of cleavage sites are restriction sites.

14. A recombinant polynucleotide vector comprising a polynucleotide insert and the polynucleotide vector backbone as defined in claim 11.

15. A kit of parts comprising:

i) the polynucleotide vector backbone as defined in claim 1, or a recombinant polynucleotide vector comprising a polynucleotide insert and the polynucleotide vector backbone; and at least one of iia) materials for use in the separating step iii of claim 1, wherein the separation technique is selected from the group consisting of a spin column, a size exclusion column, and solid phase reversible immobilization (SPRI); or iib) cleavage means selected from the group consisting of a restriction enzyme, an RNA-guided DNA endonuclease enzyme, a sequence-specific nuclease, sequence-specific ultrasonication, a sequence-specific oxidative small molecule, and a sequence-specific hydrolyzing small molecule.

16. A method for enhancing transcription of a nucleotide sequence of interest in a eukaryotic cell, the method comprising the steps of:

i) providing a recombinant polynucleotide vector comprising the nucleotide surface of interest as an insert, and a vector backbone as defined in claim 1;

ii) amplifying the recombinant polynucleotide vector of step i) by transfecting the recombinant polynucleotide vector to a suitable microorganism and culturing said microorganism in a culture medium under conditions suitable for vector amplification to obtain amplified recombinant polynucleotide vector;

iii) isolating the amplified recombinant polynucleotide vector from the culture medium of step ii) to obtain isolated amplified recombinant polynucleotide vector;

iv) contacting the isolated amplified recombinant polynucleotide vector with cleavage means capable of cleaving the first plurality of cleavage sites to produce backbone fragments and the nucleotide surface of interest;

v) separating the nucleotide sequence of interest from the backbone fragments of step iv) to obtain an isolated nucleotide sequence of interest;

vi) integrating the isolated nucleotide sequence of interest into the genome of a eukaryotic cell to obtain a transgenic cell; and vii) culturing the transgenic cell under conditions conducive to expression of the nucleotide sequence of interest.

17. The method according to claim 5, wherein the restriction enzyme recognizes a restriction site of 6 or 7 nucleotides.

18. The method according to claim 7, wherein the polynucleotide encoding a functional selection marker is selected from the group consisting of SEQ ID NOs: 14-18, 79, and 110-116, or is selected from the group consisting of SEQ ID NOs: 69, 70, and 81-88.

19. The method according to claim 8, wherein the fragments have a length of at most 550 bp.

* * * * *